US010334848B2

(12) United States Patent
Navarro

(10) Patent No.: US 10,334,848 B2
(45) Date of Patent: Jul. 2, 2019

(54) METHODS AND COMPOSITIONS FOR WEED CONTROL USING EPSPS POLYNUCLEOTIDES

(71) Applicant: Monsanto Technology LLC, St. Louis, MO (US)

(72) Inventor: Santiago X. Navarro, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/111,729

(22) PCT Filed: Jan. 14, 2015

(86) PCT No.: PCT/US2015/011408
§ 371 (c)(1),
(2) Date: Jul. 14, 2016

(87) PCT Pub. No.: WO2015/108982
PCT Pub. Date: Jul. 23, 2015

(65) Prior Publication Data
US 2016/0330967 A1 Nov. 17, 2016

Related U.S. Application Data

(60) Provisional application No. 61/927,682, filed on Jan. 15, 2014.

(51) Int. Cl.
*C12N 15/82* (2006.01)
*A01N 37/40* (2006.01)
*A01N 57/20* (2006.01)

(52) U.S. Cl.
CPC ............. *A01N 37/40* (2013.01); *A01N 57/20* (2013.01); *C12N 15/8261* (2013.01); *C12N 15/8274* (2013.01); *C12N 15/8275* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,469,863 A | 9/1984 | Ts'o et al. |
| 4,476,301 A | 10/1984 | Imbach et al. |
| 4,535,060 A | 8/1985 | Comai |
| 4,581,847 A | 4/1986 | Hibberd et al. |
| 4,666,828 A | 5/1987 | Gusella |
| 4,683,202 A | 7/1987 | Mullis |
| 4,761,373 A | 8/1988 | Anderson et al. |
| 4,769,061 A | 9/1988 | Comai |
| 4,801,531 A | 1/1989 | Frossard |
| 4,810,648 A | 3/1989 | Stalker |
| 4,879,219 A | 11/1989 | Wands et al. |
| 4,940,835 A | 7/1990 | Shah et al. |
| 4,971,908 A | 11/1990 | Kishore et al. |
| 5,004,863 A | 4/1991 | Umbeck |
| 5,011,771 A | 4/1991 | Bellet et al. |
| 5,013,659 A | 5/1991 | Bedbrook et al. |
| 5,015,580 A | 5/1991 | Christou et al. |
| 5,023,243 A | 6/1991 | Tullis |
| 5,034,506 A | 7/1991 | Summerton et al. |
| 5,094,945 A | 3/1992 | Comai |
| 5,141,870 A | 8/1992 | Bedbrook et al. |
| 5,145,783 A | 9/1992 | Kishore et al. |
| 5,159,135 A | 10/1992 | Umbeck |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,642 A | 2/1993 | Shah et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,272,057 A | 12/1993 | Smulson et al. |
| 5,276,019 A | 1/1994 | Cohen et al. |
| 5,281,521 A | 1/1994 | Trojanowski et al. |
| 5,286,634 A | 2/1994 | Stadler et al. |
| 5,286,717 A | 2/1994 | Cohen et al. |
| 5,304,732 A | 4/1994 | Anderson et al. |
| 5,310,667 A | 5/1994 | Eichholtz et al. |

(Continued)

FOREIGN PATENT DOCUMENTS

AU 2008258254 B2 7/2014
CN 101279950 A 10/2008

(Continued)

OTHER PUBLICATIONS

GenBank Accession No. FJ861242.1, Amaranthus palmeri 5-enolpyruvylshikimate-3-phosphate synthase (EPSPS) mRNA, Feb. 3, 2010 (Year: 2010).*

(Continued)

*Primary Examiner* — Eileen B O Hara
(74) *Attorney, Agent, or Firm* — Amanda Carmany-Rampey; Arnold & Porter Kaye Scholer LLP

(57) ABSTRACT

Provided are novel polynucleotide compositions for enhancing the herbicidal activity of glyphosate. Specifically provided are methods and compositions for modulating 5-enolpyruvylshikimate-3-phosphate synthase (EPSPS) in plant species. The present compositions and methods are useful in controlling glyphosate resistant weeds.

18 Claims, 4 Drawing Sheets

Figure 1:
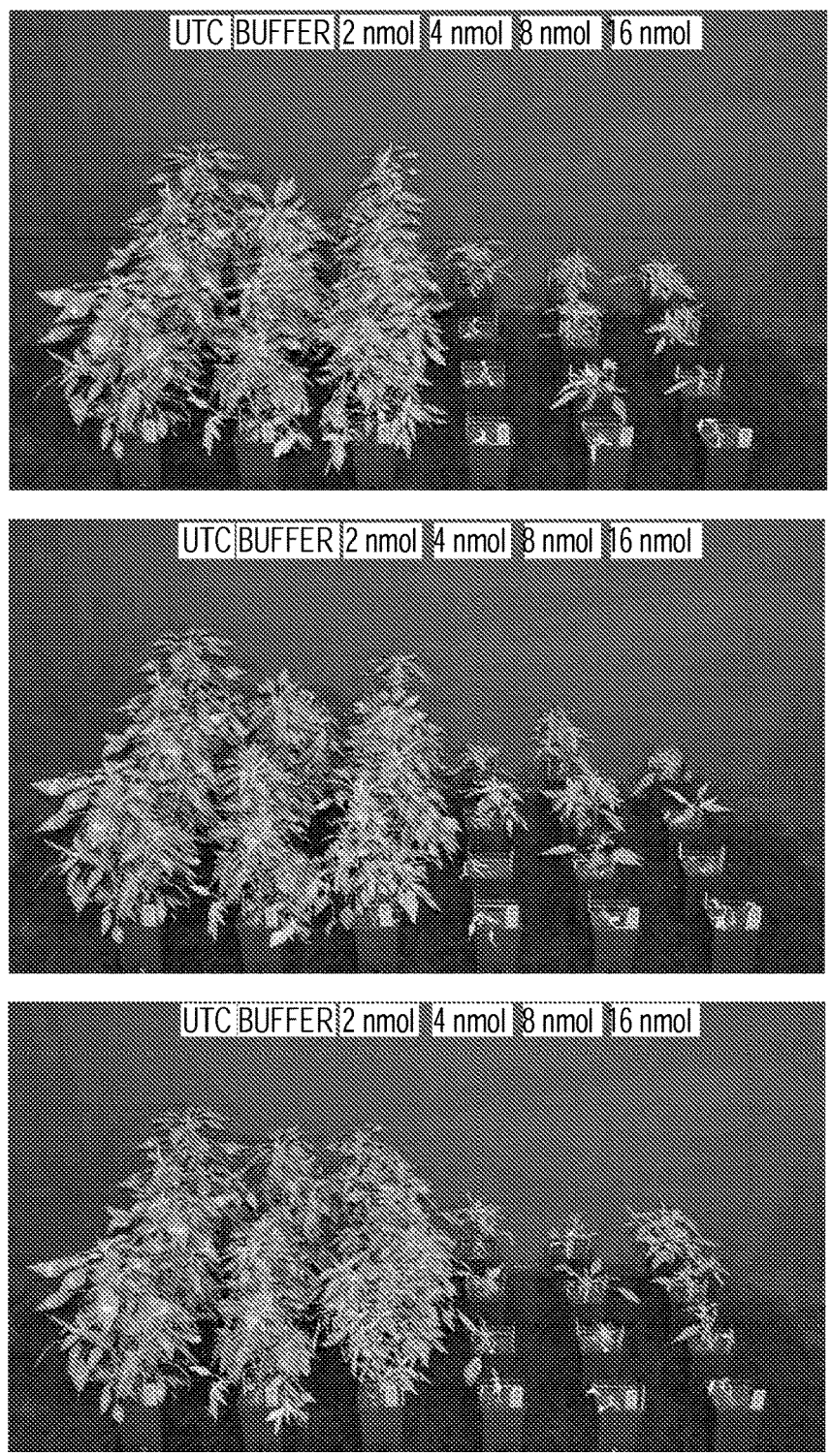

Specification includes a Sequence Listing.

(56) References Cited

U.S. PATENT DOCUMENTS

| | | |
|---|---|---|
| 5,312,910 A | 5/1994 | Kishore et al. |
| 5,321,131 A | 6/1994 | Agrawal et al. |
| 5,331,107 A | 7/1994 | Anderson et al. |
| 5,339,107 A | 8/1994 | Henry et al. |
| 5,346,107 A | 9/1994 | Bouix et al. |
| 5,378,824 A | 1/1995 | Bedbrook et al. |
| 5,390,667 A | 2/1995 | Kumakura et al. |
| 5,392,910 A | 2/1995 | Bell et al. |
| 5,393,175 A | 2/1995 | Courville |
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,459,127 A | 10/1995 | Felgner et al. |
| 5,460,667 A | 10/1995 | Moriyuki et al. |
| 5,462,910 A | 10/1995 | Ito et al. |
| 5,463,174 A | 10/1995 | Moloney et al. |
| 5,463,175 A | 10/1995 | Barry et al. |
| 5,466,677 A | 11/1995 | Baxter et al. |
| 5,470,967 A | 11/1995 | Huie et al. |
| 5,476,925 A | 12/1995 | Letsinger et al. |
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,518,908 A | 5/1996 | Corbin et al. |
| 5,519,126 A | 5/1996 | Hecht |
| 5,536,821 A | 7/1996 | Agrawal et al. |
| 5,538,880 A | 7/1996 | Lundquist et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,550,318 A | 8/1996 | Adams et al. |
| 5,550,398 A | 8/1996 | Kocian et al. |
| 5,550,468 A | 8/1996 | Häberlein et al. |
| 5,558,071 A | 9/1996 | Ward et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,597,717 A | 1/1997 | Guerineau et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischofberger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,719,046 A | 2/1998 | Guerineau et al. |
| 5,721,138 A | 2/1998 | Lawn |
| 5,731,180 A | 3/1998 | Dietrich |
| 5,739,180 A | 4/1998 | Taylor-Smith |
| 5,746,180 A | 5/1998 | Jefferson et al. |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,837,848 A | 11/1998 | Ely et al. |
| 5,859,347 A | 1/1999 | Brown et al. |
| 5,866,775 A | 2/1999 | Eichholtz et al. |
| 5,874,265 A | 2/1999 | Adams et al. |
| 5,879,903 A | 3/1999 | Strauch et al. |
| 5,914,451 A | 6/1999 | Martinell et al. |
| 5,919,675 A | 7/1999 | Adams et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A | 11/1999 | Sandbrink et al. |
| RE36,449 E | 12/1999 | Lebrun et al. |
| 6,040,497 A | 3/2000 | Spencer et al. |
| 6,056,938 A | 5/2000 | Unger et al. |
| 6,069,115 A | 5/2000 | Pallett et al. |
| 6,084,089 A | 7/2000 | Mine et al. |
| 6,084,155 A | 7/2000 | Volrath et al. |
| 6,118,047 A | 9/2000 | Anderson et al. |
| 6,121,513 A | 9/2000 | Zhang et al. |
| 6,130,366 A | 10/2000 | Herrera-Estrella et al. |
| 6,140,078 A | 10/2000 | Sanders et al. |
| 6,153,812 A | 11/2000 | Fry et al. |
| 6,160,208 A | 12/2000 | Lundquist et al. |
| 6,177,616 B1 | 1/2001 | Bartsch et al. |
| 6,194,636 B1 | 2/2001 | McElroy et al. |
| 6,225,105 B1 | 5/2001 | Sathasivan et al. |
| 6,225,114 B1 | 5/2001 | Eichholtz et al. |
| 6,232,526 B1 | 5/2001 | McElroy et al. |
| 6,245,968 B1 | 6/2001 | Boudec et al. |
| 6,248,876 B1 | 6/2001 | Barry et al. |
| 6,252,138 B1 | 6/2001 | Karimi et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,326,193 B1 | 12/2001 | Liu et al. |
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,426,446 B1 | 7/2002 | McElroy et al. |
| 6,433,252 B1 | 8/2002 | Kriz et al. |
| 6,437,217 B1 | 8/2002 | McElroy et al. |
| 6,453,609 B1 | 9/2002 | Soll et al. |
| 6,479,291 B2 | 11/2002 | Kumagai et al. |
| 6,506,559 B1 | 1/2003 | Fire et al. |
| 6,642,435 B1 | 11/2003 | Rafalski et al. |
| 6,644,341 B1 | 11/2003 | Chemo et al. |
| 6,645,914 B1 | 11/2003 | Woznica et al. |
| 6,768,044 B1 | 7/2004 | Boudec et al. |
| 6,992,237 B1 | 1/2006 | Habben et al. |
| 7,022,896 B1 | 4/2006 | Weeks et al. |
| 7,026,528 B2 | 4/2006 | Cheng et al. |
| RE39,247 E | 8/2006 | Barry et al. |
| 7,105,724 B2 | 9/2006 | Weeks et al. |
| 7,119,256 B2 | 10/2006 | Shimizu et al. |
| 7,138,564 B2 | 11/2006 | Tian et al. |
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |
| 7,371,927 B2 | 5/2008 | Yao et al. |
| 7,392,379 B2 | 6/2008 | Le Pennec et al. |
| 7,405,347 B2 | 7/2008 | Hammer et al. |
| 7,406,981 B2 | 8/2008 | Hemo et al. |
| 7,462,379 B2 | 12/2008 | Fukuda et al. |
| 7,485,777 B2 | 2/2009 | Nakajima et al. |
| 7,525,013 B2 | 4/2009 | Hildebrand et al. |
| 7,550,578 B2 | 6/2009 | Budworth et al. |
| 7,622,301 B2 | 11/2009 | Ren et al. |

(56) References Cited

U.S. PATENT DOCUMENTS

| | | |
|---|---|---|
| 7,657,299 B2 | 2/2010 | Huizenga et al. |
| 7,671,254 B2 | 3/2010 | Tranel et al. |
| 7,714,188 B2 | 5/2010 | Castle et al. |
| 7,738,626 B2 | 6/2010 | Weese et al. |
| 7,807,791 B2 | 10/2010 | Sekar et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,090,164 B2 | 1/2012 | Bullitt et al. |
| 8,143,480 B2 | 3/2012 | Axtell et al. |
| 8,548,778 B1 | 10/2013 | Hart et al. |
| 8,554,490 B2 | 10/2013 | Tang et al. |
| 9,121,022 B2 * | 9/2015 | Sammons ............... A01N 63/02 |
| 9,422,557 B2 * | 8/2016 | Ader ....................... A01N 65/00 |
| 9,445,603 B2 | 9/2016 | Baum et al. |
| 2001/0006797 A1 | 7/2001 | Kumagai et al. |
| 2001/0042257 A1 | 11/2001 | Connor-Ward et al. |
| 2002/0069430 A1 | 6/2002 | Kiaska et al. |
| 2002/0114784 A1 | 8/2002 | Li et al. |
| 2003/0150017 A1 | 8/2003 | Mesa et al. |
| 2003/0154508 A1 | 8/2003 | Stevens et al. |
| 2003/0167537 A1 | 9/2003 | Jiang |
| 2004/0029275 A1 | 2/2004 | Brown et al. |
| 2004/0053289 A1 | 3/2004 | Allen et al. |
| 2004/0055041 A1 | 3/2004 | Labate et al. |
| 2004/0072692 A1 | 4/2004 | Hoffman et al. |
| 2004/0082475 A1 | 4/2004 | Hoffman et al. |
| 2004/0123347 A1 | 6/2004 | Hinchey et al. |
| 2004/0126845 A1 | 7/2004 | Eenennaam et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0216189 A1 | 10/2004 | Houmard et al. |
| 2004/0244075 A1 | 12/2004 | Cai et al. |
| 2004/0250310 A1 | 12/2004 | Shukla et al. |
| 2005/0005319 A1 | 1/2005 | della-Cioppa et al. |
| 2005/0044591 A1 | 2/2005 | Yao et al. |
| 2005/0215435 A1 | 9/2005 | Menges et al. |
| 2005/0246784 A1 | 11/2005 | Plesch et al. |
| 2005/0250647 A1 | 11/2005 | Hills et al. |
| 2006/0009358 A1 | 1/2006 | Kibler et al. |
| 2006/0021087 A1 | 1/2006 | Baum et al. |
| 2006/0040826 A1 | 2/2006 | Eaton et al. |
| 2006/0111241 A1 | 5/2006 | Gerwick, III et al. |
| 2006/0130172 A1 | 6/2006 | Whaley et al. |
| 2006/0135758 A1 | 6/2006 | Wu |
| 2006/0200878 A1 | 9/2006 | Lutfiyya et al. |
| 2006/0223708 A1 | 10/2006 | Hoffmann et al. |
| 2006/0223709 A1 | 10/2006 | Helmke et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011775 A1 | 1/2007 | Allen et al. |
| 2007/0021360 A1 | 1/2007 | Nyce et al. |
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0250947 A1 | 10/2007 | Boukharov et al. |
| 2007/0259785 A1 | 11/2007 | Heck et al. |
| 2007/0269815 A1 | 11/2007 | Rivory et al. |
| 2007/0281900 A1 | 12/2007 | Cui et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0113351 A1 | 5/2008 | Naito et al. |
| 2008/0155716 A1 | 6/2008 | Sonnewald et al. |
| 2008/0214443 A1 | 9/2008 | Baum et al. |
| 2009/0011934 A1 | 1/2009 | Zawierucha et al. |
| 2009/0018016 A1 | 1/2009 | Duck et al. |
| 2009/0036311 A1 | 2/2009 | Witschel et al. |
| 2009/0054240 A1 | 2/2009 | Witschel et al. |
| 2009/0075921 A1 | 3/2009 | Ikegawa et al. |
| 2009/0098614 A1 | 4/2009 | Zamore et al. |
| 2009/0118214 A1 | 5/2009 | Paldi et al. |
| 2009/0137395 A1 | 5/2009 | Chicoine et al. |
| 2009/0165153 A1 | 6/2009 | Wang et al. |
| 2009/0165166 A1 | 6/2009 | Feng et al. |
| 2009/0172838 A1 | 7/2009 | Axtell et al. |
| 2009/0188005 A1 | 7/2009 | Boukharov et al. |
| 2009/0205079 A1 | 8/2009 | Kumar et al. |
| 2009/0215628 A1 | 8/2009 | Witschel et al. |
| 2009/0285784 A1 | 11/2009 | Raemaekers et al. |
| 2009/0293148 A1 | 11/2009 | Ren et al. |
| 2009/0298787 A1 | 12/2009 | Raemaekers et al. |
| 2009/0306189 A1 | 12/2009 | Raemaekers et al. |
| 2009/0307803 A1 | 12/2009 | Baum et al. |
| 2010/0005551 A1 | 1/2010 | Roberts et al. |
| 2010/0048670 A1 | 2/2010 | Biard et al. |
| 2010/0068172 A1 | 3/2010 | Van De Craen |
| 2010/0071088 A1 | 3/2010 | Sela et al. |
| 2010/0099561 A1 | 4/2010 | Selby et al. |
| 2010/0100988 A1 | 4/2010 | Tranel et al. |
| 2010/0152443 A1 | 6/2010 | Hirai et al. |
| 2010/0154083 A1 | 6/2010 | Ross et al. |
| 2010/0192237 A1 | 7/2010 | Ren et al. |
| 2010/0247578 A1 | 9/2010 | Salama |
| 2011/0015084 A1 | 1/2011 | Christian et al. |
| 2011/0015284 A1 | 1/2011 | Dees et al. |
| 2011/0028412 A1 | 2/2011 | Cappello et al. |
| 2011/0035836 A1 | 2/2011 | Eudes et al. |
| 2011/0041400 A1 | 2/2011 | Trias Vila et al. |
| 2011/0053226 A1 | 3/2011 | Rohayem |
| 2011/0098180 A1 | 4/2011 | Michel et al. |
| 2011/0105327 A1 | 5/2011 | Nelson |
| 2011/0105329 A1 | 5/2011 | Song et al. |
| 2011/0112570 A1 | 5/2011 | Mannava et al. |
| 2011/0126310 A1 | 5/2011 | Feng et al. |
| 2011/0126311 A1 | 5/2011 | Velcheva et al. |
| 2011/0152339 A1 | 6/2011 | Brown et al. |
| 2011/0152346 A1 | 6/2011 | Karleson et al. |
| 2011/0152353 A1 | 6/2011 | Koizumi et al. |
| 2011/0160082 A1 | 6/2011 | Woo et al. |
| 2011/0166022 A1 | 7/2011 | Israels et al. |
| 2011/0166023 A1 | 7/2011 | Nettleton-Hammond et al. |
| 2011/0171176 A1 | 7/2011 | Baas et al. |
| 2011/0171287 A1 | 7/2011 | Saarma et al. |
| 2011/0177949 A1 | 7/2011 | Krapp et al. |
| 2011/0185444 A1 | 7/2011 | Li et al. |
| 2011/0185445 A1 | 7/2011 | Bogner et al. |
| 2011/0191897 A1 | 8/2011 | Poree et al. |
| 2011/0201501 A1 | 8/2011 | Song et al. |
| 2011/0296555 A1 | 12/2011 | Ivashuta et al. |
| 2011/0296556 A1 | 12/2011 | Sammons et al. |
| 2012/0036594 A1 | 2/2012 | Cardoza et al. |
| 2012/0107355 A1 | 5/2012 | Harris et al. |
| 2012/0108497 A1 | 5/2012 | Paldi et al. |
| 2012/0137387 A1 | 5/2012 | Baum et al. |
| 2012/0150048 A1 | 6/2012 | Kang et al. |
| 2012/0156784 A1 | 6/2012 | Adams, Jr. et al. |
| 2012/0157512 A1 | 6/2012 | Ben-Chanoch et al. |
| 2012/0164205 A1 | 6/2012 | Baum et al. |
| 2012/0185967 A1 | 7/2012 | Sela et al. |
| 2012/0198586 A1 | 8/2012 | Narva et al. |
| 2012/0230565 A1 | 9/2012 | Steinberg et al. |
| 2012/0258646 A1 | 10/2012 | Sela et al. |
| 2013/0003213 A1 | 1/2013 | Kabelac et al. |
| 2013/0041004 A1 | 2/2013 | Drager et al. |
| 2013/0047297 A1 * | 2/2013 | Sammons ............... A01N 63/02 |
| | | 800/278 |
| 2013/0047298 A1 | 2/2013 | Tang |
| 2013/0060133 A1 | 3/2013 | Kassab et al. |
| 2013/0067618 A1 * | 3/2013 | Ader ....................... A01H 3/04 |
| | | 800/278 |
| 2013/0084243 A1 | 4/2013 | Goetsch et al. |
| 2013/0096073 A1 | 4/2013 | Sidelman |
| 2013/0097726 A1 * | 4/2013 | Ader ................... C12N 15/8243 |
| | | 800/278 |
| 2013/0212739 A1 | 8/2013 | Giritch et al. |

(56) References Cited

U.S. PATENT DOCUMENTS

| | | | |
|---|---|---|---|
| 2013/0226003 A1 | 8/2013 | Edic et al. | |
| 2013/0247247 A1* | 9/2013 | Ader | A01N 57/16 800/285 |
| 2013/0254940 A1* | 9/2013 | Ader | C12N 9/0004 800/286 |
| 2013/0254941 A1* | 9/2013 | Ader | A01H 3/04 800/286 |
| 2013/0288895 A1* | 10/2013 | Ader | C12N 15/8218 504/127 |
| 2013/0318657 A1 | 11/2013 | Avniel et al. | |
| 2013/0318658 A1 | 11/2013 | Ader et al. | |
| 2013/0324842 A1 | 12/2013 | Mittal et al. | |
| 2013/0326731 A1* | 12/2013 | Ader | A01N 33/18 800/286 |
| 2014/0018241 A1* | 1/2014 | Sammons | A01N 63/02 504/128 |
| 2014/0057789 A1* | 2/2014 | Sammons | A01N 63/02 504/206 |
| 2014/0109258 A1 | 4/2014 | Van De Craen et al. | |
| 2014/0215656 A1* | 7/2014 | Crawford | C12N 15/8282 800/298 |
| 2014/0230090 A1 | 8/2014 | Avniel et al. | |
| 2014/0274712 A1* | 9/2014 | Finnessy | A01N 43/90 504/136 |
| 2014/0275208 A1 | 9/2014 | Hu et al. | |
| 2014/0283211 A1* | 9/2014 | Crawford | C12N 15/8218 800/279 |
| 2014/0296503 A1 | 10/2014 | Avniel et al. | |
| 2015/0096079 A1 | 4/2015 | Avniel et al. | |
| 2015/0143580 A1 | 5/2015 | Beattie et al. | |
| 2015/0159156 A1 | 6/2015 | Inberg et al. | |
| 2015/0203867 A1 | 7/2015 | Beattie et al. | |
| 2015/0240258 A1 | 8/2015 | Beattie et al. | |
| 2016/0015035 A1* | 1/2016 | Tao | A01N 25/30 504/128 |
| 2016/0029644 A1* | 2/2016 | Tao | C12N 15/8218 504/117 |

FOREIGN PATENT DOCUMENTS

| | | |
|---|---|---|
| CN | 101279951 A | 10/2008 |
| CN | 101892247 A | 11/2010 |
| CN | 101914540 A | 12/2010 |
| CN | 102154364 A | 8/2011 |
| CN | 102481311 A | 5/2012 |
| CN | 102822350 A | 12/2012 |
| CN | 102906263 A | 1/2013 |
| DE | 288618 A5 | 4/1991 |
| DE | 10000600 A1 | 7/2001 |
| DE | 10116399 A1 | 10/2002 |
| DE | 10256353 A1 | 6/2003 |
| DE | 10256354 A1 | 6/2003 |
| DE | 10256367 A1 | 6/2003 |
| DE | 10204951 A1 | 8/2003 |
| DE | 10234875 A1 | 2/2004 |
| DE | 10234876 A1 | 2/2004 |
| DE | 102004054666 A1 | 5/2006 |
| DE | 102005014638 A1 | 10/2006 |
| DE | 102005014906 A1 | 10/2006 |
| DE | 102007012168 A1 | 9/2008 |
| DE | 102010042866 A1 | 5/2011 |
| EP | 0 804 600 A1 | 11/1997 |
| EP | 1 157 991 A2 | 11/2001 |
| EP | 1 238 586 A1 | 9/2002 |
| EP | 1 416 049 A1 | 5/2004 |
| EP | 1 496 123 A1 | 1/2005 |
| EP | 1 889 902 A1 | 2/2008 |
| EP | 2 147 919 A1 | 1/2010 |
| EP | 2 160 098 B1 | 11/2010 |
| EP | 2 530 159 A1 | 3/2011 |
| EP | 2 305 813 A2 | 4/2011 |
| EP | 2 545 182 A1 | 1/2013 |
| JP | 2001253874 A | 9/2001 |
| JP | 2002080454 A | 3/2002 |
| JP | 2002138075 A | 5/2002 |
| JP | 2002145707 A | 5/2002 |
| JP | 2002220389 A | 8/2002 |
| JP | 2003064059 A | 3/2003 |
| JP | 2003096059 A | 4/2003 |
| JP | 2004051628 A | 2/2004 |
| JP | 2004107228 A | 4/2004 |
| JP | 2005008583 A | 1/2005 |
| JP | 2005239675 A | 9/2005 |
| JP | 2005314407 A | 11/2005 |
| JP | 2006232824 A | 9/2006 |
| JP | 2006282552 A | 10/2006 |
| JP | 2007153847 A | 6/2007 |
| JP | 2007161701 A | 6/2007 |
| JP | 2007182404 A | 7/2007 |
| JP | 2008074840 A | 4/2008 |
| JP | 2008074841 A | 4/2008 |
| JP | 2008133207 A | 6/2008 |
| JP | 2008133218 A | 6/2008 |
| JP | 2008169121 A | 7/2008 |
| JP | 2009-508481 A | 3/2009 |
| JP | 2009067739 A | 4/2009 |
| JP | 2009114128 A | 5/2009 |
| JP | 2009126792 A | 6/2009 |
| JP | 2009137851 A | 6/2009 |
| WO | WO 89/11789 A1 | 12/1989 |
| WO | WO 95/34659 A1 | 12/1995 |
| WO | WO 95/34668 A2 | 12/1995 |
| WO | WO 96/005721 A1 | 2/1996 |
| WO | WO 96/033270 A1 | 10/1996 |
| WO | WO 96/038567 A2 | 12/1996 |
| WO | WO 96/040964 A2 | 12/1996 |
| WO | WO 97/49816 A1 | 12/1997 |
| WO | WO 99/024585 A1 | 5/1999 |
| WO | WO 99/26467 A1 | 6/1999 |
| WO | WO 99/27116 A2 | 6/1999 |
| WO | WO 99/32619 A1 | 7/1999 |
| WO | WO 99/61631 A1 | 12/1999 |
| WO | WO 99/67367 A1 | 12/1999 |
| WO | WO 00/32757 A2 | 6/2000 |
| WO | WO 00/044914 A1 | 8/2000 |
| WO | WO 01/07601 A2 | 2/2001 |
| WO | WO 2001/007601 A2 | 2/2001 |
| WO | WO 2001/085970 A2 | 11/2001 |
| WO | WO 02/14472 A2 | 2/2002 |
| WO | WO 02/066660 A2 | 8/2002 |
| WO | WO 03/000679 A2 | 1/2003 |
| WO | WO 03/006422 A1 | 1/2003 |
| WO | WO 2003/004649 | 1/2003 |
| WO | WO 03/012052 A2 | 2/2003 |
| WO | WO 03/013247 A1 | 2/2003 |
| WO | WO 03/016308 A1 | 2/2003 |
| WO | WO 2003/014357 A1 | 2/2003 |
| WO | WO 03/020704 A1 | 3/2003 |
| WO | WO 03/022051 A1 | 3/2003 |
| WO | WO 03/022831 A1 | 3/2003 |
| WO | WO 03/022843 A1 | 3/2003 |
| WO | WO 03/029243 A2 | 4/2003 |
| WO | WO 03/037085 A1 | 5/2003 |
| WO | WO 03/037878 A1 | 5/2003 |
| WO | WO 03/045878 A2 | 6/2003 |
| WO | WO 03/050087 A2 | 6/2003 |
| WO | WO 03/051823 A1 | 6/2003 |
| WO | WO 03/051824 A1 | 6/2003 |
| WO | WO 03/051846 A2 | 6/2003 |
| WO | WO 03/064625 A2 | 8/2003 |
| WO | WO 03/076409 A1 | 9/2003 |
| WO | WO 03/077648 A2 | 9/2003 |
| WO | WO 03/087067 A1 | 10/2003 |
| WO | WO 03/090539 A1 | 11/2003 |
| WO | WO 03/091217 A1 | 11/2003 |
| WO | WO 03/093269 A2 | 11/2003 |
| WO | WO 03/104206 A2 | 12/2003 |
| WO | WO 2004/002947 A1 | 1/2004 |
| WO | WO 2004/002981 A2 | 1/2004 |
| WO | WO 2004/005485 A2 | 1/2004 |
| WO | WO 2004/009761 A2 | 1/2004 |
| WO | WO 2004/011429 A1 | 2/2004 |

(56) References Cited

FOREIGN PATENT DOCUMENTS

| | | |
|---|---|---|
| WO | WO 2004/022771 A2 | 3/2004 |
| WO | WO 2004/029060 A1 | 4/2004 |
| WO | WO 2004/035545 A2 | 4/2004 |
| WO | WO 2004/035563 A1 | 4/2004 |
| WO | WO 2004/035564 A1 | 4/2004 |
| WO | WO 2004/037787 A1 | 5/2004 |
| WO | WO 2004/049806 A1 | 6/2004 |
| WO | WO 2004/062351 A2 | 7/2004 |
| WO | WO 2004/067518 A1 | 8/2004 |
| WO | WO 2004/067527 A1 | 8/2004 |
| WO | WO 2004/074443 A2 | 9/2004 |
| WO | WO 2004/077950 A1 | 9/2004 |
| WO | WO 2005/000824 A1 | 1/2005 |
| WO | WO 2005/003362 A2 | 1/2005 |
| WO | WO 2005/007627 A1 | 1/2005 |
| WO | WO 2005/007860 A1 | 1/2005 |
| WO | WO 2005/040152 A1 | 5/2005 |
| WO | WO 2005/047233 A1 | 5/2005 |
| WO | WO 2005/047281 A1 | 5/2005 |
| WO | WO 2005/061443 A2 | 7/2005 |
| WO | WO 2005/061464 A1 | 7/2005 |
| WO | WO 2005/068434 A1 | 7/2005 |
| WO | WO 2005/070889 A1 | 8/2005 |
| WO | WO 2005/089551 A1 | 9/2005 |
| WO | WO 2005/095335 A1 | 10/2005 |
| WO | WO 2005/107437 A2 | 11/2005 |
| WO | WO 2005/110068 A2 | 11/2005 |
| WO | WO 2006/006569 A1 | 1/2006 |
| WO | WO 2006/024820 A1 | 3/2006 |
| WO | WO 2006/029828 A1 | 3/2006 |
| WO | WO 2006/029829 A1 | 3/2006 |
| WO | WO 2006/037945 A1 | 4/2006 |
| WO | WO 2006/050803 A1 | 5/2006 |
| WO | WO 2006/074400 A2 | 7/2006 |
| WO | WO 2006/090792 A1 | 8/2006 |
| WO | WO 2006/123088 A2 | 11/2006 |
| WO | WO 2006/125687 A1 | 11/2006 |
| WO | WO 2006/125688 A1 | 11/2006 |
| WO | WO 2006/132270 A1 | 12/2006 |
| WO | WO 2006/138638 A1 | 12/2006 |
| WO | WO 2007/003294 A1 | 1/2007 |
| WO | WO 2007/007316 A1 | 1/2007 |
| WO | WO 2007/024783 | 3/2007 |
| WO | WO 2007/026834 A1 | 3/2007 |
| WO | WO 2007/035650 A2 | 3/2007 |
| WO | WO 2007/038788 A2 | 4/2007 |
| WO | WO 2007/039454 A1 | 4/2007 |
| WO | WO 2007/050715 A2 | 5/2007 |
| WO | WO 2007/051462 A2 | 5/2007 |
| WO | WO 2007/070389 A2 | 6/2007 |
| WO | WO 2007/071900 A1 | 6/2007 |
| WO | WO 2007/074405 A2 | 7/2007 |
| WO | WO 2007/077201 A1 | 7/2007 |
| WO | WO 2007/077247 A1 | 7/2007 |
| WO | WO 2007/080126 A2 | 7/2007 |
| WO | WO 2007/080127 A2 | 7/2007 |
| WO | WO 2007/083193 A2 | 7/2007 |
| WO | WO 2007/096576 A1 | 8/2007 |
| WO | WO 2007/051462 A3 | 10/2007 |
| WO | WO 2007/119434 A1 | 10/2007 |
| WO | WO 2007/134984 A1 | 11/2007 |
| WO | WO 2008/007100 A2 | 1/2008 |
| WO | WO 2008/009908 A1 | 1/2008 |
| WO | WO 2008/029084 A1 | 3/2008 |
| WO | WO 2008/042231 A2 | 4/2008 |
| WO | WO 2008/059948 A1 | 5/2008 |
| WO | WO 2008/063203 A2 | 5/2008 |
| WO | WO 2008/071918 A1 | 6/2008 |
| WO | WO 2008/074991 A1 | 6/2008 |
| WO | WO 2008/084073 A1 | 7/2008 |
| WO | WO 2008/100426 A2 | 8/2008 |
| WO | WO 2008/102908 AI | 8/2008 |
| WO | WO 2008/148223 A1 | 12/2008 |
| WO | WO 2008/152072 A2 | 12/2008 |
| WO | WO 2008/152073 A2 | 12/2008 |
| WO | WO 2009/000757 A1 | 12/2008 |
| WO | WO 2009/005297 A2 | 1/2009 |
| WO | WO 2009/029690 A1 | 3/2009 |
| WO | WO 2009/035150 A2 | 3/2009 |
| WO | WO 2009/037329 A2 | 3/2009 |
| WO | WO 2009/046384 A1 | 4/2009 |
| WO | WO 2009/063180 A1 | 5/2009 |
| WO | WO 2009/068170 A2 | 6/2009 |
| WO | WO 2009/068171 A2 | 6/2009 |
| WO | WO 2009/086041 A1 | 7/2009 |
| WO | WO 2009/090401 A2 | 7/2009 |
| WO | WO 2009/090402 A2 | 7/2009 |
| WO | WO 2009/115788 A1 | 9/2009 |
| WO | WO 2009/116558 A1 | 9/2009 |
| WO | WO 2009/125401 A2 | 10/2009 |
| WO | WO 2009/144079 A1 | 12/2009 |
| WO | WO 2009/152995 A1 | 12/2009 |
| WO | WO 2009/158258 A1 | 12/2009 |
| WO | WO 2010/012649 A1 | 2/2010 |
| WO | WO 2010/026989 A1 | 3/2010 |
| WO | WO 2010/034153 A1 | 4/2010 |
| WO | WO 2010/049270 A1 | 5/2010 |
| WO | WO 2010/049369 A1 | 5/2010 |
| WO | WO 2010/049405 A1 | 5/2010 |
| WO | WO 2010/049414 A1 | 5/2010 |
| WO | WO 2010/056519 A1 | 5/2010 |
| WO | WO 2010/063422 A1 | 6/2010 |
| WO | WO 2010/069802 A1 | 6/2010 |
| WO | WO 2010/078906 A2 | 7/2010 |
| WO | WO 2010/078912 A1 | 7/2010 |
| WO | WO 2010/093788 A2 | 8/2010 |
| WO | WO 2010/104217 A1 | 9/2010 |
| WO | WO 2010/108611 A1 | 9/2010 |
| WO | WO 2010/112826 A2 | 10/2010 |
| WO | WO 2010/116122 A2 | 10/2010 |
| WO | WO 2010/119906 A1 | 10/2010 |
| WO | WO 2010/130970 A1 | 11/2010 |
| WO | WO 2011/001434 A1 | 1/2011 |
| WO | WO 2011/003776 A2 | 1/2011 |
| WO | WO 2011/035874 A1 | 3/2011 |
| WO | WO 2011/045796 A1 | 4/2011 |
| WO | WO 2011/065451 A1 | 6/2011 |
| WO | WO 2011/067745 A2 | 6/2011 |
| WO | WO 2011/075188 A1 | 6/2011 |
| WO | WO 2011/080674 A2 | 7/2011 |
| WO | WO 2011/112570 A1 | 9/2011 |
| WO | WO 2011/132127 A1 | 10/2011 |
| WO | WO 2012/001626 A1 | 1/2012 |
| WO | WO 2012/056401 A1 | 5/2012 |
| WO | WO 2012/092580 A2 | 7/2012 |
| WO | WO 2012/164100 A2 | 12/2012 |
| WO | WO 2013/010691 A1 | 1/2013 |
| WO | WO 2013/025670 A2 | 2/2013 |
| WO | WO 2013/039990 A1 | 3/2013 |
| WO | WO 2013/040005 A1 | 3/2013 |
| WO | WO 2013/040021 A1 | 3/2013 |
| WO | WO 2013/040033 A1 | 3/2013 |
| WO | WO 2013/040049 A1 | 3/2013 |
| WO | WO 2013/040057 A1 | 3/2013 |
| WO | WO 2013/040116 A9 | 3/2013 |
| WO | WO 2013/040117 A9 | 3/2013 |
| WO | WO 2013/153553 A2 | 10/2013 |
| WO | WO 2013/175480 A1 | 11/2013 |
| WO | WO 2014/022739 A2 | 2/2014 |
| WO | WO 2014/106837 A2 | 7/2014 |
| WO | WO 2014/106838 A2 | 7/2014 |
| WO | WO 2014/151255 A1 | 9/2014 |
| WO | WO 2014/164761 A1 | 10/2014 |
| WO | WO 2014/164797 A2 | 10/2014 |
| WO | WO 2015/010026 A2 | 1/2015 |

OTHER PUBLICATIONS

5'-leader responsible for enhancing translation, Nucleic Acids Res., 20(17):4631-4638 (1992).
Agricultural Chemical Usage 2006 Vegetables Summary, Agricultural Statistics Board, NASS, USDA, pp. 1-372 (2007).
Agrios, Plant Pathology (Second Edition), 2:466-470 (1978).

(56) References Cited

OTHER PUBLICATIONS

Alarcón-Reverte et al., "Resistance to ACCase-inhibiting herbicides in the weed *Lolium multiflorum*," Comm. Appl. Biol. Sci., 73(4):899-902 (2008).
Al-Kaff et al,, "Plants rendered herbicide-susceptible by cauliflower mosaic virus—elicited suppression of a 35S promoter-regulated transgene," Nature Biotechnology, 18:995-999 (2000).
Amarzguioui et al., "An algorithm for selection of functional siRNA sequences," Biochemical and Biophysical Research Communications, 316:1050-1058 (2004).
Ambrus et al., "The Diverse Roles of RNA Helicases in RNAi," Cell Cycle, 8(21):3500-3505 (2009).
An et al., "Transient RNAi Induction against Endogenous Genes in *Arabidopsis* Protoplasts Using in Vitro-Prepared Double-Stranded RNA," Biosci Biotechnol Biochem, 69(2):415-418 (2005).
Andersen et al., "Delivery of siRNA from lyophilized polymeric surfaces," Biomaterials, 29:506-512 (2008).
Andersson et al., "A novel selection system for potato transformation using a mutated AHAS gene," Plant Cell Reports, 22(4):261-267 (2003).
Anonymous, "Resistant Weeds Spur Research Into New Technologies," Grains Research & Development Corporation, 2013.
Anonymous, "A handbook for high-level expression and purification of 6xHis-tagged proteins," The QiaExpressionist, (2003).
Anonymous, "Agronomy Facts 37: Adjuvants for enhancing herbicide performance," n.p., 1-8, (Jan. 26, 2000), Web, (Jan. 21, 2014).
Anonymous, "Devgen, The mini-Monsanto," KBC Securities (2006).
Anonymous, "Do Monsanto have the next big thing?," Austalian Herbicide Resistance Initiative (AHRI), (Apr. 23, 2014) Web. (Jan. 19, 2015).
Aoki et al., "In Vivo Transfer Efficiency of Antisense Oligonucleotides into the Myocardium Using HVJ-Liposome Method," Biochem Biophys Res Commun, 231:540-545 (1997).
Arpaia et al., "Production of transgenic eggplant (*Solanum melongena* L.) resistant to Colorado Potato Beetle (*Leptinotarsa decemlineata* Say)," (1997) Theor. Appl. Genet., 95:329-334 (1997).
Artymovich, "Using RNA interference to increase crop yield and decrease pest damage," MMG 445 Basic Biotech., 5(1):7-12 (2009).
Ascencio-Ibanez et al., "DNA abrasion onto plants is an effective method for geminivirus infection and virus-induced gene silencing," Journal of Virological Methods, 142:198-203 (2007).
Axtell et al., "A Two-Hit Trigger for siRNA Biogenesis in Plants," Cell, 127:565-577 (2006).
Bachman et al., "Characterization of the spectrum of insecticidal activity of a double-stranded RNA with targeted activity against Western Corn Rootworm (*Diabrotica virgifera virgifera* LeConte)," Transgenic Res., pp. 1-16 (2013).
Baerson et al., "Glyphosate-Resistant Goosegrass. Identification of a Mutation in the Target Enzyme 5-Enolpyruvylshikimate-3-Phosphate Synthase," Plant Physiol., 129(3):1265-1275 (2002).
Bai et al., "Naturally Occurring Broad-Spectrum Powdery Mildew Resistance in a Central American Tomato Accession Is Caused by Loss of Mlo Function," MPMI, 21(1):30-39 (2008).
Balibrea et al., "Extracellular Invertase is an Essential Component of Cytokinin-Mediated Delay of Senescence," The Plant Cell, 16(5):1276-1287 (2004).
Bannerjee et al., "Efficient production of transgenic potato (*S. tuberosum* L. ssp. *andigena*) plants via Agrobacterium tumefaciens-mediated transformation," Plant Sci., 170:732 738 (2006).
Bart et al., "A novel system for gene silencing using siRNAs in rice leaf and stem-derived protoplasts," Plant Methods, 2(13):1-9 (2006).
Basu et al., "Weed genomics: new tools to understand weed biology," TRENDS in Plant Science, 9(8):391-398 (2004).
Baulcombe, "RNA silencing and heritable epigenetic effects in tomato and *Arabidopsis*," Abstract 13th Annual Fall Symposium, Plant Genomes to Phenomes, Donald Danforth Plant Science Center, 28-30 (2011).
Bayer et al., "Programmable ligand-controlled riboregulators of eukaryotic gene expression," Nature Biotechnol., 23(3):337-343 (2005).
Beal, et al., "Second Structural Motif for Recognition of DNA by Oligonucleotide-Directed Triple-Helix Formation," Science, 251:1360-1363 (1992).
Becker et al., "Fertile transgenic wheat from microprojectile bombardment of scutellar tissue," The Plant Journal, 5(2):299-307 (1994).
Bedell et al., "Sorghum Genome Sequencing by Methylation Filtration," Plos Biology, 3(1):E13/104-115 (2005).
Bhargava et al., "Long double-stranded RNA-mediated RNA interference as a tool to achieve site-specific silencing of hypothalamic neuropeptides," Brain Research Protocols, 13:115-125 (2004).
Boletta et al., "High Efficient Non-Viral Gene Delivery to the Rat Kidney by Novel Polycationic Vectors," J. Am Soc. Nephrol., 7:1728 (1996).
Bolognesi et al., "Characterizing the Mechanism of Action of Double-Stranded RNA Activity against Western Corn Rootworm(*Diabrotica virgifera virgifera* LeConte)," PLoS ONE 7(10):e47534 (2012).
Bolter et al., "A chloroplastic inner envelope membrane protease is essential for plant development," FEBS Letters, 580:789-794 (2006).
Bourgeois et al., "Field and producer survey of ACCase resistant wild oat in Manitoba," Canadian Journal of Plant Science, 709-715 (1997).
Breaker et al., "A DNA enzyme with $Mg^{2+}$-dependent RNA phosphoesterase activity," Chemistry and Biology, 2:655-660 (1995).
Brodersen et al., "The diversity of RNA silencing pathways in plants," Trends in Genetics, 22(5):268-280 (2006).
Brugière et al., "Glutamine Synthetase in the Phloem Plays a Major Role in Controlling Proline Production," The Plant Cell, 11:1995-2011 (1999).
Burgos et al., "Review: Confirmation of Resistance to Herbicides and Evaluation of Resistance Levels," Weed Science, 61(1):4-20 (2013).
Busch et al., "RNAi for discovery of novel crop protection products," Pflanzenschutz-Nachrichten Bayer, 58(1):34-50 (2005)
Busi et al., "Gene flow increases the initial frequency of herbicide resistance alleles in unselectedpopulations," Agriculture, Ecosystems and Environments, Elsevier, Amsterdam, NL, 142(3):403-409 (2011).
Butler et al., "Priming and re-drying improve the survival of mature seeds of Digitalis purpurea during storage," Annals of Botany, 103:1261-1270 (2009).
Bytebier et al., "T-DNA organization in tumor cultures and transgenic plants of the monocotyledon Asparagus officinalis," Proc. Natl. Acad. Sci. U.S.A., 84:5345-5349 (1987).
Campbell et al., "Gene-knockdown in the honey bee mite Varroa destructor by a non-invasive approach: studies on a glutathione S-transferase," Parasites & Vectors, 3(1):73, pp. 1-10 (2010).
Chabannes et al., "In situ analysis of lignins in transgenic tobacco reveals a differential impact of individual transformations on the spatial patterns of lignin deposition at the cellular and subcellular levels," The Plant Journal, 28(3):271-282 (2001).
Chabbouh et al., "Cucumber mosaic virus in artichoke," FAO Plant Protection Bulletin, 38:52-53 (1990).
Chakravarty et al., "Genetic Transformation in Potato: Approaches and Strategies," Amer J Potato Res, 84:301 311 (2007).
Chang et al., "Cellular Internalization of Fluorescent Proteins via Arginine-rich Intracellular Delivery Peptide in Plant Cells," Plant Cell Physiol., 46(3):482-488 (2005).
Chee et al., "Transformation of Soybean (*Glycine max*) by Infecting Germinating Seeds with Agrobacterium tumefaciens," Plant Physiol., 91:1212-1218 (1989).
Chen et al., "Exploring MicroRNA-Like Small RNAs in the Filamentous Fungus *Fusarium oxysporum*," PLOS One, 9(8):e104956:1-10 (2014).
Chen et al., "In Vivo Analysis of the Role of atTic20 in Protein Import into Chloroplasts," The Plant Cell, 14:641-654 (2002).
Chen et al., "Transfection and Expression of Plasmid DNA in Plant Cells by an Arginine-Rich Intracellular Delivery Peptide without Protoplast Preparation," FEBS Letters 581, pp. 1891-1897 (2007).
Cheng et al., "Production of fertile transgenic peanut (*Arachis hypogaea* L.) plants using Agrobacterium tumefaciens," Plant Cell Reports, 15:653-657 (1996).

(56) References Cited

OTHER PUBLICATIONS

Chi et al., "The Function of RH22, a Dead RNA Helicase, in the Biogenesis of the 50S Ribosomal Subunits of *Arabidopsis* Chloroplasts," Plant Physiology, 158:693-707 (2012).
Chupp et al., "Chapter 8: White Rust," Vegetable Diseases and Their Control, The Ronald Press Company, New York, pp. 267-269 (1960).
Clough et al., "Floral dip: a simplified method for Agrobacterium-mediated transformation of *Arabidopsis thaliana*," The Plant Journal, 16(6):735-743 (1998).
CN101914540 Patent Diclosure, "Introduction of RNA into plant by interference," (2010).
Colbourne et al., "The Ecoresponsive Genome of Daphnia pulex," Science, 331(6017):555-561 (2011).
Colliver et al., "Differential modification of flavonoid and isoflavonoid biosynthesis with an antisense chalcone synthase construct in transgenic Lotus corniculatus," Plant Molecular Biology, 35:509-522 (1997).
Communication pursuant to Article 94(3) EPC dated Jan. 14, 2016, in European Patent Application No. 12 832 415.9.
Communication pursuant to Article 94(3) EPC dated Jun. 26, 2015, in European Patent Application No. 11 753 916.3.
Communication pursuant to Article 94(3) EPC dated Mar. 18, 2016, in European Patent Application No. 12 832 160.1.
Communication pursuant to Article 94(3) EPC dated Mar. 24, 2016, in European Patent Application No. 12 831 684.1.
Communication pursuant to Article 94(3) EPC dated Mar. 4, 2016, in European Patent Application No. 12 830 932.5.
Communication pursuant to Article 94(3) EPC dated Mar. 9, 2016, in European Patent Application No. 12 831 166.9.
Communication pursuant to Article 94(3) EPC dated Oct. 23, 2015, in European Patent Application No. 12 831 945.6.
Concise Descriptions of Relevance filed by a third party on Nov. 29, 2012, in U.S. Appl. No. 13/042,856.
Constan et al., "An outer envelope membrane component of the plastid protein import apparatus plays an essential role in *Arabidopsis*," The Plant Journal, 38:93-106 (2004).
Cooney et al., "Site-Specific Oligonucleotide Binding Represses Transcription of the Human c-myc Gene in Vitro," Science, 241:456-459 (1988).
COST Action FA0806 progress report "Plant virus control employing RNA-based vaccines: A novel non-transgenic strategy" (2010).
Coticchia et al., "Calmodulin modulates Akt activity in human breast cancer cell lines," Breast Cancer Res. Treat, 115:545-560 (2009).
Dalakouras et al., "Induction of Silencing in Plants by High-Pressure Spraying of In vitro-Synthesized Small RNAs," Frontiers in Plant Science, 7(1327):1-5 (2016).
Dalmay et al., "An RNA-Depenedent RNA Polymerase Gene in *Arabidopsis* is Required for Posttranscriptional Gene Silencing Mediated by a Transgene but Not by a Virus," Cell, 101:543-553 (2000).
Davidson et al., "Engineering regulatory RNAs," TRENDS in Biotechnology, 23(3):109-112 (2005).
Dawson et al., "cDNA cloning of the complete genome of tobacco mosaic virus and production of infectious transcripts," Proc. Natl. Acad. Sci. USA, 83:1832-1836 (1986).
De Block, et al. "Engineering herbicide resistance in plants by expression of a detoxifying enzyme," EMBO J. 6(9):2513-2519 (1987).
De Framond, "MINI-Ti: A New Vector Strategy for Plant Genetic Engineering," Nature Biotechnology, 1:262-269 (1983).
Della-Cioppa et al., "Import of a precursor protein into chloroplasts is inhibited by the herbicide glyphosate," The EMBO Journal, 7(5):1299-1305 (1988).
Desai et al., "Reduction in deformed wing virus infection in larval and adult honey bees (*Apis mellifera* L.) by double-stranded RNA ingestion," Insect Molecular Biology, 21(4):446-455 (2012).

Di Stilio et al., "Virus-Induced Gene Silencing as a Tool for Comparative Functional Studies in Thalictrum," PLoS One, 5(8):e12064 (2010).
Diallo et al., "Long Endogenous dsRNAs Can Induce Complete Gene Silencing in Mammalian Cells and Primary Cultures," Oligonucleotides, 13:381-392 (2003).
Dietemann et al., "Varroa destructor: research avenues towards sustainable control," Journal of Apicultural Research, 51(1):125-132 (2012).
Du et al., "A systematic analysis of the silencing effects of an active siRNA at all single-nucleotide mismatched target sites," Nucleic Acids Research, 33(5):1671-1677 (2005).
Dunoyer et al., "Small RNA Duplexes Function as Mobile Silencing Signals Between Plant Cells," Science, 328:912-916 (2010).
Eamens et al., "RNA Silencing in Plants: Yesterday, Today, and Tomorrow," Plant Physiology, 147(2):456-468 (2008).
Ellington et al., "In vitro selection of RNA molecules that bind specific ligands," Nature, 346:818-822 (1990).
Emery et al., "Radial Patterning of *Arabidopsis* Shoots by Class III HD-ZIP and KANADI Genes," Current Biology, 13:1768-1774 (2003).
Eudes et al., "Cell-penetrating peptides," Plant Signaling & Behavior, 3(8):549-5550 (2008).
European Cooperation in the field of Scientific and Technical Research—Memorandum of Understanding for COST Action FA0806 (2008).
European Search Report dated Sep. 7, 2017, in European Patent Application No. 17152830.0.
Extended European Search Report dated Feb. 2, 2015, in European Patent Application No. 12 830 932.5.
Extended European Search Report dated Feb. 27, 2015, in European Patent Application No. 12 832 160.1.
Extended European Search Report dated Feb. 3, 2015, in European Patent Application No. 12 831 945.6.
Extended European Search Report dated Jan. 20, 2016, in European Patent Application No. 13 794 339.5.
Extended European Search Report dated Jan. 21, 2015, in European Patent Application No. 12 832 415.9.
Extended European Search Report dated Jan. 29, 2015, in European Patent Application No. 12 831 567.8.
Extended European Search Report dated Jun. 29, 2015, in European Patent Application No. 12 831 494.5.
Extended European Search Report dated Mar. 17, 2015, in European Patent Application No. 12 831 684.1.
Extended European Search Report dated Mar. 3, 2015, in European Patent Application No. 12 831 166.9.
Extended European Search Report dated Nov. 7, 2017, in European Patent Application No. 15811092.4.
Extended European Search Report dated Nov. 8, 2017, in European Patent Application No. 15737282.2.
Extended European Search Report dated Oct. 8, 2013, in European Patent Application No. 11753916.3.
Extended European Search Report dated Sep. 29, 2016, in European Patent Application No. 14778840.0.
Farooq et al., "Rice seed priming," IRPN, 30(2):45-48 (2005).
Fassler, BLAST Glossary, National Center for Biotechnology Information (2011).
Fernandez et al., "Uptake of Hydrophilic Solutes Through Plant Leaves: Current State of Knowledge and Perspectives of Foliar Fertilization," Critical Reviews in Plant Sciences, 28:36-38 (2009).
Feuillet et al., "Crop genome sequencing: lessons and rationales," Trends Plant Sci., 16:77-88 (2011).
Final Office Action dated Apr. 7, 2016, in U.S. Appl. No. 13/619,980.
Final Office Action dated Dec. 17, 2015, in U.S. Appl. No. 14/335,135.
Final Office Action dated Feb. 17, 2016, in U.S. Appl. No. 13/612,929.
Final Office Action dated Feb. 4, 2016, in U.S. Appl. No. 13/612,936.
Final Office Action dated Jun. 30, 2016, in U.S. Appl. No. 13/901,326.
Final Office Action dated Mar. 2, 2016, in U.S. Appl. No. 13/612,995.
Final Office Action dated Mar. 21, 2016, in U.S. Appl. No. 13/612,925.
Final Office Action dated May 26, 2016, in U.S. Appl. No. 14/532,596.
Final Office Action dated Nov. 10, 2015, in U.S. Appl. No. 13/612,985.
Final Office Action dated Nov. 10, 2016, in U.S. Appl. No. 13/583,302.
Final Office Action dated Nov. 19, 2015, in U.S. Appl. No. 13/612,941.

(56) References Cited

OTHER PUBLICATIONS

Final Office Action dated Nov. 30, 2015, in U.S. Appl. No. 13/612,948.
Final Office Action dated Nov. 7, 2013, in U.S. Appl. No. 13/042,856.
Final Office Action dated Oct. 20, 2016, in U.S. Appl. No. 14/480,199.
Final Office Action dated Oct. 22, 2015, in U.S. Appl. No. 14/608,951.
Final Office Action dated Sep. 9, 2016, in U.S. Appl. No. 13/612,954.
Final Office Action dated Sep. 9, 2016, in U.S. Appl. No. 14/603,347.
Final Office Action dated Sep. 9, 2016, in U.S. Appl. No. 14/608,951.
Fire et al., "Potent and specific genetic interference by double-stranded RNA in Caenorhabditis elegans," Nature, 391:806-811 (1998).
First Examination Report dated Apr. 23, 2013, in New Zealand Patent Application No. 601784.
First Examination Report dated Jul. 28, 2014, in New Zealand Patent Application No. 627060.
First Office Action dated Aug. 31, 2015, in Chinese Patent Application No. 201280053985.3.
First Office Action dated Feb. 2, 2016, in Chinese Patent Application No. 201380039346.6.
First Office Action dated Jul. 7, 2015, in Chinese Patent Application No. 201280054820.8.
First Office Action dated Mar. 12, 2015, in Chinese Patent Application No. 201280053984.9.
First Office Action dated Mar. 2, 2015, in Chinese Patent Application No. 201280054819.5.
First Office Action dated May 27, 2015, in Chinese Patent Application No. 201280054179.8.
First Office Action dated Sep. 9, 2015, in Chinese Patent Application No. 201280055409.2.
Fraley et al., "Liposome-mediated delivery of tobacco mosaic virus RNA into tobacco protoplasts: A sensitive assay for monitoring liposome-protoplast interactions," Proc Natl Acad Sci U S A., 79(6):1859-1863 (1982).
Friedberg, "Automated protein function prediction—the genomic challenge," Briefings in Bioinformatics, 7(3):225-242 (2006).
Fukuhara et al., "Enigmatic Double-Stranded RNA in Japonica Rice," Plant Molecular Biology, 21:1121-1130 (1993).
Fukuhara et al., "The Unusual Structure of a Novel RNA Replicon in Rice," The Journal of Biological Chemistry, 270(30):18147-18149 (1995).
Fukuhara et al., "The wide distribution of endornaviruses, large double-stranded RNA replicons with plasmid-like properties," Archives of Virology, 151:995-1002 (2006).
Fukunaga et al., "dsRNA with 5' overhangs v contributes to endogenous and antiviral RNA silencing pathways in plants," The EMBO Journal, 28(5):545-555 (2009).
Funke et al., "Molecular basis for herbicide resistance in Roundup Ready crops," PNAS, 103:13010-13015 (2006).
Further Examination Report dated May 16, 2014, in New Zealand Patent Application No. 601784.
Gaines et al., "Gene amplification confers glyphosate resistance in Amaranthus palmeri," Proc. Natl. Acad. Sci. USA, 107(3):1029-1034 (2010).
Gallie et al., Identification of the motifs within the tobacco mosaic virus.
Gan et al., "Bacterially expressed dsRNA protects maize against SCMV infection," Plant Cell Rep, 29(11):1261-1268 (2010).
Gan et al., "Inhibition of Leaf Senescence by Autoregulated Production of Cytokinin," Science, 270:1986-1988 (1995).
Gao et al., "Down-regulation of acetolactate synthase compromises 01-1-mediated resistance to powdery mildew in tomato," BMC Plant Biology, 14 (2014).
Gao et al., "Nonviral Methods for siRNA Delivery," Molecular Pharmaceutics, 6(3):651-658 (2008).
Garbian et al., "Bidirectional Transfer of RNAi between Honey Bee and Varroa destructor: Varroa Gene Silencing Reduces Varroa Population," 8(12):1-9:e1003035 (2012).
Gaskin et al., "Novel organosillicone adjuvants to reduce agrochemical spray volumes on row crops," New Zealand Plant Protection, 53:350-354 (2000).
Ge et al., "Rapid vacuolar sequestration: the horseweed glyphosate resistance mechanism," Pest Management Sci., 66:345-348 (2010).
GenBank Accession No. AY545657.1 (2004).
GenBank Accession No. CB377464, "CmaE1_37_J02_T3 Cowpea weevil larvae Lambda Zap Express Library Callosobruchus maculatus cDNA, mRNA sequence," (2007).
GenBank Accession No. DY640489, "PU2_plate27_F03 PU2 Prunus persica cDNA similar to expressed mRNA inferred from Prunus persica hypothetical domain/motif containing IPR011005:Dihydropteroate synthase-like, MRNA sequence" (2006).
GenBank Accession No. EF143582 (2007).
GenBank Accession No. EU024568, "Amaranthus hypochondriacus acetolactate synthase (ALS) gene" (2007).
GenBank Accession No. EW765249, "ST020010B10C12 Normalized and subtracted western corn rootworm female head cDNA library Diabrotica virgifera virgifera cDNA clone STO20010BI0C12 5-, mRNA sequence," (2007).
GenBank Accession No. EW771198, "ST020010B10C12 Normalized and subtracted western corn rootworm female head cDNA library Diabrotica virgifera virgifera cDNA clone STO20010B10C12 5-, mRNA sequence," (2007).
GenBank Accession No. FE348695, "CBIB7954.fwd CBIB_Daphnia_pulex_Chosen_One_Library_2 Daphnia pulex cDNA clone CBIB7954 5', mRNA sequence" (2011).
GenBank Accession No. FJ972198, "Solanum lycopersicum cultivar Ailsa Craig dihydropterin pyrophosphokinase-dihydropteroate synthase (HPPK-DHPS) gene, complete cds" (2010).
GenBank Accession No. GI:186478573 (2014).
GenBank Accession No. GU120406, "Chrysomela tremulae ribosomal protein L7 (RpL7) mRNA, complete cds" (2009).
GenBank Accession No. HD315444, "Sequence 192160 from Patent EP2213738" (2010).
GenBank Accession No. Q4GXM3_BIPLU, "Ribosomal protein L7e" (2006).
GenBank Accession No. U87257.1, "Daucus carota 4-hydroxyphenylpyruvate dioxygenase mRNA, complete cds" (1997).
GenBank Accession No. XM_014456745.1, Predicted: Myotis lucifugus ribonucleoprotein, PTB-binding 2 (RAVER2), transcript variant X3, mRNA,: (2015).
GenBank Accession No. Y08611.1, "P.sativum mRNA for dihydropterin pyrophosphokinase/dihydropteroate synthase." (2006).
GenEmbl Accession No. FJ861243 (2010).
Gong et al., "Silencing of Rieske iron-sulfur protein using chemically synthesised siRNA as a potential biopesticide against Plutella xylostella," Pest Manag Sci, 67:514-520 (2011).
Gossamer Threads, Compendium of Herbicide Adjuvants: Organo-Silicone Surfactant, p. 1-4 (1998).
Gressel et al., "A strategy to provide long-term control of weedy rice while mitigating herbicide resistance transgene flow, and its potential use for other crops with related weeds," Pest Manag Sci, 65(7):723-731 (2009).
Gudkov, "Minireview: The L7/L12 ribosomal domain of the ribosome: structural and functional studies," FEBS Letters, 407:253-256 (1997).
Gutensohn et al., "Functional analysis of the two Arabidopsis homologues of Toc34, a component of the chloroplast protein import apparatus," The Plant Journal, 23(6):771-783 (2000).
Hagio, "Chapter 25: Direct Gene Transfer into Plant Mature Seeds via Electroporation After Vacuum Treatment," Electroporation and Sonoporation in Developmental Biology, p. 285-293 (2009).
Haigh, "The Priming of Seeds: Investigation into a method of priming large quantities of seeds using salt solutions," Thesis submitted to Macquarie University (1983).
Hajirezaei et al., "Impact of elevated cytosolic and apoplastic invertase activity on carbon metabolism during potato tuber development," Journal of Experimental Botany, 51:439-445 (2000).
Hamilton et al "Guidelines for the Identification and Characterization of Plant Viruses," J. gen. Virol., 54:223-241 (1981).
Hamilton et al., "Two classes of short interfering RNA in RNA silencing," EMBO J., 21(17):4671-4679 (2002).
Han et al., "Molecular Basis for the Recognition of Primary microRNAs by the Drosha-DGCR8 Complex," Cell, 125(5):887-901 (2006).

(56) References Cited

OTHER PUBLICATIONS

Hannon, "RNA interference," Nature,481:244-251 (2002).
Hardegree, "Drying and storage effects on germination of primed grass seeds," Journal of Range Management, 47(3):196-199 (1994).
Harrison et al., "Does Lowering Glutamine Synthetase Activity in Nodules Modigy Nitrogen Metabolism and Growth of Lotus japonicus?," Plant Physiology, 133:253-262 (2003).
Heffer et al., "Rapid isolation of gene homologs across taxa: Efficient identification and isolation of gene orthologs from non-model organism genomes, a technical report," EvoDevo Journal, 2(7):1-5 (2011).
Herman et al., "A three-component dicamba O-demethylase from Pseudomonas maltophilia, strain DI-6: gene isolation, characterization, and heterologous expression," J. Biol. Chem., 280: 24759-24767 (2005).
Hess, "Surfactants and Additives," 1999 Proceedings of the California Weed Science Society, 51:156-172 (1999).
Hewezi et al., "Local infiltration of high- and low-molecular-weight RNA from silenced sunflower (*Helianthus annuus* L.) plants triggers post-transcriptional gene silencing in non-silenced plants," Plant Biotechnology Journal, 3:81-89 (2005).
Hidayat et al., "Enhanced Metabolism of Fluazifop Acid in a Biotype of Digitaria sanguinalis Resistant to the Herbicide Fluazifop-P-Butyl," Pesticide Biochem. Physiol., 57:137-146 (1997).
Himber et al., "Transitivity-dependant and -independent cell-to-cell movement of RNA silencing," The EMBO Journal, 22(17):4523-4533 (2003).
Hirschberg et al., "Molecular Basis of Herbicide Resistance in Amaranthus hybridus," Science, 222:1346-1349 (1983).
Hoekema et al., "A binary plant vector strategy based on separation of vir- and T-region of the Agrobacterium tumefaciens Ti-plasmid," Nature, 303:179-180 (1983).
Hofgen et al., "Repression of Acetolactate Synthase Activity through Antisense Inhibition: Molecular and Biochemical Analysis of Transgenic Potato (*Solanum tuberosum* L. cv *Desiree*) Plants," Plant Physiol., 107(2):469-477 (1995).
Holtra et al., "Assessment of the Physiological Condition of *Salvinia natans* L. Exposed to Copper(II) Ions," Environ. Protect. Eng., 41:147-158 (2015).
Hsieh et al., "A library of siRNA duplexes targeting the phosphoinositide 3-kinase pathway: determinants of gene silencing for use in cell-based screens," Nucleic Acids Res., 32(3):893-901 (2004).
Huang et al., "In Vivo Analyses of the Roles of Essential Omp85-Related Proteins in the Chloroplast Outer Envelope Membrane," Plant Physiol., 157:147-159 (2011).
Huesken et al., "Design of a genome-wide siRNA library using an artificial neural network," Nature Biotechnology, 23(8): 995-1001 (2005).
Hunter et al., "RNA Interference Strategy to suppress Psyllids & Leafhoppers," International Plant and Animal Genome XIX, 15-19 (2011).
Ichihara et al., "Thermodynamic instability of siRNA duplex is a prerequisite for dependable prediction of siRNA activities," Nucleic Acids Res., 35(18):e123 (2007).
International Preliminary Report on Patentability (Chapter II) dated Jul. 24, 2015, in International Application No. PCT/US2014/047204.
International Preliminary Report on Patentability dated Sep. 11, 2012, in International Application No. PCT/US2011/027528.
International Preliminary Report on Patentability dated Sep. 11, 2014, in International Application No. PCT/IL2013/050447.
International Rice Genome Sequencing Project, The map-based sequence of the rice genome, Nature, 436(11):793-800 (2005).
International Search Report and the Written Opinion dated Feb. 25, 2013, in International Application No. PCT/US2012/054883.
International Search Report and the Written Opinion dated Feb. 27, 2013, in International Application No. PCT/US2012/054814.
International Search Report and the Written Opinion dated Feb. 27, 2013, in International Application No. PCT/US2012/054842.
International Search Report and the Written Opinion dated Feb. 27, 2013, in International Application No. PCT/US2012/054862.
International Search Report and the Written Opinion dated Feb. 27, 2013, in International Application No. PCT/US2012/054894.
International Search Report and the Written Opinion dated Feb. 27, 2013, in International Application No. PCT/US2012/054974.
International Search Report and the Written Opinion dated Feb. 27, 2013, in International Application No. PCT/US2012/054980.
International Search Report and Written Opinion dated Jul. 8, 2015, in International Application No. PCT/US2015/011408.
International Search Report and the Written Opinion dated Jul. 15, 2014, in International Application No. PCT/US2014/025305.
International Search Report and the Written Opinion dated Jul. 22, 2014, in International Application No. PCT/IL2013/051083.
International Search Report and the Written Opinion dated Jul. 22, 2014, in International Application No. PCT/IL2013/051085.
International Search Report and the Written Opinion dated Jul. 24, 2014, in International Application No. PCT/US2014/026036.
International Search Report and the Written Opinion dated May 10, 2011, in International Application No. PCT/US2011/027528.
International Search Report and the Written Opinion dated Oct. 1, 2013, in International Application No. PCT/IL2013/050447.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Feb. 23, 2015, in International Application No. PCT/US2014/063832.
International Search Report and Written Opinion dated Mar. 26, 2015, in International Application No. PCT/US2014/069353.
International Search Report and Written Opinion dated May 26, 2016, in International Application No. PCT/US2016/014344.
International Search Report and Written Opinion dated Nov. 24, 2015, in International Application No. PCT/US2015/037522.
International Search Report and Written Opinion dated Nov. 27, 2015, in International Application No. PCT/US2015/037015.
International Search Report dated Mar. 12, 2013, in International Application No. PCT/US2012/054789.
Invitation to Pay Additional Fees dated May 6, 2014, in International Application No. PCT/IL2013/051083.
Invitation to Pay Additional Fees dated May 6, 2014, in International Application No. PCT/IL2013/051085.
Invitation to Pay Additional Fees dated Nov. 25, 2014, in International Application No. PCT/US2014/047204.
Invitation to Pay Additional Fees dated Sep. 8, 2015, in International Application No. PCT/US2015/037015.
Invitation to Pay Additional Fees dated Sep. 9, 2015, in International Application No. PCT/US2015/037522.
Isaacs et al., "Engineered riboregulators enable post-transcriptional control of gene expression," Nature Biotechnology, 22(7):841-847 (2004).
Ivanova et al., "Members of the Toc159 Import Receptor Family Represent Distinct Pathways for Protein Targeting to Plastids," Molecular Biology of the Cell, 15:3379-3392 (2004).
Jacque et al., "Modulation of HIV-1 replication by RNA interference," Nature, 418, 435-438 (2002).
Jang et al., "Resistance to herbicides caused by single amino acid mutations in acetyl-CoA carboxylase in resistant populations of grassy weeds," New Phytologist, 197(4):1110-1116 (2013).
Ji et al., "Regulation of small RNA stability: methylation and beyond," Cell Research, 22:624-636 (2012).
Jin et al., "Posttranslational Elevation of Cell Wall Invertase Activity by Silencing its Inhibitor in Tomato Delays Leaf Senescence and Increases Seed Weight and Fruit Hexose Level," The Plant Cell, 21:2072-2089 (2009).
Jofre-Garfias et al., "Agrobacterium-mediated transformation of Amaranthus hypochondriacus: light- and tissue-specific expression of a pea chlorophyll a/b-binding protein promoter," Plant Cell Reports, 16:847-852 (1997).
Jones-Rhoades et al., "MicroRNAs and Their Regulatory Roles in Plants," Annu. Rev. Plant Biol., 57:19-53 (2006).

(56) References Cited

OTHER PUBLICATIONS

Josse et al., "A DELLA in Disguise: SPATULA Restrains the Growth of the Developing Arabidopsis Seedling," Plant Cell, 23:1337-1351 (2011).
Kaloumenos et al., "Identification of a Johnsongrass (*Sorghum halepense*) Biotype Resistant to ACCase-Inhibiting Herbicides in Northern Greece," Weed Technol, 23:470-476 (2009).
Kam et al., "Nanotube Molecular Transporters: Internalization of Carbon Nanotube—Protein Conjugates into Mammalian Cells," J. Am. Chem. Soc., 126(22):6850-6851 (2004).
Kambiranda et al., "Relationship Between Acid Invertase Activity and Sugar Content in Grape Species," Journal of Food Biochemistry, 35:1646-1652 (2011).
Katoh et al., "Specific residues at every third position of siRNA shape its efficient RNAi activity," Nucleic Acids Res., 35(4): e27 (2007).
Kertbundit et al., "In vivo random β-glucuronidase gene fusions in *Arabidopsis thaliana*," Proc. Natl. Acad. Sci. U S A., 88:5212-5216 (1991).
Khachigian, "DNAzymes: Cutting a path to a new class of therapeutics," Curr Opin Mol Ther 4(2):119-121 (2002).
Khan et al., "Matriconditioning of Vegetable Seeds to Improve Stand Establishment in Early Field Plantings," J. Amer. Soc. Hort. Sci., 117(1):41-47 (1992).
Khodakovskaya et al., "Carbon Nanotubes Are Able to Penetrate Plant Seed Coat and Dramatically Affect Seed Germination and Plant Growth," ACS Nano, 3(10):3221-3227 (2009).
Kikkert et al., "Stable Transformation of Plant Cells by Particle Bombardment/Biolistics," Methods in Molecular Biology, 286:61-78 (2005).
Kim et al., "Optimization of Conditions for Transient Agrobacterium-Mediated Gene Expression Assays in *Arabidopsis*," Plant Cell Reports, 28:1159-1167 (2009).
Kim et al., "Synthetic dsRNA Dicer substrates enhance RNAi potency and efficacy," Nature Biotechnology, 23(2):222-226 (2005).
Kirkwood, "Herbicides and Plants," Botanical Journal of Scotland, 46(3):447-462 (1993).
Kirkwood, "Use and Mode of Action of Adjuvants for Herbicides: A Review of some Current Work," Pestic Sci., 38:93-102 (1993).
Klahre et al., "High molecular weight RNAs and small interfering RNAs induce systemic posttranscriptional gene silencing in plants," Proc. Natl. Acad. Sci. USA, PNAS, 99(18):11981-11986 (2002).
Knudsen, "Promoter2.0: for the recognition of Poll promoter sequences," Bioinformatics, 15(5):356-361 (1999).
Kronenwett et al., "Oligodeoxyribonucleotide Uptake in Primary Human Hematopoietic Cells Is Enhanced by Cationic Lipids and Depends on the Hematopoietic Cell Subset," Blood, 91(3):852-862 (1998).
Kumar et al., Sequencing, De Novo Assembly and Annotation of the.
Kusaba et al., "Low glutelin content1: A Dominant Mutation That Suppresses the Glutelin Multigene Family via RNA Silencing ni Rice," The Plant Cell, 15(6):1455-1467 (2003).
Kusaba, "RNA interference in crop plants," Curr Opin Biotechnol, 15(2):139-143 (2004).
Lavigne et al., "Enhanced antisense inhibition of human immunodeficiency virus type 1 in cell cultures by DLS delivery system," Biochem Biophys Res Commun, 237:566-571 (1997).
Lee et al., "Aptamer Database," Nucleic Acids Research, 32:D95-D100 (2004).
Lein et al., "Target-based discovery of novel herbicides," Current Opinion in Plant Biology, 7:219-225 (2004).
Leopold et al., "Chapter 4: Moisture as a Regulator of Physiological Reaction in Seeds," Seed Moisture, CSSA Special Publication No. 14, pp. 51-69 (1989).
Lermontova et al., "Reduced activity of plastid protoporphyrinogen oxidase causes attenuated photodynamic damage during high-light compared to low-light exposure," The Plant Journal, 48(4):499-510 (2006).
Lesnik et al., "Prediction of rho-independent transcriptional terminators in *Escherichia coli*," Nucleic Acids Research, 29(17):3583-3594 (2001).
Li et al., "A Simplified Seed Transformation Method for Obtaining Transgenic *Brassica napus* Plants," Agricultural Sciences in China, 8(6):658-663 (2009).
Li et al., "Establishment of a highly efficient transformation system for pepper (*Capsicum annuum* L.)," Plant Cell Reports, 21:785-788 (2003).
Li et al., "The FAST technique: a simplified Agrobacterium-based transformation method for transient gene expression analysis in seedlings of *Arabidopsis* and other plant species," Plant Methods, 5(6):1-15 (2009).
Liu et al, "The Helicase and RNaseIIIa Domains of *Arabidopsis* Dicer-Like1 Modulate Catalytic Parameters during MicroRNA Biogenesis," Plant Physiology, 159:748-758 (2012).
Liu et al., "Carbon Nanotubes as Molecular Transporters for Walled Plant Cells," Nano Letters, 9(3):1007-1010 (2009).
Liu et al., "Comparative study on the interaction of DNA with three different kinds of surfactants and the formation of multilayer films," Bioelectrochemistry, 70:301-307 (2007).
Liu et al., "DNAzyme-mediated recovery of small recombinant RNAs from a 5S rRNA-derived chimera expressed in *Escherichia coli*," BMC Biotechnology, 10:85 (2010).
Liu et al., "Identification and Application of a Rice Senescence-Associated Promoter," Plant Physiology, 153:1239-1249 (2010).
Liu, "Influence of Sugars on the Foliar Uptake of Bentazone and Glyphosate," New Zealand Plant Protection, 55:159-162 (2002).
Llave et al., "Endogenous and Silencing-Associated Small RNAs in Plants," The Plant Cell, 14:1605-1619 (2002).
Lu et al., "Oligo Walk: an online siRNA design tool utilizing hybridization thermodynamics," Nucleic Acids Research, 36:W104-W108 (2008).
Lu et al., "RNA silencing in plants by the expression of siRNA duplexes," Nucleic Acids Res., 32(21):e171 (2004).
Luft, "Making sense out of antisense oligodeoxynucleotide delivery: getting there is half the fun," J Mol Med, 76:75-76 (1998).
Luque et al., "Water Permeability of Isolated Cuticular Membranes: A Structural Analysis," Archives of Biochemistry and Biophysics, 317(2):417-422 (1995).
Maas et al., "Mechanism and optimized conditions for PEG mediated DNA transfection into plant protoplasts," Plant Cell Reports, 8:148-149 (1989).
MacKenzie et al., "Transgenic Nicotiana debneyii expressing viral coat protein are resistant to potato virus S infection," Journal of General Virology, 71:2167-2170 (1990).
Maher III et al., "Inhibition of DNA binding proteins by oligonucleotide-directed triple helix formation," Science, 245(4919):725-730 (1989).
Makkouk et al., "Virus Diseases of Peas, Beans, and Faba Bean in the Mediterranean region," Adv Virus Res, 84:367-402 (2012).
Mandal et al., "Adenine riboswitches and gene activation by disruption of a transcription terminator," Nature Struct. Mol. Biol., 11(1):29-35 (2004).
Mandal et al., "Gene Regulation by Riboswitches," Nature Reviews | Molecular Cell Biology, 5:451-463 (2004).
Manoharan, "Oligonucleotide Conjugates as Potential Antisense Drugs with Improved Uptake, Biodistribution, Targeted Delivery, and Mechanism of Action," Antisense & Nucleic Acid Drug Development, 12:103-128 (2002).
Maori et al., "IAPV, a bee-affecting virus associated with Colony Collapse Disorder can be silenced by dsRNA ingestion," Insect Molecular Biology, 18(1):55-60 (2009).
Masoud et al., "Constitutive expression of an inducible β-1,3-glucanase in alfalfa reduces disease severity caused by the oomycete pathogen Phytophthora megasperma f. sp *medicaginis*, but does not reduce disease severity of chitincontaining fungi," Transge.
Matveeva et al., "Prediction of antisense oligonucleotide efficacy by in vitro methods," Nature Biotechnology, 16:1374-1375 (1998).
McGinnis, "RNAi for functional genomics in plants," Brief Funct Genomics, 9(2):111-7 (2010).
Meinke, et al., "Identifying essential genes in *Arabidopsis thaliana*," Trends Plant Sci., 13(9):483-491 (2008).

(56) References Cited

OTHER PUBLICATIONS

Meins et al., "RNA Silencing Systems and Their Relevance to Plant Development," Annu. Rev. Cell Dev. Biol., 21:297-318 (2005).
Melnyk et al., "Intercellular and systemic movement of RNA silencing signals," The EMBO Journal, 30:3553-3563 (2011).
Migge et al., "Greenhouse-grown conditionally lethal tobacco plants obtained by expression of plastidic glutamine synthetase antisense RNA may contribute to biological safety," Plant Science 153:107-112 (2000).
Misawa et al., "Expression of an Erwinia phytoene desaturase gene not only confers multiple resistance to herbicides interfering with carotenoid biosynthesis but also alters xanthophyll metabolism in transgenic plants," The Plant Journal, 6(4):481-489 (19.
Misawa et al., "Functional expression of the Erwinia uredovora carotenoid biosynthesis gene crtl in transgenic plants showing an increase of β-carotene biosynthesis activity and resistance to the bleaching herbicide norflurazon," The Plant Journal, 4(5):8.
Miura et al., "The Balance between Protein Synthesis and Degradation in Chloroplasts Determines Leaf Variegation in Arabidopsis yellow variegated Mutants," The Plant Cell, 19:1313-1328 (2007).
Molina et al., "Inhibition of protoporphyrinogen oxidase expression in *Arabidopsis* causes a lesion-mimic phenotype that induces systemic acquired resistance," The Plant Journal, 17(6):667-678 (1999).
Molnar et al., "Plant Virus-Derived Small Interfering RNAs Originate redominantly from Highly Structured Single-Stranded Viral RNAs," Journal of Virology, 79(12):7812-7818 (2005).
Molnar et al., "Small Silencing RNAs in Plants Are Mobile and Direct Epigenetic Modification in Recipient Cells," Science, 328:872-875 (2010).
Mora et al., "How Many Species Are There on Earth and in the Ocean?," PLOS Biol., 9(8):e100127, p. 1-8 (2011).
Moriyama et al., "Double-stranded RNA in rice: a novel RNA replicon in plants," Molecular & General Genetics, 248(3):364-369 (1995).
Moriyama et al., "Stringently and developmentally regulated levels of a cytoplasmic double-stranded RNA and its high-efficiency transmission via egg and pollen in rice," Plant Molecular Biology, 31:713-719 (1996).
Morrissey et al., "Potent and persistent in vivo anti-HBV activity of chemically modified siRNAs," Nat Biotechnol. 23(8):1002-1007 (2005).
Moser et al., "Sequence—Specific Cleavage of Double Helical DNA by Triple Helix Formation," Science, 238:645-646 (1987).
Mount et al., "Gene and Metabolite Regulatory Network Analysis of Early Developing Fruit Tissues Highlights New Candidate Genes for the Control of Tomato Fruit Composition and Development," Plant Physiology, 149:1505-1528 (2009).
Non-Final Office Action dated Apr. 11, 2013, in U.S. Appl. No. 13/042,856.
Non-Final Office Action dated Apr. 29, 2016, in U.S. Appl. No. 13/583,302.
Non-Final Office Action dated Aug. 10, 2016, in U.S. Appl. No. 13/612,995.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Aug. 19, 2016, in U.S. Appl. No. 13/612,925.
Non-Final Office Action dated Aug. 19, 2016, in U.S. Appl. No. 13/612,929.
Non-Final Office Action dated Aug. 3, 2016, in U.S. Appl. No. 14/015,715.
Non-Final Office Action dated Aug. 5, 2016, in U.S. Appl. No. 14/015,785.
Non-Final Office Action dated Aug. 8, 2016, in U.S. Appl. No. 13/612,936.
Non-Final Office Action dated Dec. 17, 2015, in U.S. Appl. No. 14/532,596.
Non-Final Office Action dated Feb. 10, 2016, in U.S. Appl. No. 13/901,326.
Non-Final Office Action dated Feb. 23, 2016, in U.S. Appl. No. 14/603,347.
Non-Final Office Action dated Feb. 23, 2016, in U.S. Appl. No. 14/608,951.
Non-Final Office Action dated Jul. 23, 2015, in U.S. Appl. No, 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated Mar. 1, 2016, in U.S. Appl. No. 13/612,954.
Non-Final Office Action dated Mar. 30, 2015, in U.S. Appl. No. 13/583,302.
Non-Final Office Action dated May 15, 2015, in U.S. Appl. No. 14/608,951.
Non-Final Office Action dated May 22, 2015, in U.S. Appl. No. 13/612,985.
Non-Final Office Action dated Nov. 9, 2016, in U.S. Appl. No. 14/901,003.
Non-Final Office Action dated Oct. 3, 2016, in U.S. Appl. No. 14/403,491.
Non-Final Office Action dated Sep. 1, 2015, in U.S. Appl. No. 13/612,954.
Non-Final Office Action dated Sep. 11, 2015, in U.S. Appl. No. 13/612,925.
Non-Final Office Action dated Sep. 4, 2015, in U.S. Appl. No. 13/612,995.
Non-Final Office Action dated Sep. 6, 2016, in U.S. Appl. No. 14/335,135.
Nookaraju et al., "Molecular approaches for enhancing sweetness in fruits and vegetables," Scientia Horticulture, 127:1-15 (2010).
Nord-Larsen et al., "Cloning, characterization and expression analysis of tonoplast intrinsic proteins and glutamine synthetase in ryegrass (Lolium perenne L.)," Plant Cell Reports, 28(10):1549-1562 (2009).
Notice of Allowance dated Apr. 11, 2016, in U.S. Appl. No. 13/612,985.
Notice of Allowance dated Apr. 19, 2016, in U.S. Appl. No. 13/612,941.
Notice of Allowance dated Apr. 20, 2016, in U.S. Appl. No. 13/612,948.
Notice of Allowance dated Feb. 23, 2015, in U.S. Appl. No. 13/042,856.
Notice of Allowance dated Jun. 2, 2015, in U.S. Appl. No. 13/042,856.
Notice of Allowance dated Oct. 5, 2015, in U.S. Appl. No. 13/583,302.
Nowak et al., "A new and efficient method for inhibition of RNA viruses by DNA interference," The FEBS Journal, 276:4372-4380 (2009).
Office Action dated Apr. 13, 2016, in Chinese Patent Application No. 201280053985.3.
Office Action dated Aug. 1, 2017, in European Patent Application No. 12 830 932.5.
Office Action dated Aug. 14, 2017, in Israeli Patent Application No. 235878.
Office Action dated Aug. 22, 2017, in Korean Patent Application No. 10-2012-7023415.
Office Action dated Aug. 25, 2016, in Eurasian Patent Application No. 201201264.
Office Action dated Aug. 28, 2013, in Chinese Patent Application No. 201180012795.2.
Office Action dated Aug. 3, 2017, in Chinese Patent Application No. 201480014392.5 (with English translation).
Office Action dated Aug. 3, 2017, in European Patent Application No. 12 831 684.1.
Office Action dated Aug. 8, 2017, in Chilean Patent Application No. 201501874.
Office Action dated Dec. 13, 2016, in Ukrainian Patent Application No. a 2014 03843.

(56) References Cited

OTHER PUBLICATIONS

Office Action dated Dec. 14, 2016, in Ukrainian Patent Application No. a 2014 03850.
Office Action dated Dec. 15, 2016, in Ukrainian Patent Application No. a 2014 03845.
Office Action dated Dec. 15, 2016, in Ukrainian Patent Application No. a 2014 03849.
Office Action dated Dec. 15, 2016, in Ukrainian Patent Application No. a 2014 03852.
Office Action dated Dec. 27, 2016, in Ukrainian Patent Application No. a 2012 11548.
Office Action dated Dec. 5, 2017, in Japanese Patent Application No. 2016-502033.
Office Action dated Feb. 17, 2014, in Mexican Patent Application No. MX/a/2012/010479.
Office Action dated Feb. 24, 2014, in Eurasian Patent Application No. 201201264.
Office Action dated Jul. 11, 2017, in Mexican Patent Application No. MX/a/2015/013118 (with English translation).
Office Action dated Jul. 18, 2016, in Indonesian Patent Application No. W00201203610.
Office Action dated Jul. 23, 2015, in Ukrainian Patent Application No. 201211548.
Office Action dated Jul. 3, 2017, in Mexican Patent Application No. MX/a/2015/012632 (with English translation).
Office Action dated Jul. 6, 2017, in Mexican Patent Application No. MX/a/2015/013103 (with English translation).
Office Action dated Jun. 20, 2016, in Chinese Patent Application No. 201280054819.5.
Office Action dated Jun. 24, 2016, in Chinese Patent Application No. 201280053984.9.
Office Action dated Mar. 16, 2017, in Chinese Patent Application No. 201280054819.5.
Office Action dated May 3, 2016, in Chilean Patent Application No. 201601057.
Office Action dated Nov. 15, 2016, in Mexican Patent Application No. MX/a/2014/003068 (with English translation).
Office Action dated Sep. 5, 2016, in Ukrainian Patent Application No. a 2014 03846.
Office Action dated Sep. 6, 2017, in Chinese Patent Application No. 2014800154012 (with English translation).
Office Action dated Nov. 3, 2014, in Chinese Patent Application No. 201180012795.2.
Office Action dated Jan. 6, 2015, in Japanese Patent Application No. 2012-557165.
Office Action dated Nov. 19, 2014, in Eurasian Patent Application No. 201201264/28.
Office Action dated Oct. 5, 2015, in Eurasian Patent Application No. 201201264/28.
Ongvarrasopone et al., "A Simple and Cost Effective Method to Generate dsRNA for RNAi Studies in Invertebrates," Science Asia, 33:35-39 (2007).
Orbović et al., "Foliar-Applied Surfactants and Urea Temporarily Reduce Carbon Assimilation of Grapefruit Leaves," J. Amer. Soc. Hort. Sci., 126(4):486-490 (2001).
Ouellet et al., "Members of the Acetohydroxyacid Synthase Muligene Family of *Brassica napus* Have Divergent Patterns of Expression," The Plant Journal, Blackwell Scientific Publications, Oxford, GB, 2(3):321-330 (1992).
Paddison et al., Stable suppression of gene expression by RNAi in.
Palauqui et al., "Activation of systemic acquired silencing by localised introduction of DNA," Current Biology, 9:59-66 (1999).
Parera et al., "Dehydration Rate after Solid Matrix Priming Alters Seed Performance of Shrunken-2 Corn," J. Amer. Soc. Hort. Sci., 119(3):629-635 (1994).
Partial European Search Report dated Dec. 6, 2017, in European Patent Application No. 17181861.0.
Partial Supplementary European Search Report dated Mar. 2, 2015, in European Patent Application No. 12 831 494.5.
Patent Examination Report No. 1 dated Feb. 8, 2016, in Australian Patent Application No. 2014262189.
Patent Examination Report No. 1 dated Jun. 17, 2016, in Australian Patent Application No. 2012308659.
Patent Examination Report No. 1 dated Jun. 17, 2016, in Australian Patent Application No. 2012308660.
Patent Examination Report No. 1 dated Jun. 8, 2017, in Australian Patent Application No. 2012308686.
Patent Examination Report No. 1 dated Nov. 11, 2013, in Australian Patent Application No. 2011224570.
Paungfoo-Lonhienne et al., "DNA is Taken up by Root Hairs and Pollen, and Stimulates Root and Pollen Tube Growth," Plant Physiology, 153:799-805 (2010).
Paungfoo-Lonhienne et al., "DNA uptake by *Arabidopsis* induces changes in the expression of CLE peptides which control root morphology," Plant Signaling & Behavior, 5(9):1112-1114 (2010).
Pei et al., "On the art of identifying effective and specific siRNAs," Nature Methods, 3(9):670-676 (2006).
Peretz et al., "A Universal Expression/Silencing Vector in Plants," Plant Physiology, 145:1251-1263 (2007).
Pornprom et al., "Glutamine synthetase mutation conferring target-site-based resistance to glufosinate in soybean cell selections," Pest Manag Sci, 2009; 65(2):216-222 (2009).
Powles et al., "Evolution in Action: Plants Resistant to Herbicides," Annual Review of Plant Biology, 61(1):317-347 (2010).
Pratt et al., "Amaranthus rudis and A. tuberculatus, One Species or Two?," Journal of the Torrey Botanical Society, 128(3):282-296 (2001).
Preston et al., "Multiple effects of a naturally occurring proline to threonine substitution within acetolactate synthase in two herbicide-resistant populations of Lactuca serriola," Pesticide Biochem. Physiol., 84(3):227-235 (2006).
Promoter Prediction for SEQ ID No. 1702 from 13/612929/MK/, Promoter 2.0 Prediction Results, pp. 1-4 (2016).
Promoter Prediction for SEQ ID No. 4 from 13/612995/MK/, Promoter 2.0 Prediction Results, pp. 1-3 (2016).
Promoter Prediction for SEQ ID No. 7 from 13/612936/MK/, Promoter 2.0 Prediction Results, pp. 1-2 (2016).
Promoter Prediction for SEQ ID No. 8 from 13/612,925/MK/, Promoter 2.0 Prediction Results, pp. 1-6 (2016).
Qichuan et al., Seed Science, China Agriculture Press, pp. 101-103, Table 2-37.
Qiwei, "Advance in DNA interference," Progress in Veterinary Medicine, 30(1):71-75 (2009).
Rajur et al., "Covalent Protein—Oligonucleotide Conjugates for Efficient Delivery of Antisense Molecules," Bioconjug Chem., 8:935-940 (1997).
Rakoczy-Trojanowska, "Alternative Methods of Plant Transformation—a short review," Cellular & Molecular Biology Letters, 7:849-858 (2002).
Reddy et al "Organosilicone Adjuvants Increased the Efficacy of Glyphosate for Control of Weeds in Citrus (*Citrus* spp.)" HortScience 27(9):1003-1005 (1992).
Reddy et al., "Aminomethylphosphonic Acid Accumulation in Plant Species Treated with Glyphosate," J. Agric. Food Chem., 56(6):2125-2130 (2008).
Regalado, "The Next Great GMO Debate," MIT Technology Review,pp. 1-19 (2015) <https://www.technologyreview.com/s/540136/the-next-great-gmo-debate/>.
Reither et al., "Specificity of DNA triple helix formation analyzed by a FRET assay," BMC Biochemistry, 3:27 (2002).
Restriction Requirement dated Apr. 21, 2015, in U.S. Appl. No. 13/612,954.
Restriction Requirement dated Feb. 12, 2015, in U.S. Appl. No. 13/612,985.
Restriction Requirement dated Jul. 15, 2016, in U.S. Appl. No. 14/143,748.
Restriction Requirement dated Jul. 18, 2016, in U.S. Appl. No. 14/143,836.
Restriction Requirement dated Mar. 12, 2015, in U.S. Appl. No. 13/612,948.
Restriction Requirement dated Mar. 4, 2015, in U.S. Appl. No. 13/612,941.

(56) References Cited

OTHER PUBLICATIONS

Restriction Requirement dated May 4, 2015, in U.S. Appl. No. 13/612,929.
Restriction Requirement dated May 5, 2015, in U.S. Appl. No. 13/612,936.
Restriction Requirement dated May 7, 2015, in U.S. Appl. No. 13/612,925.
Restriction Requirement dated May 7, 2015, in U.S. Appl. No. 13/612,995.
Restriction Requirement dated Oct. 13, 2016, in U.S. Appl. No. 14/206,707.
Restriction Requirement dated Oct. 2, 2012, in U.S. Appl. No. 13/042,856.
Restriction Requirement dated Oct. 21, 2014, in U.S. Appl. No. 13/583,302.
Restriction Requirement dated Oct. 28, 2015, in U.S. Appl. No. 14/603,347.
Restriction Requirement dated Sep. 2, 2015, in U.S. Appl. No. 14/532,596.
Rey et al., "Diversity of Dicotyledenous-Infecting Geminiviruses and Their Associated DNA Molecules in Southern Africa, Including the South-West Indian Ocean Islands," Viruses, 4:1753-1791 (2012).
Reynolds et al., "Rational siRNA design for RNA interference," Nature Biotechnology, 22:326-330 (2004).
Richardson et al., "Targeting and assembly of components of the TOC protein import complex at the chloroplast outer envelope membrane," Frontiers in Plant Science, 5:1-14 (2014).
Riggins et al., "Characterization of de novo transcriptome for waterhemp (*Amaranthus tuberculatus*) using GS-FLX 454 pyrosequencing and its application for studies of herbicide target-site genes," Pest Manag. Sci., 66:1042-1052 (2010).
Roberts, "Fast-track applications: The potential for direct delivery of proteins and nucleic acids to plant cells for the discovery of gene function," Plant Methods, 1(12):1-3 (2005).
Robson et al., "Leaf senescence is delayed in maize expressing the Agrobacterium IPT gene under the control of a novel maize senescence-enhanced promoter," Plant Biotechnology Journal, 2:101-112 (2004).
Roitsch et al., "Extracellular invertase: key metabolic enzyme and PR protein," Journal of Experimental Botany, 54(382):513-524 (2003).
Roitsch et al., "Function and regulation of plant invertases: sweet sensations," Trades in Plant Science, 9(12):606-613 (2004).
Rose et al., "Functional polarity is introduced by Dicer processing of short substrate RNAs," Nucleic Acids Research, 33(13):4140-4156 (2005).
Rothnie et al., Pararetroviruses and Retroviruses: A Comparative Review of Viral Structure and Gene Expression Strategies, Advances in Virus Research, 44:1-67 (1994).
Ruan et al., "Suppression of Sucrose Synthase Gene Expression Represses Cotton Fiber Cell Initiation, Elongation, and Seed Development," The Plant Cell, 15:952-964 (2003).
Ryabov et al., "Cell-to-Cell, but Not Long-Distance, Spread of RNA Silencing That is Induced in Individual Epidermal Cells," Journal of Virology, 78(6):3149-3154 (2004).
Ryan, "Human endogenous retroviruses in health and disease: a symbiotic perspective," Journal of the Royal Society of Medicine, 97:560-565 (2004).
Salanenka et al., "Seedcoat Permeability: Uptake and Post-germination Transport of Applied Model Tracer Compounds," HortScience, 46(4):622-626 (2011).
Santoro et al., "A general purpose RNA-cleaving DNA enzyme," Proc. Natl. Acad. Sci. USA, 94:4262-4266 (1997).
Sathasivan et al., "Nucleotide sequence of a mutant acetolactate synthase gene from an imidazolinone-resistant *Arabidopsis thaliana* var. Columbia," Nucleic Acids Research, 18(8):2188-2193 (1990).
Schönherr, "Water Permeability of Isolated Cuticular Membranes: The Effect of pH and Cations on Diffusion, Hydrodynamic Permeability and Size of Polar Pores in the Cutin Matrix," Planta, 128:113-126 (1976).
Schwab et al., "RNA silencing amplification in plants: Size matters," PNAS, 107(34):14945-14946 (2010).
Schweizer et al., "Double-stranded RNA interferes with gene function at the single-cell level in cereals," The Plant Journal, 24(6):895-903 (2000).
Schwember et al., "Drying Rates following Priming Affect Temperature Sensitivity of Germination and Longevity of Lettuce Seeds," HortScience, 40(3):778-781 (2005).
Scott et al., Botanical Insecticides for Controlling Agricultural Pests: Piperamides and the Colorado Potato Beetle *Leptinotarsa decemlineata* Say (Coleoptera: Chrysomelidae), Archives of Insect Biochemistry and Physiology, 54:212-225 (2003).
Search Report dated Jul. 24, 2017, in Chinese Patent Application No. 201480014392.5 (with English translation).
Search Report dated Oct. 20, 2017, in Chinese Patent Application No. 201380039346.6.
Second Chinese Office Action dated Jun. 10, 2014, in Chinese Patent Application No. 201180012795.2.
Second Office Action dated Feb. 25, 2016, in Chinese Patent Application No. 201280054179.8.
Second Office Action dated Mar. 4, 2016, in Chinese Patent Application No. 201280054820.8.
Seidman et al., "The potential for gene repair via triple helix formation," J Clin Invest., 112(4):487-494 (2003).
Selvarani et al., "Evaluation of seed priming methods to improve seed vigour of onion (*Allium cepa* cv. *Aggregatum*) and carrot (*Daucus carota*)," Journal of Agricultural Technology, 7(3):857-867 (2011).
Senthil-Kumar et al., "A systematic study to determine the extent of gene silencing in *Nicotiana benthamiana* and other *Solanaceae* species when heterologous gene sequences are used for virus-induced gene silencing," New Phytologist, 176:782-791 (2007).
Sharma et al., "A simple and efficient Agrobacterium-mediated procedure for transformation of tomato," J. Biosci., 34(3):423 433 (2009).
Shintani et al., "Antisense Expression and Overexpression of Biotin Carboxylase in Tobacco Leaves," Plant Physiol., 114:881-886 (1997).
Showalter, "Structure and Function of Plant Cell Wall Proteins," The Plant Cell, 5:9-23 (1993).
Sijen et al., "On the Role of RNA Amplification in dsRNA-Triggered Gene Silencing," Cell, 107:465-476 (2001).
Silwet L-77 Spray Adjuvant for agricultural applications, product description from Momentive Performance Materials, Inc. (2003).
Singh et al., "Absorption and translocation of glyphosate with conventional and organosilicone adjuvants," Weed Biology and Management, 8:104-111 (2008).
Small, "RNAi for revealing and engineering plant gene functions," Current Opinion in Biotechnology, 18:148-153 (2007).
Snead et al., "Molecular basis for improved gene silencing by Dicer substrate interfering RNA compared with other siRNA variants," Nucleic Acids Research, 41(12):6209-6221 (2013).
Song et al., "Herbicide," New Heterocyclic Pesticide, Chemical Industry Press, 354-356 (2011).
Statement of Grounds and Particulars dated Sep. 1, 2017, in Australian Patent No. 2014262189.
Steeves et al., "Transgenic soybeans expressing siRNAs specific to a major sperm protein gene suppress Heterodera glycines reproduction," Funct. Plant Biol., 33:991-999 (2006).
Stevens et al., "New Formulation Technology—SILWET® Organosilicone Surfactants Have Physical and Physiological Properties Which Enhance the Performance of Sprays," Proceedings of the 9th Australian Weeds Conference, pp. 327-331 (1990).
Stevens, "Formulation of Sprays to Improve the Efficacy of Foliar Fertilisers," New Zealand Journal of Forestry Science, 24(1):27-34 (1994).
Stevens, "Organosilicone Surfactants as Adjuvants for Agrochemicals," New Zealand Journal of Forestry Science, 24:27-34 (1994).
Stock et al., "Possible Mechanisms for Surfactant-Induced Foliar Uptake of Agrochemicals," Pestic. Sci., 38:165-177 (1993).
Strat et al., "Specific and nontoxic silencing in mammalian cells with expressed long dsRNAs," Nucleic Acids Research, 34(13):3803-3810 (2006).

(56) References Cited

OTHER PUBLICATIONS

Street, "Why is DNA (and not RNA) a stable storage form for genetic information?," Biochemistry Revisited, pp. 1-4 (2008).
Sudarsan et al., "Metabolite-binding RNA domains are present in the genes of eukaryotes," RNA, 9:644-647 (2003).
Summons to Attend Oral Proceedings Pursuant to Rule 115(1) EPC, dated Aug. 7, 2017, in European Patent Application No. 12832160.1.
Sun et al., "A Highly efficient Transformation Protocol for Micro-Tom, a Model Cultivar for Tomato Functional Genomics," Plant Cell Physiol., 47(3):426-431 (2006).
Sun et al., "Antisense oligodeoxynucleotide inhibition as a potent strategy in plant biology: identification of SUSIBA2 as a transcriptional activator in plant sugar signalling," The Plant Journal, 44:128-138 (2005).
Sun et al., "Sweet delivery—sugar translocators as ports of entry for antisense oligodeoxynucleotides in plant cells," The Plant Journal, 52:1192-1198 (2007).
Sutton et al., "Activity of mesotrione on resistant weeds in maize," Pest Manag. Sci., 58:981-984 (2002).
Takasaki et al., "An Effective Method for Selecting siRNA Target Sequences in Mammalian Cells," Cell Cycle, 3:790-795 (2004).
Tang et al., "Efficient delivery of small interfering RNA to plant cells by a nanosecond pulsed laser-induced stress wave for post-transcriptional gene silencing," Plant Science, 171:375-381 (2006).
Tank Mixing Chemicals Applied to Peanut Crops: Are the Chemicals Compatible?, College of Agriculture & Life Sciences, NC State University, AGW-653, pp. 1-11 (2004).
Taylor, "Seed Storage, Germination and Quality," The Physiology of Vegetable Crops, pp. 1-36 (1997).
Temple et al., "Can glutamine synthetase activity levels be modulated in transgenic plants by the use of recombinant DNA technology?" Transgenic Plants and Plant Biochemistry, 22(4):915-920 (1994).
Temple et al., "Down-regulation of specific members of the glutamine synthetase gene family in Alfalfa by antisense RNA technology," Plant Molecular Biology, 37:535-547 (1998).
Templeton et al., "Improved DNA: liposome complexes for increased systemic delivery and gene expression," Nature Biotechnology, 15:647-652 (1997).
Tenllado et al., "Crude extracts of bacterially expressed dsRNA can be used to protect plants against virus infection," BMC Biotechnology, 3(3):1-11 (2003).
Tenllado et al, "Double-Stranded RNA-Mediated Interference with Plant Virus Infection," Journal of Virology, 75(24):12288-12297 (2001).
Tenllado et al., "RNA interference as a new biotechnological tool for the control of virus diseases in plants," Virus Research, 102:85-96 (2004).
Tepfer, "Risk assessment of virus resistant transgenic plants," Annual Review of Phytopathology, 40:467-491 (2002).
The Seed Biology Place, Website Gerhard Leubner Lab Royal Holloway, University of London, <http://www.seedbiology.de/seedtechnology.asp.
Third Party Submission filed on Nov. 29, 2012 in U.S. Appl. No. 13/042,856.
Thomas et al., "Size constraints for targeting post-transcriptional gene silencing and for RNA-directed methylation in Nicotiana benthamiana using a potato virus X vector," The Plant Journal, 25(4):417-425 (2001).
Thompson, et al., "CLUSTAL W: improving the sensitivity of progressive multiple sequence alignment through sequence weighting, position-specific gap penalties and weight matrix choice," Nucl. Acids Res., 22(22):4673-4680 (1994).
Timmons et al., "Specific interference by ingested dsRNA," Nature, 395:854 (1998).
Tomari et al., "Perspective: machines for RNAi," Genes & Dev., 19:517-529 (2005).
Tomlinson et al., "Evidence that the hexose-to-sucrose ratio does not control the switch to storage product accumulation in oilseeds: analysis of tobacco seed development and effects of overexpressing apoplastic invertase," Journal of Experimental Botany.
Töpfer et al., "Uptake and Transient Expression of Chimeric Genes in Seed-Derived Embryos," Plant Cell, 1:133-139 (1989).
Toriyama et al., Transgenic Rice Plants After Direct Gene Transfer Into.
Tran et al., "Control of specific gene expression in mammalian cells by co-expression of long complementary RNAs," FEBS Lett.;573(1-3):127-134 (2004).
Tranel et al., "Resistance of weeds to ALS-inhibiting herbicides: what have we learned?," Weed Science, 50:700-712 (2002).
Trucco et al., "Amaranthus hybridus can be pollinated frequently by A. tuberculatus under filed conditions," Heredity, 94:64-70 (2005).
Tsugawa et al., "Efficient transformation of rice protoplasts mediated by a synthetic polycationic amino polymer," Theor Appl Genet, 97:1019-1026 (1998).
Turina et al., "Tospoviruses in the Mediterranean Area," Advances in Virus Research, 84:403-437 (2012).
Tuschl, "Expanding small RNA interference," Nature Biotechnol., 20: 446-448 (2002).
Tuschl, "RNA Interference and Small Interfering RNAs," ChemBiochem. 2(4):239-245 (2001).
Ui-Tei et al., "Guidelines for the selection of highly effective siRNA sequences for mammalian and chick RNA interference," Nucleic Acids Res., 32(3): 936-948 (2004).
Unnamalai et al., "Cationic oligopeptide-mediated delivery of dsRNA for post-transcriptional gene silencing in plant cells," FEBS Letters, 566:307-310 (2004).
Unniraman et al., "Alternate Paradigm for Intrinsic Transcription Termination in Eubacteria," The Journal of Biological Chemistry, 276(45)(9):41850-41855 (2001).
Unniraman et al., "Conserved Economics of Transcription Termination in Eubacteria," Nucleic Acids Research, 30(3):675-684 (2002).
Urayama et al., "Knock-down of OsDCL2 in Rice Negatively Affects Maintenance of the Endogenous dsRNA Virus, Oryza sativa Endornavirus," Plant and Cell Physiology, 51(1):58-67 (2010).
Van de Wetering et al., "Specific inhibition of gene expression using a stably integrated, inducible small-interfering-RNA vector," EMBO Rep., 4(6):609-615 (2003).
Vasil et al., "Herbicide Resistant Fertile Transgenic Wheat Plants Obtained by Microprojectile Bombardment of Regenerable Embryogenic Callus," Bio/Technology,10:667-674 (1992).
Vaucheret, "Post-transcriptional small RNA pathways in plants: mechanisms and regulations," Genes Dev., 20:759-771 (2006).
Vencill et al., "Resistance of Weeds to Herbicides," Herbicides and Environment, 29:585-594 (2011).
Verma et al., "Modified oligonucleotides: synthesis and strategy for users," Annu. Rev. Biochem., 67:99-134 (1998).
Vermeulen et al., "The contributions of dsRNA structure to Dicer specificity and efficiency," RNA, 11(5):674-682 (2005).
Vert et al., "An accurate and interpretable model for siRNA efficacy prediction," BMC Bioinformatics, 7:520 (2006).
Voinnet et al., "Systemic Spread of Sequence-Specific Transgene RNA Degradation in Plants Is Initiated by Localized Introduction of Ectopic Promoterless DNA," Cell, 95:177-187 (1998).
Voinnet, "Origin, Biogenesis, and Activity of Plant MicroRNAs," Cell, 136:669-687 (2009).
Wakelin et al., "A target-site mutation is present in a glyphosate-resistant Lolium rigidum population," Weed Res. (Oxford), 46(5):432-440 (2006).
Walton et al., "Prediction of antisense oligonucleotide binding affinity to a structured RNA target," Biotechnol Bioeng 65(1):1-9 (1999).
Wan et al., "Generation of Large Numbers of Independently Transformed Fertile Barley Plants," Plant Physiol., 104:37-48 (1994).
Wang et al., "Foliar uptake of pesticides-Present status and future challenge," ScienceDirect, 87:1-8 (2007).
Wardell, "Floral Induction of Vegetative Plants Supplied a Purified Fraction of Deoxyribonucleic Acid from Stems of Flowering Plants," Plant Physiol, 60:885-891 (1977).
Wardell,"Floral Activity in Solutions of Deoxyribonucleic Acid Extracted from Tobacco Stems," Plant Physiol, 57:855-861 (1976).

(56) References Cited

OTHER PUBLICATIONS

Waterhouse et al., "Virus resistance and gene silencing in plants can be induced by simultaneous expression of sense and antisense RNA," Proc Natl Acad Sci USA, 95 13959-13964 (1998).

Welch et al., "Expression of ribozymes in gene transfer systems to modulate target RNA levels," Curr Opin Biotechnol. 9(5):486-496 (1998).

Widholm et al., "Glyphosate selection of gene amplification in suspension cultures of 3 plant species," Phyisologia Plantarum, 112:540-545 (2001).

Wiesman et al., "Novel cationic vesicle platform derived from vernonia oil for efficient delivery of DNA through plant cuticle membranes," Journal of Biotechnology, 130:85-94 (2007).

Wild Carrot, Noxious Weed Control Board (NWCB) of Washington State (2010) <www.nwcb.wa.gov/detail.asp?weed=46>.

Wilson, et al., "Transcription termination at intrinsic terminators: The role of the RNA hairpin," Proc. Natl. Acad. Sci. USA, 92:8793-8797 (1995).

Winkler et al., "Thiamine derivatives bind messenger RNAs directly to regulate bacterial gene expression," Nature, 419:952-956 (2002).

Wool et al., "Structure and evolution of mammalian ribosomal proteins," Biochem. Cell Biol., 73:933-947 (1995).

Written Opinion dated Apr. 7, 2016, in Singapore Patent Application No. 201206152-9.

Written Opinion dated Mar. 6, 2017, in Singaporean Patent Application No. 2012061529.

Written Opinion dated May 8, 2014, in International Application No. PCT/IL2013/050447.

Written Opinion dated Sep. 1, 2014, in Singapore Patent Application No. 201206152-9.

Xu et al., "Characterization and Functional Analysis of the Calmodulin-Binding Domain of Rac1 GTPase," PLoS One, 7(8):e42975 (2012).

Yin et al., "Production of double-stranded RNA for interference with TMV infection utilizing a bacterial prokaryotic expression system," Appl. Microbiol. Biotechnol., 84(2):323-333 (2009).

YouTube video by General Electric Company "Silwet Surfactants," screen shot taken on Jan. 11, 2012 of video of www.youtube.com/watch?v=WBw7nXMqHk8 (uploaded Jul. 13, 2009).

Zagnitko, "Lolium regidum clone LS1 acetyl-CoA carboxylase mRNA, partial cds; nuclear gene for plastid product," GenBank: AF359516.1, 2 pages (2001).

Zagnitko, et al., "An isoleucine/leucine residue in the carboxyltransferase domain of acetyl-CoA carboxylase is critical for interaction with aryloxyphenoxypropionate and cyclohexanedione inhibitors," PNAS, 98(12):6617-6622 (2001).

Zaimin et al., Botany, Northwest A&F University Press, p. 89.

Zhang et al., "Development and Validation of Endogenous Reference Genes for Expression Profiling of Medaka (Oryzias latipes) Exposed to Endocrine Disrupting Chemicals by Quantitative Real-Time RT-PCR," Toxicological Sciences, 95(2):356-368 (2007).

Zhang et al., "A novel rice gene, NRR responds to macronutrient deficiency and regulates root growth," Mol Plant, 5(1):63-72 (2012).

Zhang et al., "Agrobacterium-mediated transformation of *Arabidopsis thaliana* using the floral dip method," Nature Protocols, 1(2):1-6 (2006).

Zhang et al., "Cationic lipids and polymers mediated vectors for delivery of siRNA," Journal of Controlled Release, 123:1-10 (2007).

Zhang et al., "DEG: a database of essential genes," Nucleic Acids Res., 32:D271-D272 (2004).

Zhang et al., "Transgenic rice plants produced by electroporation-mediated plasmid uptake into protoplasts," The Plant Cell Rep., 7:379-384 (1988).

Zhang, "Artificial trans-acting small interfering RNA: a tool for plant biology study and crop improvements," Planta, 239:1139-1146 (2014).

Zhang, Chapter 10: New Characteristics of Pesticide Research & Development, p. 209 (2010).

Zhao et al., "Phyllotreta striolata (Coleoptera: Chrysomelidae):Arginine kinase cloning and RNAi-based pest control," European Journal of Entomology, 105(5):815-822 (2008).

Zhong et al., "A forward genetic screen to explore chloroplast protein import in vivo identifies Moco sulfurase, pivotal for ABA and IAA biosynthesis and purine turnover," The Plant Journal, 63:44-59 (2010).

Zhu et al., "Ingested RNA interference for managing the populations of the Colorado potato beetle, *Leptinotarsa decemlineata*," Pest Manag Sci, 67:175-182 (2010).

Bauer et al., "The major protein import receptor of plastids is essential for chloroplast biogenesis," Nature, 403:203-207 (2000).

Baum et al., "Progress Towards RNAi-Mediated Insect Pest Management," Advances in insect Physiology, 47:249-295 (2014).

Chang et al., "Dual-target gene silencing by using long, synthetic siRNA duplexes without triggering antiviral responses," Molecules and Cells, 27(6)" 689-695 (2009).

Cheng et al., "Transient Expression of Minimum Linear Gene Cassettes in Onion Epidermal Cells Via Direct Transformation," Appl Biochem Biotechnol, 159:739-749 (2009).

Christiaens et al., "The challenge of RNAi-mediated control of hemipterans," Current Opinion in Insect Science, 6:15-21 (2014).

Communication Pursuant to Article 94(3) EPC dated Sep. 5, 2018, in European Patent Application No. 17152830.0.

Database EMBL XP-002781749(BG442539) dated Mar. 20, 2001.

Egli et al., "A Maize Acetyl-Coenzyme A Carboxylase cDNA Sequence," Plant Physiol., 108: 1299-1300 (1995).

European Search. Report dated Jun. 29, 2018, in European Patent Application No. 18157745.3.

Examination Report dated Mar. 1, 2018, in Australian Patent Application No. 2013264742.

Extended European Search Report dated Sep. 28, 2018, in European Patent Application No, 16740770.9.

Extended European Search Report dated Apr. 13, 2018, in European Patent Application No, 15812530.0.

Extended European Search Report dated Mar. 15, 2018, in European Patent Application No. 17181861.0.

Gallie et al., "Identification of the motifs within the tobacco mosaic virus 5'-leader responsible for enhancing translation," Nucleic Acids Res., 20(17):4631-4638 (1992).

Gan et al., "Bacterially expressed dsRNA protects maize against SCMV nfection," Plant Cell Rep, 11:1261-1268 (2010).

Gasser et al., "Structure, Expression, and Evolution of the 5-Enolpyruvylshikimate-3-phosphate Synthase Genes of Petunia and Tomato," J. Biol. Chem., 263: 4280-4287 (1988).

Gomez-Zurita et al., "Recalibrated Tree of Leaf Beetles (*Chrysomelidae*) Indicates Independent Diversification of Angiosperms and Their Insect Herbivores," PLoS One, 4(e360):1-8 (2007).

Hoermann et al., "Tic32, as Essential Component in Chloroplast Biogenesis," The Journal of Biological Chemistry, 279(33):34756-34762 (2004).

Hu et al., "High efficiency transport of quantum dots into plant roots with the aid of silwet L-77," Plant Physiology and Biochemistry, 48:703-709 (2010).

Inaba et al., "*Arabillopsis* Tic110 Is Essential for the Assembly and Function of Protein Import Machinery of Plastids," The Plant Cell, 17:1482-1496 (2005).

Jarvis et al, "An *Arabidopsis* mutant defective in the plastid general protein import apparatus," Science, 282:100-103 (1998).

Kovacheva et al., "Further in viva studies on the role of the molecular chaperone, Hsp93, in plastid protein import," The Plant Journal, 50:364-379 (2007).

Kovacheva et al., "In vivo studies on the roles of Tic100, Tic40 and Hsp93 during chloroplast protein import," The Plant Journal, 41:412-428 (2005).

Li et at., "Long dsRNA but not siRNA initiates RNAi in western corn rootwmor larvae and adults," Journal of Applied Entomology, 139(6):432-445 (2015).

Liu, "Calmodulin and Cell Cycle," Foreign Medical Sciences Section of Pathophysiology and Clinical Medicine, 18(4):322-324 (1998).

Liu, "The Transformation of Nucleic Acid Degradants in Plants," China Organic Fertilizers, Agriculture Press, ISBN: 7-1091634 (with English translation) (1991).

Non-Final Office Action dated Mar. 21, 2018, in U.S. Appl. No. 13/619,980.

(56) References Cited

OTHER PUBLICATIONS

Office Action dated Aug. 9, 2018, in Canadian Patent Application No. 2,848,371.
Office Action dated Feb. 21, 2018, in Mexican Patent Application No, MX/a/2015/012632 (with English translation).
Office Action dated Jul. 30, 2018, in Canadian Patent Application No. 2,848,576.
Office Action dated Mar. 8, 2018 (with English translation), in Chilean Patent Application No. 201403192.
Paddison et al., "Stable suppression of gene expression by RNAi in mammalian cells," Proc. Natl Acad. Sci. USA, 99(3):1443-1448 (2002).
Partial Supplementary European Search Report dated Jan. 11, 2018, in European Patent Application No. 15812530.0.
Qichuan et al., Seed Science, China Agriculture Press, pp. 101-103, Tables 2-37 (2001).
Reverdatto et al., "A Multisubunit Acetyl Coenzyme A Carboxylase from Soybean," Plant Physiol., 119: 961-978 (1999).
Stevens, "Organosilicone Surfactants as Adjuvants for Agrochemicals," Journal of Pesticide Science, 38:103-122 (1993).
Stevens, "Formulation of Sprays to Improve the Efficacy of Foliar Fertilisers," New Zealand Forest Research Institute, pp. 27-34 (1994).
Sun, "Characterization of Organosilicone Surfactants and Their Effects on Sulfonylurea Herbicide Activity," Thesis Submitted to the Faculty of the Virginia Polytechnic Institute and Stale University dated Apr. 5. 1996.
Teng et al., "Tic21 Is an Essential Translocon Component for Protein Translocation across the Chloroplast Inner Envelope Membrane," The Plant Cell, 18:2247-2257 (2006).
Ulrich et al., "Large scale RNAi screen in Tribolium reveals novel target genes for pest control and the proteasome as prime target," BMC genomics, 16(1):671 (2015).
Wang et al., "Principle and technology of genetic engineering in plants," in Plant genetic engineering principles and techniques, Beijing: Science Press, pp. 313-315 (1998).
Zaimin et al., Chapter III Seeds and Seedlings, Botany, Northwest A&F University Press, pp. 87-92 (2009).
Zhong et al., "A pea antisense gene for the chloroplast stromal processing peptidase yields seedling lethals in *Arabidopsis*: survivors show defective GFP import in vivo," The Plant Journal, 34:802-812 (2003).
Zotti et al., "RNAi technology for insect management and protection of beneficial insects from diseases: lessons, challenges and risk assessments," Neotropical Entomology, 44(3):197-213 (2015).

* cited by examiner

SEQUENCE LISTING

<160> NUMBER OF SEQ ID NOS: 66

<210> SEQ ID NO 1
<211> LENGTH: 1557
<212> TYPE: DNA
<213> ORGANISM: Amaranthus palmeri

<400> SEQUENCE: 1

```
atggctcaag ctactaccat caacaatggt gtccatactg gtcaattgca ccatacttta      60
cccaaaaccc agttacccaa atcttcaaaa actcttaatt ttggatcaaa cttgagaatt     120
tctccaaagt tcatgtcttt aaccaataaa agagttggtg ggcaatcatc aattgttccc     180
aagattcaag cttctgttgc tgctgcagct gagaaacctt catctgtccc agaaattgtg     240
ttacaaccca tcaaagagat ctctggtact gttcaattgc ctgggtcaaa gtctttatcc     300
aatcgaatcc ttcttttagc tgctttgtct gagggcacaa cagtggtcga caacttgctg     360
tatagtgatg atattcttta tatgttggac gctctcagaa ctcttggttt aaaagtggag     420
gatgatagta cagccaaaag ggcagtcgta gagggttgtg gtggtctgtt tcctgttggt     480
aaagatggaa aggaagagat tcaactttc cttggtaatg caggaacagc gatgcgccca     540
ttgacagctg cggttgccgt tgctggagga aattcaagtt atgtgcttga tggagtacca     600
agaatgaggg agcgccccat tggggatctg gtagcaggtc taaagcaact tggttcagat     660
gtagattgtt ttcttggcac aaattgccct cctgttcggg tcaatgctaa aggaggcctt     720 ccaggggca aggtcaagct ctctggatcg gttagtagcc aatatttaac tgcacttctc     780
atggctactc ctttgggtct tggagacgtg gagattgaga tagttgataa attgatttct     840
gtaccgtatg ttgaaatgac aataaagttg atggaacgct ttggagtatc cgtagaacat     900
agtgatagtt gggacaggtt ctacattcga ggtggtcaga aatacaaatc tcctggaaag     960
gcatatgttg agggtgatgc ttcaagtgct agctacttcc tagccggagc cgccgtcact    1020
ggtgggactg tcactgtcaa gggttgtgga acaagcagtt tacagggtga tgtaaaattt    1080
gccgaagttc ttgagaagat gggttgcaag gtcacctgga cagagaatag tgtaactgtt    1140
actggaccac ccaggggattc atctggaaag aaacatctgc gtgctatcga cgtcaacatg    1200
aacaaaatgc cagatgttgc tatgactctt gcagttgttg ccttgtatgc agatgggccc    1260
accgccatca gagatgtggc tagctggaga gtgaaggaaa ccgaacggat gattgccatt    1320
tgcacagaac tgagaaagct tggggcaaca gttgaggaag gatctgatta ctgtgtgatc    1380
actccgcctg aaaagctaaa ccccaccgcc attgaaactt atgacgatca ccgaatggcc    1440
atggcattct ctcttgctgc ctgtgcagat gttcccgtca ctatccttga tccgggatgc    1500
acccgtaaaa ccttcccgga ctactttgat gttttagaaa agttcgccaa gcattga      1557
```

```
<210> SEQ ID NO 2
<211> LENGTH: 1557
<212> TYPE: DNA
<213> ORGANISM: Amaranthus rudis

<400> SEQUENCE: 2
atggctcaag ctactaccat caacaatggt gtccaaactg gtcaattgca ccatacttta      60
cccaaaaccc acttacccaa atcttcaaaa actgttaatt ttggatcaaa ctttagaatt     120
tctccaaagt tcatgtcttt aaccaataaa agagttggtg ggcaatcatc aattattccc     180
aagattcaag cttcagttgc tgctgcagct gagaaacctt catctgtccc agaaattgtg     240
ttacaaccca tcaaagagat ctctggtacc attcaattgc ctgggtcaaa gtctctatct     300
aatcgaatcc ttcttttagc tgctttgtct cagggcacaa ctgtggtcga caacttgctg     360
tatagtgatg atattcttta tatgttggac gctctcagaa ctcttggttt aaaagtggag     420
gatgataata cagacaaaag ggcagtcgtg gagggttgtg gtggtctgtt tcctgttggt     480
aaagatggaa aggaagagat tcaacttttc cttggaaatg caggaacagc gatgcgccca     540
ttgacagctg cggttgccgt tgctggagga aattcaagct atgttcttga cggagtacca     600
agaatgaggg agcgcccat tggggatctg gtagcaggtc taaagcaact tggttcagat     660
gttgactgtt ttcttggcac aaattgccct cctgttcggg tcaatgctaa aggaggcctt     720
ccagggggca aggtcaagct ctctggatcg gttagtagcc aatatttaac tgcacttctg     780
atggctactc ctttgggtct tggagatgtg gagattgaga tagttgataa attgatttcc     840
gtaccgtatg ttgaaatgac aataaggttg atggaacgct ttggagtatc tgttgaacat     900
agtgatagtt gggacaggtt cttcatccga ggtggtcaga atacaaatc tcctggaaag     960 gcatatgttg agggtgacgc ttcaagtgct agctacttcc tagctggagc cgccgtcact    1020 gggggggactg tgactgtcaa gggttgtgga acaagcagtt tacagggtga tgtaaaattt    1080
gccgaagttc ttgagaagat gggttgcaag gtcacctgga cagacaatag cgtaactgtt    1140
actggaccac ccagggaatc atctggaagg aaacatttgc gcgctatcga cgtcaacatg    1200
aataaaatgc cagatgttgc tatgactctt gcagttgttg ccttgtatgc agatgggccc    1260
accgccatta gagatgtggc tagctggaga gtgaaggaaa ccgaacggat gattgccatt    1320
tgcacagaac tgagaaagct tggggcaaca gttgaggaag gatctgatta ctgtgtgatc    1380
actccgcctg aaaagctgat acccaccgcc atcgaaactt atgacgatca ccgaatggcc    1440
atggcattct ctcttgctgc ctgtgctgat gttcccgtca ctatccttga tccgggatgt    1500
acacgtaaaa ccttcccgga ctactttgat gtcttagaaa agttcgccaa gcattga      1557

<210> SEQ ID NO 3
<211> LENGTH: 50
<212> TYPE: RNA
<213> ORGANISM: artificial sequence
<220> FEATURE:
<223> OTHER INFORMATION: synthetic sequence

<400> SEQUENCE: 3
gaacucuugg uuuaaaagug gaggaugaua guacagccaa aagggcaguc                 50

<210> SEQ ID NO 4
<211> LENGTH: 50
<212> TYPE: RNA
<213> ORGANISM: artificial sequence
<220> FEATURE:
<223> OTHER INFORMATION: synthetic sequence
```

```
<400> SEQUENCE: 4
gacugcccuu uuggcuguac uaucauccuc cacuuuuaaa ccaagaguuc                 50

<210> SEQ ID NO 5
<211> LENGTH: 53
<212> TYPE: RNA
<213> ORGANISM: artificial sequence
<220> FEATURE:
<223> OTHER INFORMATION: synthetic sequence

<400> SEQUENCE: 5
gacgucaaca ugaacaaaau gccagauguu gcuaugacuc uugcaguugu ugc             53

<210> SEQ ID NO 6
<211> LENGTH: 53
<212> TYPE: RNA
<213> ORGANISM: artificial sequence
<220> FEATURE:
<223> OTHER INFORMATION: synthetic sequence

<400> SEQUENCE: 6
gcaacaacug caagagucau agcaacaucu ggcauuuugu ucauguugac guc             53

<210> SEQ ID NO 7
<211> LENGTH: 24
<212> TYPE: RNA
<213> ORGANISM: artificial sequence
<220> FEATURE:
<223> OTHER INFORMATION: synthetic sequence

<400> SEQUENCE: 7
augccagaug uugcuaugac ucuu                                             24

<210> SEQ ID NO 8
<211> LENGTH: 24
<212> TYPE: RNA
<213> ORGANISM: artificial sequence
<220> FEATURE:
<223> OTHER INFORMATION: synthetic sequence

<400> SEQUENCE: 8
aagagucaua gcaacaucug gcau                                             24

<210> SEQ ID NO 9
<211> LENGTH: 49
<212> TYPE: DNA
<213> ORGANISM: artificial sequence
<220> FEATURE:
<223> OTHER INFORMATION: synthetic sequence

<400> SEQUENCE: 9
gagctcttgg tttaaaagtg gaggatgata atacagccaa aagggcagt                  49

<210> SEQ ID NO 10
<211> LENGTH: 50
<212> TYPE: DNA
<213> ORGANISM: artificial sequence
<220> FEATURE:
<223> OTHER INFORMATION: synthetic sequence

<400> SEQUENCE: 10
gaactcttgg tttaaaagtg gaggatgata atacagccaa aagggcagtc                 50

<210> SEQ ID NO 11
<211> LENGTH: 50
```

```
<212> TYPE: DNA
<213> ORGANISM: artificial sequence
<220> FEATURE:
<223> OTHER INFORMATION: synthetic sequence

<400> SEQUENCE: 11
gaactcttgg tttaaaagtg gaggatgata gtacagccaa aagggcagtc                50

<210> SEQ ID NO 12
<211> LENGTH: 50
<212> TYPE: DNA
<213> ORGANISM: artificial sequence
<220> FEATURE:
<223> OTHER INFORMATION: synthetic sequence

<400> SEQUENCE: 12
gaactcttgg tttaaaagtg gaggatgata atacagacaa aagggcagtc                50

<210> SEQ ID NO 13
<211> LENGTH: 50
<212> TYPE: DNA
<213> ORGANISM: artificial sequence
<220> FEATURE:
<223> OTHER INFORMATION: synthetic sequence

<400> SEQUENCE: 13
gaactcttgg tttaaaagtg gaggatgata atacagccaa aagggcagtc                50

<210> SEQ ID NO 14
<211> LENGTH: 53
<212> TYPE: DNA
<213> ORGANISM: artificial sequence
<220> FEATURE:
<223> OTHER INFORMATION: synthetic sequence

<400> SEQUENCE: 14
gatgtcaaca tgaacaaaat gccagatgtt gccatgactc tcgctgttgt tgc           53

<210> SEQ ID NO 15
<211> LENGTH: 53
<212> TYPE: DNA
<213> ORGANISM: artificial sequence
<220> FEATURE:
<223> OTHER INFORMATION: synthetic sequence

<400> SEQUENCE: 15
gacgtcaaca tgaacaaaat gccagatgtt gctatgactc ttgcagttgt tgc           53

<210> SEQ ID NO 16
<211> LENGTH: 53
<212> TYPE: DNA
<213> ORGANISM: artificial sequence
<220> FEATURE:
<223> OTHER INFORMATION: synthetic sequence

<400> SEQUENCE: 16
gacgtcaaca tgaacaaaat gccagatgtt gctatgactc ttgcagtagt tgc           53

<210> SEQ ID NO 17
<211> LENGTH: 53
<212> TYPE: DNA
<213> ORGANISM: artificial sequence
<220> FEATURE:
<223> OTHER INFORMATION: synthetic sequence

<400> SEQUENCE: 17
```
gacgtcaaca tgaacaaaat gccagatgtt gctatgactc ttgcagtagt tgc        53

<210> SEQ ID NO 18
<211> LENGTH: 53
<212> TYPE: DNA
<213> ORGANISM: artificial sequence
<220> FEATURE:
<223> OTHER INFORMATION: synthetic sequence

<400> SEQUENCE: 18
gacgtcaaca tgaacaaaat gccagatgtt gctatgactc ttgcagttgt tgc        53

<210> SEQ ID NO 19
<211> LENGTH: 53
<212> TYPE: DNA
<213> ORGANISM: artificial sequence
<220> FEATURE:
<223> OTHER INFORMATION: synthetic sequence

<400> SEQUENCE: 19
gacgtcaaca tgaataaaat gccagatgtt gctatgactc ttgcagttgt tgc        53

<210> SEQ ID NO 20
<211> LENGTH: 53
<212> TYPE: DNA
<213> ORGANISM: artificial sequence
<220> FEATURE:
<223> OTHER INFORMATION: synthetic sequence

<400> SEQUENCE: 20
gacgtcaaca tgaacaaaat gccagatgtt gctatgactc ttgcagtagt tgc        53

<210> SEQ ID NO 21
<211> LENGTH: 53
<212> TYPE: DNA
<213> ORGANISM: artificial sequence
<220> FEATURE:
<223> OTHER INFORMATION: synthetic sequence

<400> SEQUENCE: 21
gacgtcaaca tgaacaaaat gccagatgtt gctatgactc ttgcagtagt tgc        53

<210> SEQ ID NO 22
<211> LENGTH: 53
<212> TYPE: DNA
<213> ORGANISM: artificial sequence
<220> FEATURE:
<223> OTHER INFORMATION: synthetic sequence

<400> SEQUENCE: 22
gatgttaaca tgaacaaaat gccagatgtt gccatgacgc ttgcagtcgt tgc        53

<210> SEQ ID NO 23
<211> LENGTH: 53
<212> TYPE: DNA
<213> ORGANISM: artificial sequence
<220> FEATURE:
<223> OTHER INFORMATION: synthetic sequence

<400> SEQUENCE: 23
gatgtcaaca tgaacaaaat gccagatgtc gctatgactc ttgctgttgt tgc        53

<210> SEQ ID NO 24
<211> LENGTH: 53
<212> TYPE: DNA
<213> ORGANISM: artificial sequence
<220> FEATURE:
<223> OTHER INFORMATION: synthetic sequence

<400> SEQUENCE: 24
gatgtcaaca tgaataaaat gccagatgtc gccatgactc ttgctgtagt tgc         53

<210> SEQ ID NO 25
<211> LENGTH: 53
<212> TYPE: DNA
<213> ORGANISM: artificial sequence
<220> FEATURE:
<223> OTHER INFORMATION: synthetic sequence

<400> SEQUENCE: 25
gatgtgaaca tgaacaagat gcctgatgtt gccatgactc ttgctgtggt cgc         53

<210> SEQ ID NO 26
<211> LENGTH: 53
<212> TYPE: DNA
<213> ORGANISM: artificial sequence
<220> FEATURE:
<223> OTHER INFORMATION: synthetic sequence

<400> SEQUENCE: 26
gatgttaaca tgaacaaaat gcccgatgtt gccatgactc ttgccgtggt tgc         53

<210> SEQ ID NO 27
<211> LENGTH: 53
<212> TYPE: DNA
<213> ORGANISM: artificial sequence
<220> FEATURE:
<223> OTHER INFORMATION: synthetic sequence

<400> SEQUENCE: 27
gacgtcaaca tgaacaaaat gcctgatgtc gcaatgactc ttgctgtggt tgc         53

<210> SEQ ID NO 28
<211> LENGTH: 53
<212> TYPE: DNA
<213> ORGANISM: artificial sequence
<220> FEATURE:
<223> OTHER INFORMATION: synthetic sequence

<400> SEQUENCE: 28
gatgtcaaca tgaacaaaat gcctgatgtt gccatgactc ttgctgtggt cgc         53

<210> SEQ ID NO 29
<211> LENGTH: 53
<212> TYPE: DNA
<213> ORGANISM: artificial sequence
<220> FEATURE:
<223> OTHER INFORMATION: synthetic sequence

<400> SEQUENCE: 29
gatgtcaaca tgaacaaaat gcctgatgtt gccatgactc ttgctgtggt cgc         53

<210> SEQ ID NO 30
<211> LENGTH: 53
<212> TYPE: DNA
<213> ORGANISM: artificial sequence
<220> FEATURE:
<223> OTHER INFORMATION: synthetic sequence

<400> SEQUENCE: 30
gatgtgaaca tgaacaaaat gccagatgtc gctatgacat tggctgtggt tgc         53

<210> SEQ ID NO 31
<211> LENGTH: 53
<212> TYPE: DNA
<213> ORGANISM: artificial sequence
<220> FEATURE:
<223> OTHER INFORMATION: synthetic sequence

<400> SEQUENCE: 31
gatgtcaaca tgaacaaaat gccagatgtt gccatgactc ttgctgtagt tgc    53

<210> SEQ ID NO 32
<211> LENGTH: 53
<212> TYPE: DNA
<213> ORGANISM: artificial sequence
<220> FEATURE:
<223> OTHER INFORMATION: synthetic sequence

<400> SEQUENCE: 32
gatgtcaaca tgaacaaaat gcctgatgtt gccatgactc ttgccgttgt tgc    53

<210> SEQ ID NO 33
<211> LENGTH: 53
<212> TYPE: DNA
<213> ORGANISM: artificial sequence
<220> FEATURE:
<223> OTHER INFORMATION: synthetic sequence

<400> SEQUENCE: 33
gatgtcaaca tgaacaagat gccagatgtt gccatgactc ttgctgtagt tgc    53

<210> SEQ ID NO 34
<211> LENGTH: 53
<212> TYPE: DNA
<213> ORGANISM: artificial sequence
<220> FEATURE:
<223> OTHER INFORMATION: synthetic sequence

<400> SEQUENCE: 34
gatgttaaca tgaacaaaat gcctgatgtt gccatgactc ttgctgtggt tgc    53

<210> SEQ ID NO 35
<211> LENGTH: 53
<212> TYPE: DNA
<213> ORGANISM: artificial sequence
<220> FEATURE:
<223> OTHER INFORMATION: synthetic sequence

<400> SEQUENCE: 35
gatgttaaca tgaacaaaat gccagatgtt gccatgacgc ttgcagtcgt tgc    53

<210> SEQ ID NO 36
<211> LENGTH: 49
<212> TYPE: DNA
<213> ORGANISM: artificial sequence
<220> FEATURE:
<223> OTHER INFORMATION: synthetic sequence

<400> SEQUENCE: 36
gctcaagcta ctaccatcaa caatggtgtc catactggtc aattgcacc    49

<210> SEQ ID NO 37
<211> LENGTH: 60
<212> TYPE: DNA
<213> ORGANISM: artificial sequence
<220> FEATURE:
<223> OTHER INFORMATION: synthetic sequence

```
<400> SEQUENCE: 37
gcaccatact ttacccaaaa cccagttacc caaatcttca aaaactctta attttggatc      60

<210> SEQ ID NO 38
<211> LENGTH: 60
<212> TYPE: DNA
<213> ORGANISM: artificial sequence
<220> FEATURE:
<223> OTHER INFORMATION: synthetic sequence

<400> SEQUENCE: 38
gatcaaactt gagaatttct ccaaagttca tgtctttaac caataaaaga gttggtgggc      60

<210> SEQ ID NO 39
<211> LENGTH: 48
<212> TYPE: DNA
<213> ORGANISM: artificial sequence
<220> FEATURE:
<223> OTHER INFORMATION: synthetic sequence

<400> SEQUENCE: 39
gcaatcatca attgttccca agattcaagc ttctgttgct gctgcagc                  48

<210> SEQ ID NO 40
<211> LENGTH: 54
<212> TYPE: DNA
<213> ORGANISM: artificial sequence
<220> FEATURE:
<223> OTHER INFORMATION: synthetic sequence

<400> SEQUENCE: 40
gctgagaaac cttcatctgt cccagaaatt gtgttacaac ccatcaaaga gatc            54

<210> SEQ ID NO 41
<211> LENGTH: 52
<212> TYPE: DNA
<213> ORGANISM: artificial sequence
<220> FEATURE:
<223> OTHER INFORMATION: synthetic sequence

<400> SEQUENCE: 41
gatctctggt actgttcaat tgcctgggtc aaagtcttta tccaatcgaa tc              52

<210> SEQ ID NO 42
<211> LENGTH: 54
<212> TYPE: DNA
<213> ORGANISM: artificial sequence
<220> FEATURE:
<223> OTHER INFORMATION: synthetic sequence

<400> SEQUENCE: 42
gaatccttct tttagctgct ttgtctgagg gcacaacagt ggtcgacaac ttgc            54

<210> SEQ ID NO 43
<211> LENGTH: 47
<212> TYPE: DNA
<213> ORGANISM: artificial sequence
<220> FEATURE:
<223> OTHER INFORMATION: synthetic sequence

<400> SEQUENCE: 43
gctgtatagt gatgatattc tttatatgtt ggacgctctc agaactc                   47

<210> SEQ ID NO 44
```

<211> LENGTH: 61
<212> TYPE: DNA
<213> ORGANISM: artificial sequence
<220> FEATURE:
<223> OTHER INFORMATION: synthetic sequence

<400> SEQUENCE: 44
gcagtcgtag agggttgtgg tggtctgttt cctgttggta aagatggaaa ggaagagatt    60
c                                                                   61

<210> SEQ ID NO 45
<211> LENGTH: 48
<212> TYPE: DNA
<213> ORGANISM: artificial sequence
<220> FEATURE:
<223> OTHER INFORMATION: synthetic sequence

<400> SEQUENCE: 45
gattcaactt ttccttggta atgcaggaac agcgatgcgc ccattgac                 48

<210> SEQ ID NO 46
<211> LENGTH: 56
<212> TYPE: DNA
<213> ORGANISM: artificial sequence
<220> FEATURE:
<223> OTHER INFORMATION: synthetic sequence

<400> SEQUENCE: 46
gacagctgcg gttgccgttg ctggaggaaa ttcaagttat gtgcttgatg gagtac        56

<210> SEQ ID NO 47
<211> LENGTH: 52
<212> TYPE: DNA
<213> ORGANISM: artificial sequence
<220> FEATURE:
<223> OTHER INFORMATION: synthetic sequence

<400> SEQUENCE: 47
gtaccaagaa tgagggagcg ccccattggg gatctggtag caggtctaaa gc            52

<210> SEQ ID NO 48
<211> LENGTH: 53
<212> TYPE: DNA
<213> ORGANISM: artificial sequence
<220> FEATURE:
<223> OTHER INFORMATION: synthetic sequence

<400> SEQUENCE: 48
gcaacttggt tcagatgtag attgttttct tggcacaaat tgccctcctg ttc           53

<210> SEQ ID NO 49
<211> LENGTH: 56
<212> TYPE: DNA
<213> ORGANISM: artificial sequence
<220> FEATURE:
<223> OTHER INFORMATION: synthetic sequence

<400> SEQUENCE: 49
gttcgggtca atgctaaagg aggccttcca gggggcaagg tcaagctctc tggatc        56

<210> SEQ ID NO 50
<211> LENGTH: 54
<212> TYPE: DNA
<213> ORGANISM: artificial sequence
<220> FEATURE:
<223> OTHER INFORMATION: synthetic sequence

```
<400> SEQUENCE: 50
gatcggttag tagccaatat ttaactgcac ttctcatggc tactcctttg ggtc        54

<210> SEQ ID NO 51
<211> LENGTH: 48
<212> TYPE: DNA
<213> ORGANISM: artificial sequence
<220> FEATURE:
<223> OTHER INFORMATION: synthetic sequence

<400> SEQUENCE: 51
gtcttggaga cgtggagatt gagatagttg ataaattgat ttctgtac              48

<210> SEQ ID NO 52
<211> LENGTH: 58
<212> TYPE: DNA
<213> ORGANISM: artificial sequence
<220> FEATURE:
<223> OTHER INFORMATION: synthetic sequence

<400> SEQUENCE: 52
gtaccgtatg ttgaaatgac aataaagttg atggaacgct ttggagtatc cgtagaac   58

<210> SEQ ID NO 53
<211> LENGTH: 51
<212> TYPE: DNA
<213> ORGANISM: artificial sequence
<220> FEATURE:
<223> OTHER INFORMATION: synthetic sequence

<400> SEQUENCE: 53
gaacatagtg atagttggga caggttctac attcgaggtg gtcagaaata c          51

<210> SEQ ID NO 54
<211> LENGTH: 55
<212> TYPE: DNA
<213> ORGANISM: artificial sequence
<220> FEATURE:
<223> OTHER INFORMATION: synthetic sequence

<400> SEQUENCE: 54
gtcagaaata caaatctcct ggaaaggcat atgttgaggg tgatgcttca agtgc      55

<210> SEQ ID NO 55
<211> LENGTH: 51
<212> TYPE: DNA
<213> ORGANISM: artificial sequence
<220> FEATURE:
<223> OTHER INFORMATION: synthetic sequence

<400> SEQUENCE: 55
gctagctact tcctagccgg agccgccgtc actggtggga ctgtcactgt c          51

<210> SEQ ID NO 56
<211> LENGTH: 56
<212> TYPE: DNA
<213> ORGANISM: artificial sequence
<220> FEATURE:
<223> OTHER INFORMATION: synthetic sequence

<400> SEQUENCE: 56
gttcttgaga agatgggttg caaggtcacc tggacagaga atagtgtaac tgttac     56

<210> SEQ ID NO 57
```

```
<211> LENGTH: 56
<212> TYPE: DNA
<213> ORGANISM: artificial sequence
<220> FEATURE:
<223> OTHER INFORMATION: synthetic sequence

<400> SEQUENCE: 57
gttcttgaga agatgggttg caaggtcacc tggacagaga atagtgtaac tgttac      56

<210> SEQ ID NO 58
<211> LENGTH: 54
<212> TYPE: DNA
<213> ORGANISM: artificial sequence
<220> FEATURE:
<223> OTHER INFORMATION: synthetic sequence

<400> SEQUENCE: 58
gttactggac cacccaggga ttcatctgga agaaacatc tgcgtgctat cgac         54

<210> SEQ ID NO 59
<211> LENGTH: 62
<212> TYPE: DNA
<213> ORGANISM: artificial sequence
<220> FEATURE:
<223> OTHER INFORMATION: synthetic sequence

<400> SEQUENCE: 59
gccttgtatg cagatgggcc caccgccatc agagatgtgg ctagctggag agtgaaggaa   60
ac                                                                 62

<210> SEQ ID NO 60
<211> LENGTH: 50
<212> TYPE: DNA
<213> ORGANISM: artificial sequence
<220> FEATURE:
<223> OTHER INFORMATION: synthetic sequence

<400> SEQUENCE: 60
gaaaccgaac ggatgattgc catttgcaca gaactgagaa agcttggggc              50

<210> SEQ ID NO 61
<211> LENGTH: 52
<212> TYPE: DNA
<213> ORGANISM: artificial sequence
<220> FEATURE:
<223> OTHER INFORMATION: synthetic sequence

<400> SEQUENCE: 61
gcaacagttg aggaaggatc tgattactgt gtgatcactc cgcctgaaaa gc           52

<210> SEQ ID NO 62
<211> LENGTH: 51
<212> TYPE: DNA
<213> ORGANISM: artificial sequence
<220> FEATURE:
<223> OTHER INFORMATION: synthetic sequence

<400> SEQUENCE: 62
gctaaacccc accgccattg aaacttatga cgatcaccga atggccatgg c            51

<210> SEQ ID NO 63
<211> LENGTH: 57
<212> TYPE: DNA
<213> ORGANISM: artificial sequence
<220> FEATURE:
<223> OTHER INFORMATION: synthetic sequence
```

-continued

```
<400> SEQUENCE: 63
gcattctctc ttgctgcctg tgcagatgtt cccgtcacta tccttgatcc gggatgc         57

<210> SEQ ID NO 64
<211> LENGTH: 54
<212> TYPE: DNA
<213> ORGANISM: artificial sequence
<220> FEATURE:
<223> OTHER INFORMATION: synthetic sequence

<400> SEQUENCE: 64
gcacccgtaa aaccttcccg gactactttg atgttttaga aaagttcgcc aagc           54

<210> SEQ ID NO 65
<211> LENGTH: 50
<212> TYPE: DNA
<213> ORGANISM: artificial sequence
<220> FEATURE:
<223> OTHER INFORMATION: synthetic sequence

<400> SEQUENCE: 65
gaactcttgg tttaaaagtg gaggatgata gtacagccaa aagggcagtc                50

<210> SEQ ID NO 66
<211> LENGTH: 53
<212> TYPE: DNA
<213> ORGANISM: artificial sequence
<220> FEATURE:
<223> OTHER INFORMATION: synthetic sequence

<400> SEQUENCE: 66
gacgtcaaca tgaacaaaat gccagatgtt gctatgactc ttgcagttgt tgc            53
```

METHODS AND COMPOSITIONS FOR WEED CONTROL USING EPSPS POLYNUCLEOTIDES

CROSS-REFERENCE TO RELATED APPLICATIONS

This application is a U.S. National Stage Application of PCT/US2015/011408, filed on Jan. 14, 2015, which claims the benefit of U.S. Provisional Application No. 61/927,682, filed on Jan. 15, 2014, which is incorporated by reference in its entirety herein.

INCORPORATION OF SEQUENCE LISTING

A computer readable form of a sequence listing is filed with this application by electronic submission and is incorporated into this application by reference in its entirety. The sequence listing is contained in the file named P34158US01_SEQ.txt, which is 16,933 bytes in size (measured in operating system MS windows) and was created on Jul. 14, 2016.

FIELD

The embodiments relate generally to the field of weed management. More specifically, embodiments relate compositions and methods for controlling weed species utalizing polynucleotide molecules. Further provided are compositions containing polynucleotide molecules and methods of utilizing such compositions for altering the physiology of plants and modulating the effect of herbicide treatment.

BACKGROUND

Weeds are plants that are unwanted in a particular environment. For example, in an agronomic environment, weeds are plants that compete with cultivated plants. Weeds can also serve as hosts for crop diseases and insect pests. In agricultural production environments, weeds can cause decreases in crop yield, reduced crop quality, increased irrigation costs, increased harvesting costs, reduced land value, injury to livestock, and crop damage from insects and diseases harbored by the weeds. The principal means by which weeds cause these effects are: 1) competing with crop plants for water, nutrients, sunlight and other essentials for growth and development, 2) production of toxic or irritant chemicals that cause human or animal health problems, 3) production of immense quantities of seed or vegetative reproductive parts or both that contaminate agricultural products and perpetuate the weed species in agricultural lands, and 4) production on agricultural and nonagricultural lands of vast amounts of vegetation requiring disposal. Weeds cost farmers billions of dollars annually in crop losses and weed control expenses.

Chemical herbicides are often used to control the growth and spread of weeds. Chemical herbicides are active at one or more target sites within a plant where they interrupt normal plant functions. For example, the herbicide N-phosphonomethyl glycine, also known as glyphosate, targets EPSPS (5-enolpyruvylshikimate-3-phosphate synthase), the enzyme that catalyzes the conversion of shikimate-3-phosphate into 5-enolpyruvyl-shikimate-3-phosphate, which is an intermediate in the biochemical pathway for creating three essential aromatic amino acids (tyrosine, phenylalanine, and tryptophan).

One limitation on the use of chemical herbicides to control weeds is the emergence of herbicide-resistant weeds. Herbicide resistance is the ability of a plant to survive and reproduce following exposure to a dose of herbicide that would normally be lethal. In weeds, herbicide resistance may occur naturally as the result of random and infrequent mutations. Where chemical herbicide application provides selection pressure, herbicide resistant plants survive to reproduce without competition from herbicide-susceptible plants. This selective pressure can lead to the appearance of increasing numbers of herbicide resistant weeds in a weed population. Herbicide tolerant weeds have been observed for nearly all herbicides in use. There are over 365 weed biotypes currently identified as being herbicide resistant to one or more herbicides by the Herbicide Resistance Action Committee (HRAC), the North American Herbicide Resistance Action Committee (NAHRAC), and the Weed Science Society of America (WSSA). There is a need to effectively manage these herbicide resistant weeds and to provide new compositions and techniques for weed management.

SUMMARY

The present embodiments relate to compositions and methods useful for sensitizing weeds to herbicides targeting 5-enolpyruvylshikimate-3-phosphate synthase (EPSPS) for the purpose of enhancing control of weeds and for the management of herbicide resistant weeds.

Several embodiments relate to a bioactive trigger polynucleotide comprising a nucleotide sequence that is essentially identical or essentially complementary to SEQ ID NOs: 3, 5, or 9-66, or a fragment thereof. The bioactive trigger polynucleotide may be a single-stranded DNA, a single-stranded RNA, a double-stranded RNA, a double-stranded DNA, or a double-stranded DNA/RNA hybrid. In several embodiments, the bioactive trigger polynucleotide comprises a nucleotide sequence that is essentially identical or essentially complementary to SEQ ID NO 3 or SEQ ID NO 5. In some embodiments, the bioactive trigger polynucleotide comprises a nucleotide sequence that is essentially identical or essentially complementary to a sequence selected from the group consisting of SEQ ID NO: 36, SEQ ID NO: 42, SEQ ID NO: 43, SEQ ID NO: 44, SEQ ID NO: 57, SEQ ID NO: 58, SEQ ID NO: 59, SEQ ID NO: 65, SEQ ID NO: 66, or a fragment thereof. In some embodiments, the bioactive trigger polynucleotide is double-stranded RNA and the double-stranded RNA comprises SEQ ID NOs: 3 and 4. In some embodiments, the bioactive trigger polynucleotide is double-stranded RNA and the double-stranded RNA comprises SEQ ID NOs: 5 and 6. Several embodiments relate to plant cell comprising a bioactive trigger polynucleotide as described herein. Several embodiments relate to plant comprising a bioactive trigger polynucleotide as described herein.

Several embodiments relate to a composition comprising one or more bioactive trigger polynucleotides and a transfer agent, wherein one or more bioactive trigger polynucleotides comprises a nucleotide sequence that is essentially identical or essentially complementary to SEQ ID NO: 3, 5, or 9-66, or a fragment thereof. The one or more bioactive trigger polynucleotides may each, independently, be selected from the group consisting of single-stranded DNA, single-stranded RNA, double-stranded RNA, double-stranded DNA, and double-stranded DNA/RNA hybrids. In some embodiments, the composition comprises one or more bioactive trigger polynucleotides comprising a nucleotide sequence that is essentially identical or essentially complementary to a sequence selected from the group consisting of SEQ ID NO: 36, SEQ ID NO: 42, SEQ ID NO: 43, SEQ ID NO: 44, SEQ ID NO: 57, SEQ ID NO: 58, SEQ ID NO: 59, SEQ ID NO: 65, SEQ ID NO: 66, or a fragment thereof. In some embodiments, the composition comprises one or more bioactive trigger polynucleotides comprising a nucleotide sequence that is essentially identical or essentially complementary to SEQ ID NO: 3 or SEQ ID NO: 5, or a fragment thereof. In some embodiments, the composition comprises one or more bioactive double-stranded RNA trigger polynucleotides comprising SEQ ID NOs: 3 and 4, or fragments thereof. In some embodiments, the composition comprises one or more bioactive double-stranded RNA trigger polynucleotides comprising SEQ ID NOs: 5 and 6, or fragments thereof. In some embodiments, the composition comprises a first bioactive trigger polynucleotide and one or more additional bioactive trigger polynucleotides that comprise a different nucleotide sequence than the first bioactive trigger polynucleotide. In some embodiments, the composition comprises a bioactive trigger polynucleotides that comprises a nucleotide sequence that is essentially identical or essentially complementary to SEQ ID NO: 3, 5, or 9-66 and a bioactive trigger molecule that is not essentially identical or essentially complementary to an EPSPS gene sequence, or to the RNA transcript of the EPSPS gene sequence. The composition can include various components. For example, the composition can include one or more of bioactive trigger polynucleotides, transfer agents, and non-polynucleotide herbicides. In some embodiments, the transfer agent is selected from the group consisting of a surfactant, such as an organosilicone surfactant, a cationic liposomal reagent and a plant hormone, such as Brassinosteroid. Examples of organosilicone surfactants include, but are not limited to, BREAK-THRU® S 321, BREAK-THRU® S 200, BREAK-THRU® OE 441, BREAK-THRU® S 278, BREAK-THRU® S 243, SILWET L-77®, SILWET® HS 429, SILWET® HS 312, and BREAK-THRU® S 233. In some embodiments, the composition comprises an organosilicone surfactant and ammonium sulfate. In some embodiments, the composition comprises DOTAP. In some embodiments, the composition comprises a cationic lipid. In some embodiments, the composition comprises nucleic acid lipid particles. In some embodiments, the composition comprises an EPSPS-inhibitor herbicide, such as glyphosate. In some embodiments, the composition comprises a non-EPSPS-inhibitor herbicide, such as dicamba or 2,4-D.

Several embodiments relate to a method of plant control, comprising applying a bioactive trigger polynucleotide comprising a nucleotide sequence that is essentially identical or essentially complementary to an EPSPS gene sequence, or to the RNA transcript of the EPSPS gene sequence, to an external surface of a plant, plant part or seed, wherein the plant is not mechanically permiabilized and the bioactive trigger polynucleotide is incorporated into the interior of a plant cell. Examples of plants that may be controlled by such methods include, but are not limited to, *Amaranthus palmeri*, *Amaranthus rudis*, *Amaranthus albus*, *Amaranthus chlorostachys*, *Amaranthus graecizans*, *Amaranthus hybridus*, *Amaranthus lividus*, *Amaranthus spinosus*, *Amaranthus thunbergii*, *Amaranthus viridis*, *Lolium multiflorum*, *Lolium rigidium*, *Ambrosia artemisiifolia*, *Ambrosia trifida*, *Euphorbia heterophylla*, *Kochia scoparia*, *Abutilon theophrasti*, *Sorghum halepense*, *Chenopodium album*, *Commelina diffusa*, *Convulvulus arvensis*, *Conyza candensis*, *Digitaria sanguinalis*, and *Xanthium strumarium*. In some embodiments, the EPSPS gene sequence is selected from SEQ ID NOs: 1 or 2, or a fragment thereof. In some embodiments, the EPSPS gene sequence is selected from SEQ ID NOs: 9-66. In some embodiments, the EPSPS gene sequence is selected from SEQ ID NO 36, SEQ ID NO 42, SEQ ID NO 43, SEQ ID NO 44, SEQ ID NO 57, SEQ ID NO 58, SEQ ID NO 59, SEQ ID NO 65, and SEQ ID NO 66. In some embodiments, the bioactive trigger polynucleotide comprises a nucleotide sequence that is essentially identical or essentially complementary to SEQ ID NO: 3, 5, or 9-66, or a fragment thereof. In some embodiments, the bioactive trigger polynucleotide is selected from the group consisting of single-stranded DNA, single-stranded RNA, double-stranded RNA, double-stranded DNA, and double-stranded DNA/RNA hybrids. In some embodiments, the bioactive trigger polynucleotide comprises a nucleotide sequence that is essentially identical or essentially complementary to SEQ ID NO 3 or SEQ ID NO 5, or a fragment thereof. In some embodiments, the bioactive trigger polynucleotide is double-stranded RNA comprising SEQ ID NOs: 3 and 4, or fragments thereof. In some embodiments, the bioactive trigger polynucleotide is double-stranded RNA comprising SEQ ID NOs: 5 and 6, or fragments thereof. In some embodiments of the method, a first bioactive trigger polynucleotide and one or more additional bioactive trigger polynucleotides that comprise a different nucleotide sequence than the first bioactive trigger polynucleotide is applied to the plant. In some embodiments, a bioactive trigger polynucleotide that comprises a nucleotide sequence that is essentially identical or essentially complementary to SEQ ID NO: 3, 5, or 9-66 and a bioactive trigger molecule that is not essentially identical or essentially complementary to an EPSPS gene sequence, or to the RNA transcript of the EPSPS gene sequence is applied to the plant. The method may further comprise applying one or more of a transfer agent, an EPSPS-inhibitor herbicide and other non-polynucleotide herbicides. Examples of transfer agents include, but are not limited to, surfactants, such as organosilicone surfactants, cationic lipid reagents, and plant hormones, such as Brassinosteroid. In some embodiments, the composition further comprises a non-polynucleotide herbicide. In some embodiments, the non-polynucleotide herbicide is glyphosate. In some embodiments, the non-polynucleotide herbicide is applied separately from the bioactive trigger polynucleotide. In some embodiments, the non-polynucleotide herbicide is applied concurrently with the bioactive trigger polynucleotide.

Several embodiments relate to a method of controlling growth, development or reproductive ability of a plant by topically treating the plant with a composition comprising a bioactive trigger polynucleotide and a transfer agent, wherein the bioactive trigger polynucleotide comprises a nucleotide sequence that is essentially identical or essentially complementary to SEQ ID NO: 3, 5, or 9-66, or a fragment thereof, whereby the growth, development or reproductive ability of the plant is reduced. In some embodiments, the bioactive trigger polynucleotide is selected from the group consisting of single-stranded DNA, single-stranded RNA, double-stranded RNA, double-stranded DNA, and double-stranded DNA/RNA hybrids. In some embodiments, the bioactive trigger polynucleotide comprises a nucleotide sequence that is essentially identical or essentially complementary to SEQ ID NO 3 or SEQ ID NO 5, or a fragment thereof. In some embodiments, the bioactive trigger polynucleotide comprises a nucleotide sequence that is essentially identical or essentially complementary to a sequence selected from the group consisting of SEQ ID NO 36, SEQ ID NO 42, SEQ ID NO 43, SEQ ID NO 44, SEQ ID NO 57, SEQ ID NO 58, SEQ ID NO 59, SEQ ID NO 65, SEQ ID NO 66, or a fragment thereof. In some embodiments, the bioactive trigger polynucleotide is double-stranded RNA comprising SEQ ID NOs: 3 and 4, or fragments thereof. In some embodiments, the bioactive trigger polynucleotide is double-stranded RNA comprising SEQ ID NOs: 5 and 6, or fragments thereof. In some embodiments of the method, the plant is treated with a first bioactive trigger polynucleotide and one or more additional bioactive trigger polynucleotides that comprise a different nucleotide sequence than the first bioactive trigger polynucleotide. In some embodiments, the plant is treated with a bioactive trigger polynucleotide that comprises a nucleotide sequence that is essentially identical or essentially complementary to SEQ ID NO: 3, 5, or 9-66 and a bioactive trigger molecule that is not essentially identical or essentially complementary to an EPSPS gene sequence, or to the RNA transcript of the EPSPS gene sequence. The method may further comprise treating the plant with one or more of a transfer agent, an EPSPS-inhibitor herbicide and other non-polynucleotide herbicides. Examples of transfer agents include, but are not limited to, surfactants, such as organosilicone surfactants, cationic lipid reagents, and plant hormones, such as Brassinosteroid. In some embodiments, the plant is treated with a non-polynucleotide herbicide. In some embodiments, the non-polynucleotide herbicide is glyphosate. In some embodiments, the non-polynucleotide herbicide is applied separately from the bioactive trigger polynucleotide. In some embodiments, the non-polynucleotide herbicide is applied concurrently with the bioactive trigger polynucleotide.

Several embodiments relate to a method of sensitizing a weed to an EPSPS-inhibitor herbicide, comprising treating the weed with a bioactive trigger polynucleotide that is essentially identical or essentially complementary to a nucleotide sequence selected from the group consisting of SEQ ID NO:3, 5, and 9-66, or a fragment thereof, whereby the weed is more sensitive to an EPSPS-inhibitor herbicide relative to a weed not treated with the bioactive trigger polynucleotide. In some embodiments, the bioactive trigger polynucleotide is essentially identical or essentially complementary to a nucleotide sequence selected from the group consisting of SEQ ID NO 36, SEQ ID NO 42, SEQ ID NO 43, SEQ ID NO 44, SEQ ID NO 57, SEQ ID NO 58, SEQ ID NO 59, SEQ ID NO 65, SEQ ID NO 66, or a fragment thereof. In some embodiments, the method further comprises treating the plant with an EPSPS-inhibitor herbicide. In some embodiments, the weed is resistant to one or more of glyphosate, dicamba and sulfonylurea. In some embodiments, the weed is selected from the group consisting of *Amaranthus palmeri, Amaranthus rudis, Amaranthus albus, Amaranthus chlorostachys, Amaranthus graecizans, Amaranthus hybridus, Amaranthus lividus, Amaranthus spinosus, Amaranthus thunbergii, Amaranthus viridis, Lolium multiflorum, Lolium rigidium, Ambrosia artemisiifolia, Ambrosia trifida, Euphorbia heterophylla, Kochia scoparia, Abutilon theophrasti, Sorghum halepense, Chenopodium album, Commelina diffusa, Convulvulus arvensis, Conyza candensis, Digitaria sanguinalis,* and *Xanthium strumarium*. In some embodiments, the weed is growing in a field of herbicide-resistant crop plants. The bioactive trigger polynucleotide may be single-stranded DNA, single-stranded RNA, double-stranded RNA, double-stranded DNA, or a double-stranded DNA/RNA hybrid. In some embodiments, the bioactive trigger polynucleotide is double-stranded RNA and the double-stranded RNA comprises SEQ ID NOs: 3 and 4. In some embodiments, the bioactive trigger polynucleotide is double-stranded RNA and the double-stranded RNA comprises SEQ ID NOs: 5 and 6. In several embodiments, the bioactive trigger polynucleotide is provide with a transfer agent. In some embodiments, the transfer agent is an organosilicone surfactant. For example, the organosilicone surfactant may be BREAK-THRU® S 321, BREAK-THRU® S 200, BREAK-THRU® OE 441, BREAK-THRU® S 278, BREAK-THRU® S 243, SILWET L-77®, SILWET® HS 429, SILWET® HS 312, BREAK-THRU® S 233, or any combination thereof. In some embodiments, the transfer agent is a cationic liposomal reagent, for example, N-[1-(2,3-Dioleoyloxy)propyl]-N,N,N-trimethylammonium methyl-sulfate (DOTAP). In some embodiments, the transfer agent is a plant hormone, for example, Brassinosteroid. In some embodiments, the method further comprises treating the weed with an auxin-like herbicide, such as dicamba or 2,4-D.

Several embodiments relate to a method of controlling one or more plants of the following species: *Amaranthus, Ambrosia, Lolium, Digitaria, Euphorbia, Kochia, Sorghum, Conyza, Chloris, Echinochola, Eleusine, Poa, Plantago, Avena, Chenopodium, Setaria, Abutilon, Ipomoea, Sesbania, Cassia, Sida, Brachiaria* and *Solanum* by applying a bioactive trigger molecule as described herein.

Several embodiments relate to a method of controlling one or more of *Alopecurus myosuroides, Avena sterilis, Avena sterilis ludoviciana, Brachiaria plantaginea, Bromus diandrus, Bromus rigidus, Cynosurus echinatus, Digitaria ciliaris, Digitaria ischaemum, Digitaria sanguinalis, Echinochloa oryzicola, Echinochloa phyllopogon, Eriochloa punctata, Hordeum glaucum, Hordeum leporinum, Ischaemum rugosum, Leptochloa chinensis, Lolium persicum, Phalaris minor, Phalaris paradoxa, Rottboellia exalta, Setaria faberi, Setaria viridis* var. *robusta-alba schreiber, Setaria viridis* var. *robusta-purpurea, Snowdenia polystachea, Sorghum sudanese, Alisma plantago-aquatica, Amaranthus lividus, Amaranthus quitensis, Ammania auriculata, Ammania coccinea, Anthemis cotula, Apera spica-venti, Bacopa rotundifolia, Bidens pilosa, Bidens subalternans, Brassica tournefortii, Bromus tectorum, Camelina microcarpa, Chrysanthemum coronarium, Cuscuta campestris, Cyperus difformis, Damasonium minus, Descurainia sophia, Diplotaxis tenuifolia, Echium plantagineum, Elatine triandra* var. *pedicellate, Euphorbia heterophylla, Fallopia convolvulus, Fimbristylis miliacea, Galeopsis tetrahit, Galium spurium, Helianthus annuus, Iva xanthifolia, Ixophorus unisetus, Ipomoea indica, Ipomoea purpurea, Ipomoea sepiaria, Ipomoea aquatic, Ipomoea triloba, Lactuca serriola, Limnocharis flava, Limnophila erecta, Limnophila sessiliflora, Lindernia dubia, Lindernia dubia* var. major, *Lindernia micrantha, Lindernia procumbens, Mesembryanthemum crystallinum, Monochoria korsakowii, Monochoria vaginalis, Neslia paniculata, Papaver rhoeas, Parthenium hysterophorus, Pentzia suffruticosa, Phalaris minor, Raphanus raphanistrum, Raphanus sativus, Rapistrum rugosum, Rotala indica* var. *uliginosa, Sagittaria guyanensis, Sagittaria montevidensis, Sagittaria pygmaea, Salsola iberica, Scirpus juncoides* var. *ohwianus, Scirpus mucronatus, Setaria lutescens, Sida spinosa, Sinapis arvensis, Sisymbrium orientale, Sisymbrium thellungii, Solanum ptycanthum, Sonchus aspen, Sonchus oleraceus, Sorghum bicolor, Stellaria media, Thlaspi arvense, Xanthium strumarium, Arctotheca calendula, Conyza sumatrensis, Crassocephalum crepidiodes, Cuphea carthagenenis, Epilobium adenocaulon, Erigeron philadelphicus, Landoltia punctata, Lepidium virginicum, Monochoria korsakowii, Solanum americanum, Solanum nigrum, Vulpia bromoides, Youngia japonica, Hydrilla verticillata, Carduus nutans, Carduus pycnocephalus,*

*Centaurea solstitialis, Cirsium arvense, Commelina diffusa, Convolvulus arvensis, Daucus carota, Digitaria ischaemum, Echinochloa crus-pavonis, Fimbristylis miliacea, Galeopsis tetrahit, Galium spurium, Limnophila erecta, Matricaria perforate, Papaver rhoeas, Ranunculus acris, Soliva sessilis, Sphenoclea zeylanica, Stellaria media, Nassella trichotoma, Stipa neesiana, Agrostis stolonifera, Polygonum aviculare, Alopecurus japonicus, Beckmannia syzigachne, Bromus tectorum, Chloris inflate, Echinochloa erecta, Portulaca oleracea,* and *Senecio vulgaris* by applying a bioactive trigger polynucleotide as described herein.

BRIEF DESCRIPTION OF THE FIGURES

The following drawings form part of the specification and are included to further demonstrate certain aspects of the disclosed embodiments:

FIG. 1 shows glyphosate-tolerant Palmer plants treated with trigger polynucleotides for SEQ ID NOs: 7 and 8 and glyphosate (panel A), treated with trigger polynucleotides for SEQ ID NOs: 3 and 4 and glyphosate (panel B), or treated with trigger polynucleotides for SEQ ID NOs: 5 and 6 and glyphosate (panel C).

FIG. 2 shows a graph of % EPSPS mRNA reduction vs. control in Palmer protoplasts in response to 6 ug of SEQ ID NOs: 3 and 4 or SEQ ID NOs: 5 and 6 trigger.

FIG. 3 shows glyphosate-tolerant Waterhemp plants treated with SEQ ID NOs: 7 and 8 trigger polynucleotides and glyphosate (panel A), treated with trigger polynucleotides for SEQ ID NOs: 3 and 4 and glyphosate (panel B), or treated with trigger polynucleotides for SEQ ID NOs: 5 and 6 and glyphosate (panel C).

FIG. 4 shows the fresh weight (in grams) of plants treated with trigger polynucleotides for SEQ ID NOs: 3, 5, 7 and SEQ ID NOs: 36-64 and glyphosate.

DETAILED DESCRIPTION

Provided are methods and compositions containing a trigger polynucleotide that provide for regulation, repression or delay of 5-enolpyruvylshikimate-3-phosphate synthase (EPSPS) gene expression and enhanced control of weeds. In some embodiments, the methods and compositions disclosed herein provide for increased sensitivity to an EPSPS-inhibitor herbicide. In some embodiments, the methods and compositions disclosed herein provide for regulation, repression or delay of EPSPS gene expression in glyphosate-resistant weed biotypes. Aspects of the methods and compositions disclosed herein can be applied to manage various weeds in agronomic and other cultivated environments.

Definitions

The following terms are used throughout the present disclosure and the following definitions are provided to help guide those of ordinary skill in the art. Unless otherwise noted, terms are to be understood according to conventional usage by those of ordinary skill in the relevant art. Where a term is provided in the singular, the plural of that term is also contemplated unless otherwise noted.

As used herein, "a" or "an" may mean one or more than one.

As used herein, the term "about" indicates that a value includes the inherent variation or error for the device or method being employed to determine the value, or the variation that exists among the studied organism.

As used herein, the terms "DNA", "DNA molecule", and "DNA polynucleotide molecule" refer to a polymer of deoxyribonucleotide bases of genomic or synthetic origin. DNA may be wholly or partially single-stranded (ssDNA) or wholly or partially double-stranded (dsDNA). In some embodiments, a DNA molecule may comprise single-stranded and double-stranded regions.

As used herein, the terms "RNA", "RNA molecule", and "RNA polynucleotide molecule" refer to a polymer of ribonucleotide bases of cellular or synthetic origin. RNA may be wholly or partially single-stranded (ssRNA) or wholly or partially double-stranded (dsRNA). In some embodiments, a RNA molecule may comprise single-stranded and double-stranded regions.

As used herein, the terms "sequence", "nucleotide sequence" or "polynucleotide sequence" refer to the nucleotide sequence of a DNA molecule, an RNA molecule or a portion thereof. Unless otherwise stated, nucleotide sequences in the text of this specification are given, when read from left to right, in the 5' to 3' direction. It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. Further, disclosure of a nucleic acid sequence discloses the sequence of its reverse complement, as one necessarily defines the other, as is known by one of ordinary skill in the art.

The term "polynucleotide" refers to any polymer of mononucleotides that are linked by internucleotide bonds. Polynucleotides may be composed of naturally-occurring ribonucleotides, naturally-occurring deoxyribonucleotides, analogs of naturally-occurring nucleotides (e.g., enantiomeric forms of naturally-occurring nucleotides), or any combination thereof. Where a polynucleotide is single-stranded, its length can be described in terms of the number of nucleotides. Where a polynucleotide is double-stranded, its length can be described in terms of the number of base pairs.

As used herein, the term "non-transcribable polynucleotide" refers to a polynucleotide that does not comprise a complete polymerase II transcription unit.

As used herein, the term "trigger" or "trigger polynucleotide" refers to a bioactive polynucleotide molecule that is substantially homologous or complementary to a polynucleotide sequence of a target gene or an RNA expressed from the target gene or a fragment thereof and functions to suppress the expression of the target gene or produce a knock-down phenotype. Trigger polynucleotides are generally described in relation to their "target sequence." Trigger polynucleotides may be single-stranded DNA (ssDNA), single-stranded RNA (ssRNA), double-stranded RNA (dsRNA), double-stranded DNA (dsDNA), or double-stranded DNA/RNA hybrids. Trigger polynucleotides may comprise naturally-occurring nucleotides, modified nucleotides, nucleotide analogues or any combination thereof. In some embodiments, a trigger polynucleotide may be incorporated within a larger polynucleotide, for example in a pri-miRNA molecule. In some embodiments, a trigger polynucleotide may be processed into a small interfering RNA (siRNA).

As used herein, the term "target sequence" refers to a nucleotide sequence that occurs in a gene or gene product against which a trigger polynucleotide is directed. In this context, the term "gene" means a locatable region of genomic sequence, corresponding to a unit of inheritance, which includes regulatory regions, such as promoters, enhancers, 5' untranslated regions, intron regions, 3' untranslated regions, transcribed regions, and other functional sequence regions that may exist as native genes or transgenes in a plant genome. Depending upon the circumstances, the term target sequence can refer to the full-length nucleotide sequence of the gene or gene product targeted for suppression or the nucleotide sequence of a portion of the gene or gene product targeted for suppression. Disclosure of a target sequence necessarily discloses the sequence of its corresponding trigger polynucleotide, as one necessarily defines the other, as is known by one of ordinary skill in the art.

The term "gene expression" refers to the process of converting genetic information encoded in genomic DNA into RNA (e.g., mRNA, rRNA, tRNA, or snRNA) through transcription of the gene via the enzymatic action of an RNA polymerase, and into protein, through translation of mRNA. Gene expression can be regulated at many stages in the process.

As used herein, the phrases "inhibition of gene expression" or "gene suppression" or "silencing a target gene" and similar terms and phrases refer to the absence or observable reduction in the level of protein and/or mRNA product from the target gene. The consequences of inhibition, suppression, or silencing can be confirmed by examination of the outward properties of a cell or organism or by biochemical techniques.

As used herein, the term "sequence identity", "sequence similarity" or "homology" is used to describe the degree of similarity between two or more nucleotide sequences. The percentage of "sequence identity" between two sequences is determined by comparing two optimally aligned sequences over a comparison window, such that the portion of the sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. An alignment of two or more sequences may be performed using any suitable computer program. For example, a widely used and accepted computer program for performing sequence alignments is CLUSTALW v1.6 (Thompson, et al. Nucl. Acids Res., 22: 4673-4680, 1994).

As used herein "solution" refers to homogeneous mixtures and non-homogeneous mixtures such as suspensions, colloids, micelles, and emulsions.

As used herein, the term "weed" refers to any plant that is not valued where it is growing. Weeds usually exhibit vigorous growth and tend to overgrow or choke out more desirable plants. Weeds include volunteer plants, which grow on their own, rather than being planted by a farmer or gardener. For example, corn plants growing in a soybean field.

Weedy plants include, but are not limited to, important invasive and noxious weeds and herbicide resistant biotypes in crop production, such as: *Amaranthus* species, e.g., *A. albus, A. blitoides, A. hybridus, A. palmeri, A. powellii, A. retroflexus, A. spinosus, A. tuberculatus,* and *A. viridis; Ambrosia* species, e.g., *A. trifida,* and *A. artemisifolia; Lolium* species, e.g., *L. multiflorum, L. rigidium,* and *L. perenne; Digitaria* species, e.g., *D. insularis; Euphorbia* species, e.g., *E. heterophylla; Kochia* species, e.g., *K. scoparia; Sorghum* species, e.g., *S. halepense; Conyza* species, e.g., *C. bonariensis, C. canadensis,* and *C. sumatrensis; Chloris* species, e.g., *C. truncate; Echinochola* species, e.g., *E. colona* and *E. crus-galli; Eleusine* species, e.g., *E. indica; Poa* species, e.g., *P. annua; Plantago* species, e.g., *P. lanceolata; Avena* species, e.g., *A. fatua; Chenopodium* species, e.g., *C. album; Setaria* species, e.g., *S. viridis; Abutilon theophrasti; Ipomoea* species; *Sesbania* species; *Cassia* species; *Sida* species; *Brachiaria* species and *Solanum* species.

Additional weedy plant species found in cultivated areas include *Alopecurus myosuroides, Avena sterilis, Avena sterilis ludoviciana, Brachiaria plantaginea, Bromus diandrus, Bromus rigidus, Cynosurus echinatus, Digitaria ciliaris, Digitaria ischaemum, Digitaria sanguinalis, Echinochloa oryzicola, Echinochloa phyllopogon, Eriochloa punctata, Hordeum glaucum, Hordeum leporinum, Ischaemum rugosum, Leptochloa chinensis, Lolium persicum, Phalaris minor, Phalaris paradoxa, Rottboellia exalta, Setaria faberi, Setaria viridis* var, *robusta-alba schreiber, Setaria viridis* var, *robusta-purpurea, Snowdenia polystachea, Sorghum sudanese, Alisma plantago-aquatica, Amaranthus lividus, Amaranthus quitensis, Ammania auriculata, Ammania coccinea, Anthemis cotula, Apera spica-venti, Bacopa rotundifolia, Bidens pilosa, Bidens subalternans, Brassica tournefortii, Bromus tectorum, Camelina microcarpa, Chrysanthemum coronarium, Cuscuta campestris, Cyperus difformis, Damasonium minus, Descurainia sophia, Diplotaxis tenuifolia, Echium plantagineum, Elatine triandra* var, *pedicellate, Euphorbia heterophylla, Fallopia convolvulus, Fimbristylis miliacea, Galeopsis tetrahit, Galium spurium, Helianthus annuus, Iva xanthifolia, Ixophorus unisetus, Ipomoea indica, Ipomoea purpurea, Ipomoea sepiaria, Ipomoea aquatic, Ipomoea triloba, Lactuca serriola, Limnocharis flava, Limnophila erecta, Limnophila sessiliflora, Lindernia dubia, Lindernia dubia* var, major, *Lindernia micrantha, Lindernia procumbens, Mesembryanthemum crystallinum, Monochoria korsakowii, Monochoria vaginalis, Neslia paniculata, Papaver rhoeas, Parthenium hysterophorus, Pentzia suffruticosa, Phalaris minor, Raphanus raphanistrum, Raphanus sativus, Rapistrum rugosum, Rotala indica* var, *uliginosa, Sagittaria guyanensis, Sagittaria montevidensis, Sagittaria pygmaea, Salsola iberica, Scirpus juncoides* var, *ohwianus, Scirpus mucronatus, Setaria lutescens, Sida spinosa, Sinapis arvensis, Sisymbrium orientale, Sisymbrium thellungii, Solanum ptycanthum, Sonchus aspen, Sonchus oleraceus, Sorghum bicolor, Stellaria media, Thlaspi arvense, Xanthium strumarium, Arctotheca calendula, Conyza sumatrensis, Crassocephalum crepidiodes, Cuphea carthagenensis, Epilobium adenocaulon, Erigeron philadelphicus, Landoltia punctata, Lepidium virginicum, Monochoria korsakowii, Solanum americanum, Solanum nigrum, Vulpia bromoides, Youngia japonica, Hydrilla verticillata, Carduus nutans, Carduus pycnocephalus, Centaurea solstitialis, Cirsium arvense, Commelina diffusa, Convolvulus arvensis, Daucus carota, Digitaria ischaemum, Echinochloa crus-pavonis, Fimbristylis miliacea, Galeopsis tetrahit, Galium spurium, Limnophila erecta, Matricaria perforate, Papaver rhoeas, Ranunculus acris, Soliva sessilis, Sphenoclea zeylanica, Stellaria media, Nassella trichotoma, Stipa neesiana, Agrostis stolonifera, Polygonum aviculare, Alopecurus japonicus, Beckmannia syzigachne, Bromus tectorum, Chloris inflate, Echinochloa erecta, Por-*

*tulaca oleracea*, and *Senecio vulgaris*. The embodiments disclosed herein may be utilized to control any of these species.

As used herein, the term "herbicide" refers to molecules that affect plant growth, development and/or reproductive ability. Herbicides may be polynucleotide or non-polynucleotide. Glyphosate is an example of a non-polynucleotide herbicide that inhibits EPSPS.

"Glyphosate" (N-phosphonomethylglycine) herbicide inhibits the shikimic acid pathway, which leads to the biosynthesis of aromatic compounds including amino acids, plant hormones and vitamins Specifically, glyphosate curbs the conversion of phosphoenolpyruvic acid (PEP) and 3-phosphoshikimic acid to 5-enolpyruvyl-3-phosphoshikimic acid by inhibiting the enzyme 5-enolpyruvylshikimate-3-phosphate synthase (referred to herein as EPSP synthase or EPSPS). The term "glyphosate" should be considered to include any herbicidally effective form of N-phosphonomethylglycine (including any salt thereof) and other forms which result in the production of the glyphosate anion in planta. Glyphosate is commercially available in numerous formulations. Examples of these formulations of glyphosate include, without limitation, those sold by Monsanto Company (St. Louis, Mo.) as ROUNDUP®, ROUNDUP® ULTRA, ROUNDUP® ULTRAMAX, ROUNDUP® CT, ROUNDUP® EXTRA, ROUNDUP® BIACTIVE, ROUNDUP® BIOFORCE, RODEO®, POLARIS®, SPARK® and ACCORD® herbicides, all of which contain glyphosate as its isopropylammonium salt; ROUNDUP® WEATHERMAX, which contains glyphosate as its potassium salt; ROUNDUP® DRY and RIVAL® herbicides, which contain glyphosate as its ammonium salt; ROUNDUP® GEOFORCE, which contains glyphosate as its sodium salt. Other examples include TOUCHDOWN® herbicide (Syngenta, Greensboro, N.C.), which contains glyphosate as its trimethylsulfonium salt. Various other salts of glyphosate are available for example, dimethylamine salt, isopropylamine salt, trimesium salt, potassium salt, monoammonium salt, and diammonium salt. Commerical formulations and application rates thereof are often defined in terms of acid equivalent pounds per acre (a.e. lb/ac).

Bioactive Polynucleotide Triggers

Several embodiments described herein relate to compositions comprising a bioactive trigger polynucleotide targeting an EPSPS gene. Such compositions and methods of their use are useful for modulating the expression of endogenous EPSPS genes or transgenic EPSPS genes (for example, CP4 EPSPS, U.S. Pat. No. RE39,247 and 2mEPSPS, U.S. Pat. No. 6,040,497) in a plant cell. In various embodiments, a targeted EPSPS gene includes coding (protein-coding or translatable) sequence, non-coding (non-translatable) sequence, or both coding and non-coding sequence. A plant treated with a bioactive EPSPS trigger polynucleotide is more sensitive to an EPSPS-inhibitor herbicide relative to a plant that has not been treated with a bioactive EPSPS trigger polynucleotide. It is contemplated that in some embodiments the composition may contain multiple bioactive trigger polynucleotides. Where multiple bioactive trigger polynucleotides are used, the bioactive trigger polynucleotides can target multiple consecutive segments of a target gene, multiple non-consecutive segments of a target gene, multiple alleles of a target gene, or multiple different target genes from one or more species. For example, in some embodiments the composition may comprise two or more bioactive EPSPS trigger polynucleotides that are capable of binding to different EPSPS target sequences. In some embodiments, the different EPSPS target sequences may be from different plant species. In some embodiments, the different EPSPS target sequences may be from different regions of an EPSPS gene. In some embodiments, the EPSPS target sequences may be selected from the group consisting of SEQ ID NOs: 9-66.

Several embodiments described herein relate to compositions comprising one or more bioactive trigger polynucleotides targeting an EPSPS gene and one or more bioactive trigger polynucleotides that modulate the expression of a gene other than EPSPS. In some embodiments, compositions can include one or more bioactive trigger polynucleotides targeting essential genes. Essential genes are genes in a plant that provide key enzymes or other proteins that are essential to the growth, survival, development or reproduction of the plant (Meinke, et al., Trends Plant Sci. 2008:13 (9):483-91). Examples of essential genes include, but are not limited to, genes encoding biosynthetic enzymes, metabolizing enzymes, receptors, signal transduction proteins, structural proteins, transcription factors, transport proteins and regulatory RNAs, such as, microRNAs. In some embodiments, the suppression of an essential gene enhances the effect of a herbicide that affects the function of a gene product different than the suppressed essential gene.

Bioactive trigger polynucleotides used in the various embodiments may comprise single-stranded RNA, double-stranded RNA, single-stranded DNA, double-stranded DNA, RNA/DNA hybrids, chemically modified polynucleotides or any mixture thereof. In some embodiments, the bioactive trigger polynucleotide may comprise a combination of ribonucleotides and deoxyribonucleotides, for example, synthetic polynucleotides consisting mainly of ribonucleotides but with one or more terminal deoxyribonucleotides or synthetic polynucleotides consisting mainly of deoxyribonucleotides but with one or more terminal dideoxyribonucleotides. In some embodiments, the bioactive trigger polynucleotide includes non-canonical nucleotides such as inosine, thiouridine, or pseudouridine. In some embodiments, the bioactive trigger polynucleotide includes chemically modified nucleotides. For example, the naturally occurring phosphodiester backbone of a bioactive trigger polynucleotide can be partially or completely modified with phosphorothioate, phosphorodithioate, or methylphosphonate internucleotide linkage modifications, modified nucleoside bases or modified sugars can be used in the synthesis of bioactive trigger polynucleotides, and trigger polynucleotides can be labeled with a fluorescent moiety (for example, fluorescein or rhodamine) or other label (for example, biotin). Examples of chemically modified oligonucleotides or polynucleotides are well known in the art; see, for example, US Patent Publication 20110171287, US Patent Publication 20110171176, and US Patent Publication 20110152353, US Patent Publication, 20110152346, US Patent Publication 20110160082, herein incorporated in its entirety by reference hereto.

Several embodiments relate to bioactive trigger polynucleotides that modulate an endogenous EPSPS gene in a plant. In some embodiments, the bioactive EPSPS trigger polynucleotides comprise a nucleotide sequence that is essentially identical or essentially complementary to at least 10 contiguous nucleotides of an endogenous EPSPS gene of a plant, or an RNA transcribed therefrom. In some embodiments, the bioactive EPSPS trigger polynucleotides comprise a nucleotide sequence that is essentially identical or essentially complementary to 15, 20, 25, 30, 35, 40, 45, 50, 55, 60, 65, 70 or more contiguous nucleotides of an endogenous EPSPS gene of a plant, or an RNA transcribed therefrom. In some embodiments, the endogenous EPSPS gene is an *Abutilon theophrasti, Amaranthus graecizans, Amaranthus hybrid, Amaranthus lividus, Amaranthus palmeri, Amaranthus rudis, Amaranthus thunbergii, Amaranthus viridis, Ambrosia trifida, Chenopodium album, Convolvulus arvensis, Conyza Canadensis, Digitaria sanguinalis, Echinochloa colona, Echinochloa crus-galli, Euphorbia heterophylla, Ipomoea hederacea, Lolium multiflorum, Senna obtusifolia, Sorghum halepense*, or *Xanthium strumarium* gene. In some embodiments, the sequence of the endogenous EPSPS gene is selected from SEQ ID NOs: 1 and 2.

By "essentially identical" or "essentially complementary" is meant that the bioactive trigger polynucleotide (or at least one strand of a double-stranded polynucleotide or portion thereof, or a portion of a single strand polynucleotide) hybridizes under physiological conditions to the endogenous gene, an RNA transcribed therefrom, or a fragment thereof, to effect regulation or suppression of the endogenous gene. For example, in some embodiments, a bioactive trigger polynucleotide has 100 percent sequence identity or at least about 83, 84, 85, 86, 87, 88, 89, 90, 91, 92, 93, 94, 95, 96, 97, 98, or 99 percent sequence identity when compared to a sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more contiguous nucleotides in the target gene or RNA transcribed from the target gene. In some embodiments, a bioactive trigger polynucleotide has 100 percent sequence complementarity or at least about 83, 84, 85, 86, 87, 88, 89, 90, 91, 92, 93, 94, 95, 96, 97, 98, or 99 percent sequence complementarity when compared to a sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more contiguous nucleotides in the target gene or RNA transcribed from the target gene. In some embodiments, a bioactive trigger polynucleotide has 100 percent sequence identity with or complementarity to one allele or one family member of a given target gene (coding or non-coding sequence of a gene). In some embodiments, a bioactive trigger polynucleotide has at least about 83, 84, 85, 86, 87, 88, 89, 90, 91, 92, 93, 94, 95, 96, 97, 98, or 99 percent sequence identity with or complementarity to multiple alleles or family members of a given target gene. In some embodiments, a bioactive trigger polynucleotide has 100 percent sequence identity with or complementarity to multiple alleles or family members of a given target gene.

Embodiments include bioactive trigger polynucleotides having a length of 40-60 nucleotides (40-mers, 41-mers, 42-mers, 43-mers, 44-mers, 45-mers, 46-mers, 47-mers, 48-mers, 49-mers, 50-mers, 51-mers, 52-mers, 53-mers, 54-mers, 55-mers, 56-mers, 57-mers, 58-mers, 59-mers, or 60-mers). Several embodiments relate to a bioactive EPSPS trigger polynucleotide that comprises a nucleotide sequence that is substantially homologous or substantially complementary to one or more of SEQ ID NOs: 9-66 and suppresses, represses or otherwise delays the expression of a targeted EPSPS gene in one or more plant species. In some embodiments, the bioactive EPSPS trigger polynucleotide comprises a nucleotide sequence that is identical or complementary to one or more of SEQ ID NOs: 9-66. In some embodiments, the bioactive EPSPS trigger polynucleotide comprises a sequence selected from SEQ ID NOs: 3-6.

Bioactive trigger polynucleotides can be single- or double-stranded RNA or single- or double-stranded DNA or double-stranded DNA/RNA hybrids or modified analogues thereof. In some embodiments, the trigger polynucleotides are selected from the group consisting of (a) a single-stranded RNA molecule (ssRNA), (b) a ssRNA molecule that self-hybridizes to form a double-stranded RNA molecule, (c) a double-stranded RNA molecule (dsRNA), (d) a single-stranded DNA molecule (ssDNA), (e) a ssDNA molecule that self-hybridizes to form a double-stranded DNA molecule, and (f) a single-stranded DNA molecule including a modified Pol III gene that is transcribed to an RNA molecule, (g) a double-stranded DNA molecule (dsDNA), (h) a double-stranded DNA molecule including a modified Pol III gene that is transcribed to an RNA molecule, (i) a double-stranded, hybridized RNA/DNA molecule, or combinations thereof. In some embodiments these polynucleotides include chemically modified nucleotides or non-canonical nucleotides.

In some embodiments, double-stranded trigger polynucleotides may be blunt-ended or may comprise a 3' or 5' overhang of one, two, three, four, five, or more nucleotides on one or both sides of the double-stranded region. In some embodiments, the overhang has identity or complementarity to the target gene. In some embodiments, the overhang does not have identity or complementarity to the target gene. In some embodiments, the overhang may comprise one, two, three, four, or more nucleotides such as 2'-deoxy (21H) nucleotides. In some embodiments, the overhang may comprise deoxythymidine (dT) nucleotides.

Double-stranded bioactive trigger polynucleotides may be formed by intramolecular hybridization or intermolecular hybridization. In some embodiments, the bioactive trigger polynucleotide may comprise single-stranded DNA or single-stranded RNA that self-hybridizes to form a hairpin structure having an at least partially double-stranded structure including at least one segment that will hybridize to an RNA transcribed from the gene targeted for suppression. In some embodiments, the bioactive trigger polynucleotide may be contained in a longer polynucleotide sequence, for example a in a pri-miRNA. Other configurations of the bioactive trigger polynucleotides are known in the field and are contemplated herein.

Methods of making bioactive trigger polynucleotides are well known in the art. For example, bioactive trigger polynucleotides can be can be expressed in host cells from a vector, chemically synthesized using known methods, or they can be transcribed in vitro by conventional enzymatic synthetic methods using, for example, the bacteriophage T7, T3 or SP6 RNA polymerases. Commercial preparation of oligonucleotides often provides two deoxyribonucleotides on the 3' end of the sense strand. Polynucleotide molecules can be synthesized from commercially available kits, for example, kits from Applied Biosystems/Ambion (Austin, Tex.) have DNA ligated on the 5' end in a microbial expression cassette that includes a bacterial T7 polymerase promoter that makes RNA strands that can be assembled into a dsRNA and kits provided by various manufacturers that include T7 RiboMax Express (Promega, Madison, Wis.), AmpliScribe T7-Flash (Epicentre, Madison, Wis.), and TranscriptAid T7 High Yield (Fermentas, Glen Burnie, Md.). dsRNA molecules can be produced from microbial expression cassettes in bacterial cells (Ongvarrasopone et al. ScienceAsia 33:35-39; Yin, Appl. Microbiol. Biotechnol 84:323-333, 2009; Liu et al., BMC Biotechnology 10:85, 2010) that have regulated or deficient RNase III enzyme activity or the use of various viral vectors to produce sufficient quantities of dsRNA. EPSPS gene fragments are inserted into the microbial expression cassettes in a position in which the fragments are expressed to produce ssRNA or dsRNA useful in the methods described herein to regulate expression on a target EPSPS gene. Several embodiments relate to expression constructs encoding bioactive trigger polynucleotides as described herein.

Following synthesis, the trigger polynucleotides may optionally be purified. For example, polynucleotides can be purified from a mixture by extraction with a solvent or resin, precipitation, electrophoresis, chromatography, or a combination thereof. Alternatively, trigger polynucleotides may be used with no, or a minimum of, purification to avoid losses due to sample processing. The trigger polynucleotides may be dried for storage or dissolved in an aqueous solution. The solution may contain buffers or salts to promote annealing, and/or stabilization of the duplex strands.

Compositions and Methods for Weed Control

Bioactive trigger polynucleotides may be provided to a plant at any dose effective to modulate the expression of the target gene or produce a knock-down phenotype. While there is no upper limit on the concentrations and dosages of bioactive trigger polynucleotides used in the compositions and methods disclosed herein, several embodiments relate to a minimum effective concentration or dosage of bioactive trigger polynucleotide. The concentration of bioactive trigger polynucleotide provided to a plant can be adjusted in consideration of the volume of spray or treatment applied to plant leaves or other plant part surfaces, such as flower petals, stems, tubers, fruit, anthers, pollen, or seed. In one embodiment, a treatment for herbaceous plants comprises providing bioactive trigger polynucleotides at about 1 nanomole (nmol) per plant. In some embodiments, a treatment for herbaceous plants comprises providing from about 0.05 to 1 nmol of bioactive trigger polynucleotide per plant. Several embodiments for herbaceous plants include ranges of about 0.05 to about 100 nmol, or about 0.1 to about 20 nmol, or about 1 nmol to about 10 nmol of bioactive trigger polynucleotides per plant. In some embodiments, a treatment for herbaceous plants comprises providing 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20 nmol of bioactive trigger polynucleotides per plant.

To illustrate embodiments, the factor 1×, when applied to oligonucleotide molecules is arbitrarily used to denote a treatment of 0.8 nmol of bioactive trigger polynucleotide molecule per plant; 10×, 8 nmol of bioactive trigger polynucleotide molecule per plant; and 100×, 80 nmol of bioactive trigger polynucleotide molecule per plant. The amount of bioactive trigger polynucleotide provided can vary based upon the size of the treated plant. For example, for very large plants, trees, or vines a correspondingly larger amount of bioactive trigger polynucleotide may be used; while for smaller plants, a correspondingly smaller amount of bioactive trigger polynucleotide may be used. In some embodiments where long dsRNA molecules, which are processed into multiple oligonucleotides, are used, the effective concentration or dosage of bioactive trigger polynucleotide may be lower.

In several embodiments, bioactive trigger polynucleotides are incorporated into a plant cell following topical application of the bioactive trigger polynucleotides to a surface of the plant, for example, by spraying the plant with the bioactive trigger polynucleotides. In some embodiments, bioactive trigger polynucleotides are applied without wounding plant tissue and cells, such as, by mechanical-type wounding or particle bombardment. In some embodiments, bioactive trigger polynucleotides are incorporated into a plant cell without infection with viral vector.

Several embodiments relate to compositions comprising an effective amount of a bioactive trigger polynucleotide, alone or in combination with other components, for example, one or more non-polynucleotide herbicide molecules, and/or one or more transfer agents. In some embodiments, one or more bioactive trigger polynucleotides are provided in the same composition as a transfer agent. In other embodiments, the bioactive trigger polynucleotides and the transfer agent are separately applied. In some embodiments, one or more bioactive trigger polynucleotides and one or more non-polynucleotide herbicide molecules are provided in the same composition. In other embodiments, one or more bioactive trigger polynucleotides and one or more non-polynucleotide herbicide molecules are provided in separately applied compositions. In some embodiments, the transfer agent and non-polynucleotide herbicide are provided in the same composition. Several embodiments relate to a composition comprising one or more bioactive trigger polynucleotides, one or more transfer agents and one or more non-polynucleotide herbicides. In some embodiments, one or more of the bioactive trigger polynucleotide, the non-polynucleotide herbicide and the transfer agent is provided in a liquid composition.

Non-polynucleotide herbicides may be applied concomitantly with a bioactive trigger polynucleotide or the bioactive trigger polynucleotide and the non-polynucleotide herbicide may be applied at different times. In some embodiments, a composition comprising a bioactive trigger polynucleotide is provided to a plant prior to providing a composition comprising a non-polynucleotide herbicide. In some embodiments, a composition comprising a bioactive trigger polynucleotide is provided to a plant subsequent to providing a non-polynucleotide herbicide. In some embodiments, bioactive trigger polynucleotides may be applied concomitantly with a transfer agent. In other embodiments, the bioactive trigger polynucleotides and the transfer agent are applied at different times. In some embodiments, a composition comprising a bioactive trigger polynucleotide is provided to a plant prior to providing a composition comprising a transfer agent. In some embodiments, a composition comprising a bioactive trigger polynucleotide is provided to a plant subsequent to providing a transfer agent.

Several embodiments relate to compositions and methods that provide multi-species weed control. Numerous non-polynucleotide herbicides are known and can be added, either alone or in combination with one or more non-polynucleotide herbicides having similar or different modes of action (herein referred to as co-herbicides), to a composition comprising a bioactive EPSPS trigger polynucleotide or can be used in conjunction with a bioactive EPSPS trigger polynucleotide to control weeds. For example, members of the herbicide families include, but are not limited to: amide herbicides, aromatic acid herbicides, arsenical herbicides, benzothiazole herbicides, benzoylcyclohexanedione herbicides, benzofuranyl alkylsulfonate herbicides, carbamate herbicides, cyclohexene oxime herbicides, cyclopropylisoxazole herbicides, dicarboximide herbicides, dinitroaniline herbicides, dinitrophenol herbicides, diphenyl ether herbicides, dithiocarbamate herbicides, halogenated aliphatic herbicides, imidazolinone herbicides, inorganic herbicides, nitrile herbicides, organophosphorus herbicides, oxadiazolone herbicides, oxazole herbicides, phenoxy herbicides, phenylenediamine herbicides, pyrazole herbicides, pyridazine herbicides, pyridazinone herbicides, pyridine herbicides, pyrimidinediamine herbicides, pyrimidinyloxybenzylamine herbicides, quaternary ammonium herbicides, thiocarbamate herbicides, thiocarbonate herbicides, thiourea herbicides, triazine herbicides, triazinone herbicides, triazole herbicides, triazolone herbicides, triazolopyrimidine herbicides, uracil herbicides, and urea herbicides. Representative herbicides of the families include but are not limited to acetochlor, acifluorfen, acifluorfen-sodium, aclonifen, acrolein, alachlor, alloxydim, allyl alcohol, ametryn, amicarbazone, amidosulfuron, aminopyralid, amitrole, ammonium sulfamate, anilofos, asulam, atraton, atrazine, azimsulfuron, BCPC, beflubutamid, benazolin, benfluralin, benfuresate, bensulfuron, bensulfuron-methyl, bensulide, bentazone, benzfendizone, benzobicyclon, benzofenap, bifenox, bilanafos, bispyribac, bispyribac-sodium, borax, bromacil, bromobutide, bromoxynil, butachlor, butafenacil, butamifos, butralin, butroxydim, butylate, cacodylic acid, calcium chlorate, cafenstrole, carbetamide, carfentrazone, carfentrazone-ethyl, CDEA, CEPC, chlorflurenol, chlorflurenol-methyl, chloridazon, chlorimuron, chlorimuron-ethyl, chloroacetic acid, chlorotoluron, chlorpropham, chlorsulfuron, chlorthal, chlorthal-dimethyl, cinidon-ethyl, cinmethylin, cinosulfuron, cisanilide, clethodim, clodinafop, clodinafop-propargyl, clomazone, clomeprop, clopyralid, cloransulam, cloransulam-methyl, CMA, 4-CPB, CPMF, 4-CPP, CPPC, cresol, cumyluron, cyanamide, cyanazine, cycloate, cyclosulfamuron, cycloxydim, cyhalofop, cyhalofop-butyl, 2,4-D, 3,4-DA, daimuron, dalapon, dazomet, 2,4-DB, 3,4-DB, 2,4-DEB, desmedipham, dicamba, dichlobenil, ortho-dichlorobenzene, para-dichlorobenzene, dichlorprop, dichlorprop-P, diclofop, diclofop-methyl, diclosulam, difenzoquat, difenzoquat metilsulfate, diflufenican, diflufenzopyr, dimefuron, dimepiperate, dimethachlor, dimethametryn, dimethenamid, dimethenamid-P, dimethipin, dimethylarsinic acid, dinitramine, dinoterb, diphenamid, diquat, diquat dibromide, dithiopyr, diuron, DNOC, 3,4-DP, DSMA, EBEP, endothal, EPTC, esprocarb, ethalfluralin, ethametsulfuron, ethametsulfuron-methyl, ethofumesate, ethoxyfen, ethoxysulfuron, etobenzanid, fenoxaprop-P, fenoxaprop-P-ethyl, fentrazamide, ferrous sulfate, flamprop-M, flazasulfuron, florasulam, fluazifop, fluazifop-butyl, fluazifop-P, fluazifop-P-butyl, flucarbazone, flucarbazone-sodium, flucetosulfuron, fluchloralin, flufenacet, flufenpyr, flufenpyr-ethyl, flumetsulam, flumiclorac, flumiclorac-pentyl, flumioxazin, fluometuron, fluoroglycofen, fluoroglycofen-ethyl, flupropanate, flupyrsulfuron, flupyrsulfuron-methyl-sodium, flurenol, fluridone, fluorochloridone, fluoroxypyr, flurtamone, fluthiacet, fluthiacet-methyl, fomesafen, foramsulfuron, fosamine, glufosinate, glufosinate-ammonium, glyphosate, halosulfuron, halosulfuron-methyl, haloxyfop, haloxyfop-P, HC-252, hexazinone, imazamethabenz, imazamethabenz-methyl, imazamox, imazapic, imazapyr, imazaquin, imazethapyr, imazosulfuron, indanofan, iodomethane, iodosulfuron, iodosulfuron-methyl-sodium, ioxynil, isoproturon, isouron, isoxaben, isoxachlortole, isoxaflutole, karbutilate, lactofen, lenacil, linuron, MAA, MAMA, MCPA, MCPA-thioethyl, MCPB, mecoprop, mecoprop-P, mefenacet, mefluidide, mesosulfuron, mesosulfuron-methyl, mesotrione, metam, metamifop, metamitron, metazachlor, methabenzthiazuron, methylarsonic acid, methyldymron, methyl isothiocyanate, metobenzuron, metolachlor, S-metolachlor, metosulam, metoxuron, metribuzin, metsulfuron, metsulfuron-methyl, MK-66, molinate, monolinuron, MSMA, naproanilide, napropamide, naptalam, neburon, nicosulfuron, nonanoic acid, norflurazon, oleic acid (fatty acids), orbencarb, orthosulfamuron, oryzalin, oxadiargyl, oxadiazon, oxasulfuron, oxaziclomefone, oxyfluorfen, paraquat, paraquat dichloride, pebulate, pendimethalin, penoxsulam, pentachlorophenol, pentanochlor, pentoxazone, pethoxamid, petroleum oils, phenmedipham, phenmedipham-ethyl, picloram, picolinafen, pinoxaden, piperophos, potassium arsenite, potassium azide, pretilachlor, primisulfuron, primisulfuron-methyl, prodiamine, profluazol, profoxydim, prometon, prometryn, propachlor, propanil, propaquizafop, propazine, propham, propisochlor, propoxycarbazone, propoxycarbazone-sodium, propyzamide, prosulfocarb, prosulfuron, pyraclonil, pyraflufen, pyraflufen-ethyl, pyrazolynate, pyrazosulfuron, pyrazosulfuron-ethyl, pyrazoxyfen, pyribenzoxim, pyributicarb, pyridafol, pyridate, pyriftalid, pyriminobac, pyriminobac-methyl, pyrimisulfan, pyrithiobac, pyrithiobac-sodium, quinclorac, quinmerac, quinoclamine, quizalofop, quizalofop-P, rimsulfuron, sethoxydim, siduron, simazine, simetryn, SMA, sodium arsenite, sodium azide, sodium chlorate, sulcotrione, sulfentrazone, sulfometuron, sulfometuron-methyl, sulfosate, sulfosulfuron, sulfuric acid, tar oils, 2,3,6-TBA, TCA, TCA-sodium, tebuthiuron, tepraloxydim, terbacil, terbumeton, terbuthylazine, terbutryn, thenylchlor, thiazopyr, thifensulfuron, thifensulfuron-methyl, thiobencarb, tiocarbazil, topramezone, tralkoxydim, tri-allate, triasulfuron, triaziflam, tribenuron, tribenuron-methyl, tricamba, triclopyr, trietazine, trifloxysulfuron, trifloxysulfuron-sodium, trifluralin, triflusulfuron, triflusulfuron-methyl, trihydroxytriazine, tritosulfuron, [3-[2-chloro-4-fluoro-5-(-methyl-6-trifluoromethyl-2,4-dioxo-,2,3,4-tetrahydropyrimidin-3-yl)phenoxy]-2-pyridyloxy]acetic acid ethyl ester (CAS RN 353292-3-6), 4-[(4,5-dihydro-3-methoxy-4-methyl-5-oxo)-H-,2,4-triazol-1-ylcarbonyl-sulfamoyl]-5-methylthiophene-3-carboxylic acid (BAY636), BAY747 (CAS RN 33504-84-2), topramezone (CAS RN 2063-68-8), 4-hydroxy-3-[[2-[(2-methoxyethoxy)methyl]-6-(trifluoro-methyl)-3-pyridi-nyl]carbonyl]-bicyclo[3.2.] oct-3-en-2-one (CAS RN 35200-68-5), and 4-hydroxy-3-[[2-(3-methoxypropyl)-6-(difluoromethyl)-3-pyridinyl] carbon-yl]-bicyclo[3.2.]oct-3-en-2-one. Additionally, including herbicidal compounds of unspecified modes of action as described in CN101279950A, CN101279951A, DE10000600A1, DE10116399A1, DE102004054666A1, DE102005014638A1, DE102005014906A1, DE102007012168A1, DE102010042866A1, DE10204951A1, DE10234875A1, DE10234876A1, DE10256353A1, DE10256354A1, DE10256367A1, EP1157991A2, EP1238586A1, EP2147919A1, EP2160098A2, JP03968012B2, JP2001253874A, JP2002080454A, JP2002138075A, JP2002145707A, JP2002220389A, JP2003064059A, JP2003096059A, JP2004051628A, JP2004107228A, JP2005008583A, JP2005239675A, JP2005314407A, JP2006232824A, JP2006282552A, JP2007153847A, JP2007161701A, JP2007182404A, JP2008074840A, JP2008074841A, JP2008133207A, JP2008133218A, JP2008169121A, JP2009067739A, JP2009114128A, JP2009126792A, JP2009137851A, US20060111241A1, US20090036311A1, US20090054240A1, US20090215628A1, US20100099561A1, US20100152443A1, US20110105329A1, US20110201501A1, WO2001055066A2, WO2001056975A1, WO2001056979A1, WO2001090071A2, WO2001090080A1, WO2002002540A1, WO2002028182A1, WO2002040473A1, WO2002044173A2, WO2003000679A2, WO2003006422A1, WO2003013247A1, WO2003016308A1, WO2003020704A1, WO2003022051A1, WO2003022831A1, WO2003022843A1, WO2003029243A2, WO2003037085A1, WO2003037878A1, WO2003045878A2, WO2003050087A2, WO2003051823A1, WO2003051824A1, WO2003051846A2, WO2003076409A1, WO2003087067A1,
WO2003091217A1,
WO2003104206A2,
WO2004002981A2,
WO2004029060A1,
WO2004035563A1,
WO2004037787A1,
WO2004067527A1,
WO2005000824A1,
WO2005040152A1,
WO2005047281A1,
WO2005061464A1,
WO2005070889A1,
WO2005095335A1,
WO2006024820A1,
WO2006029829A1,
WO2006050803A1,
WO2006123088A2,
WO2006125688A1,
WO2007026834A1,
WO2007077201A1,
WO2007096576A1,
WO2007134984A1,
WO2008029084A1,
WO2008071918A1,
WO2008084073A1,
WO2008102908A1,
WO2008152073A2,
WO2009005297A2,
WO2009063180A1,
WO2009068171A2,
WO2009090401A2,
WO2009115788A1,
WO2009152995A1,
WO2010012649A1,
WO2010026989A1,
WO2010049270A1,
WO2010049405A1,
WO2010063422A1,
WO2010078906A2,
WO2010104217A1,
WO2010112826A3,
WO2010119906A1,
WO2011003776A2,
WO2011065451A1,
WO2003090539A1,
WO2003093269A2,
WO2004002947A1,
WO2004011429A1,
WO2004035545A2,
WO2004035564A1,
WO2004067518A1,
WO2004077950A1,
WO2005007627A1,
WO2005047233A1,
WO2005061443A2,
WO2005068434A1,
WO2005089551A1,
WO2006006569A1,
WO2006029828A1,
WO2006037945A1,
WO2006090792A1,
WO2006125687A1,
WO2007003294A1,
WO2007071900A1,
WO2007077247A1,
WO2007119434A1,
WO2008009908A1,
WO2008059948A1,
WO2008074991A1,
WO2008100426A2,
WO2008152072A2,
WO2009000757A1,
WO2009035150A2,
WO2009068170A2,
WO2009086041A1,
WO2009090402A2,
WO2009116558A1,
WO2009158258A1,
WO2010012649A1,
WO2010034153A1,
WO2010049369A1,
WO2010049414A1,
WO2010069802A1,
WO2010078912A1,
WO2010108611A1,
WO2010116122A3,
WO2010130970A1,
WO2011035874A1,
all of which are incorporated herein by reference. In some embodiments, two or more non-polynucleotide herbicides with similar modes of action are used in conjunction with a bioactive EPSPS trigger polynucleotide to control weeds. In several embodiments, compositions and methods that utilize alternative modes of action are used for difficult to control weed species. In some embodiments, two or more non-polynucleotide herbicides with different modes of action are used in conjunction with a bioactive EPSPS trigger polynucleotide to control weeds. In some embodiments, one or more non-polynucleotide herbicides with similar or different modes of action are used in conjunction with a bioactive EPSPS trigger polynucleotide and a bioactive trigger polynucleotide targeting a herbicide target gene other than EPSPS to control weeds. In some embodiments, a bioactive EPSPS trigger polynucleotide is used in conjunction with an EPSPS-inhibitor herbicide and an herbicide having a different mode of action. In some embodiments, a bioactive EPSPS trigger polynucleotide is used in conjunction with an EPSPS-inhibitor herbicide, a herbicide having a different mode of action and a bioactive trigger polynucleotide targeting a herbicide target gene other than EPSPS.

Several embodiments relate to compositions and methods that enhance the activity of non-polynucleotide herbicides. In some embodiments, the rates of use of the non-polynucleotide herbicides can be reduced in compositions comprising bioactive EPSPS trigger polynucleotides. For example, reductions in use rate of 10-25 percent, 26-50 percent, 51-75 percent or more can be achieved. In some embodiments, a bioactive EPSPS trigger polynucleotide can reduce the amount of an EPSPS-inhibitor herbicide used to effectively kill weeds by at least 10, 15, 20, 25, 30, 35, 40, 50, 55, 60, 65, 70, 75, or 80 percent.

In some embodiments, a bioactive EPSPS trigger polynucleotide is utilized in conjunction with one or more auxin-like herbicides to control weeds. Auxin-like herbicides include benzoic acid herbicide, phenoxy carboxylic acid herbicide, pyridine carboxylic acid herbicide, quinoline carboxylic acid herbicide, pyrimidine carboxylic acid herbicide, and benazolin-ethyl herbicide. Auxin-like herbicides also include phenoxy carboxylic acid compounds, pyridine carboxylic acid compounds, quinoline carboxylic acid compounds, and benazolin-ethyl compounds. Examples of phenoxy carboxylic acid compounds include, but are not limited to 2,4-dichlorophenoxyacetic acid, (4-chloro-2-methylphenoxy) acetic acid, diclorprop (2,4-DP), mecoprop (MCPP), and clomeprop. Examples of pyridine herbicides include, but are not limited to clopryalid, picloram, fluroxypyr, aminocyclopyrachlor and triclopyr. These auxin-like herbicides are useful in a tank mix, concomitantly, or pre or post treatment with the compositions. Auxin-like herbicides include commercially available formulations, for example, including but not limited to, 2,4-D, 2,4-DB (BUTYRAC® 200, Albaugh, LLC, Ankeny, Iowa; Bakker), MCPA (RHONOX®, RHOMENE®, Nufarm US, Morrisville, N.C.), mecoprop, dichlorprop, 2,4,5-T, triclopyr (GARLON®, Dow AgroSciences, Indianapolis, Ind.), chloramben, dicamba (BANVEL®, BASF Corporation, Ludwigshafen, Germany; CLARITY®, BASF Corporation, Ludwigshafen, Germany; ORACLE®, Gharda Chemicals Limited, Newtown, Pa.; STERLING BLUE®, Winfield Solutions, LLC, St. Paul, Minn.), 2,3,6-TBA, tricamba, clopyralid (STINGER®, Dow AgroSciences, Indianapolis, Ind.), picloram (TORDON®, Dow AgroSciences, Indianapolis, Ind.), quinmerac, quinclorac, benazolin, fenac, IAA, NAA, orthonil and fluroxypyr (VISTA®, STARANE®, Dow AgroSciences, Indianapolis, Ind.), aminopyralid (MILESTONE®, Dow AgroSciences, Indianapolis, Ind.) and aminocyclopyrachlor (Dupont, Wilmington, Del.).

In some embodiments, a bioactive EPSPS trigger polynucleotide is utilized in conjunction with one or more benzoic acid herbicides to control weeds. Benzoic acid herbicides are effective herbicides for both pre-emergence and post-emergence weed management. The benzoic acid herbicide group includes dicamba (3,6-dichloro-o-anisic acid), chloramben (3-amino-2,5-dichlorobenzoic acid), and TBA (2,3,6-trichlorobenzoic acid). Dicamba is one of the many auxin-like herbicides that is a low-cost, environmentally friendly herbicide that has been used as a pre-emergence and post-emergence herbicide to effectively control annual and perennial broadleaf weeds and several grassy weeds in corn, sorghum, small grains, pasture, hay, rangeland, sugarcane, asparagus, turf, and grass seed crops (*Crop Protection Chemicals Reference*, pp. 1803-1821, Chemical & Pharmaceutical Press, Inc., New York, N.Y., 11th ed., 1995). Dicamba refers to 3,6-dichloro-o-anisic acid or 3,6-dichloro-2-methoxy benzoic acid and its acids and salts. Its salts include isopropylamine, diglycoamine, dimethylamine, potassium and sodium. Examples of commercial formulations of dicamba include BANVEL™ (as DMA salt, BASF, Research Triangle Park, N.C.), CLARITY® (DGA salt, BASF Corporation, Ludwigshafen, Germany), VEL58CS11™ (BASF) and VANQUISH™ (DGA salt, BASF Corporation, Ludwigshafen, Germany). Dicamba is a useful herbicide as a tank mix, concomitantly, or pre or post treatment with the compositions.

Several embodiments relate to a method comprising providing a bioactive trigger polynucleotide to a herbicide-tolerant plant. In some embodiments, the herbicide-tolerant plant comprises a transgene that confers herbicide tolerance. Herbicides for which transgenes for plant tolerance have been demonstrated include, but are not limited to: auxin-like herbicides, glyphosate, glufosinate, sulfonylureas, imidazolinones, bromoxynil, delapon, dicamba, cyclohezane-dione, protoporphyrionogen oxidase inhibitors, and 4-hydroxyphenyl-pyruvate-dioxygenase inhibitors. Transgenes and their polynucleotide molecules that encode proteins involved in herbicide tolerance are known in the art. For example, transgenes and their polynucleotide molecules that encode proteins involved in herbicide tolerance include, but are not limited to: 5-enolpyruvylshikimate-3-phosphate synthase (EPSPS), for example, as more fully described in U.S. Pat. Nos. 7,807,791, 6,248,876 B1, 5,627,061, 5,804,425, 5,633,435, 5,145,783, 4,971,908, 5,312,910, 5,188,642, 4,940,835, 5,866,775, 6,225,114 B1, 6,130,366, 5,310,667, 4,535,060, 4,769,061, 5,633,448, 5,510,471, U.S. Pat. No. Re. 36,449; U.S. Pat. No. RE 37,287 E; and U.S. Pat. No. 5,491,288; tolerance to sulfonylurea and/or imidazolinone, for example, as described more fully in U.S. Pat. Nos. 5,605,011, 5,013,659, 5,141,870, 5,767,361, 5,731,180, 5,304,732, 4,761,373, 5,331,107, 5,928,937, 5,378,824, and International Publication WO96/33270; tolerance to hydroxyphenylpyruvatedioxygenases inhibiting herbicides in plants, for example, as described more fully in U.S. Pat. No. 6,245,968 B1, 6,268,549, 6,069,115, 7,312,379, 7,935, 869, 7,304,209; aryloxyalkanoate dioxygenase polynucleotides, which confer tolerance to 2,4-D and other phenoxy auxin herbicides as well as to aryloxyphenoxypropionate herbicides as described, for example, in U.S. Pat. No. 7,838,733 and International Publication WO2005/107437; and dicamba-tolerance polynucleotides as described, for example, in Herman et al. (2005) J. Biol. Chem. 280: 24759-24767. Other examples of herbicide-tolerance traits include those conferred by polynucleotides encoding an exogenous phosphinothricin acetyltransferase, such as described in U.S. Pat. Nos. 5,969,213; 5,489,520; 5,550, 318; 5,874,265; 5,919,675; 5,561,236; 5,648,477; 5,646, 024; 6,177,616; and 5,879,903. Plants containing an exogenous phosphinothricin acetyltransferase can exhibit improved tolerance to glufosinate herbicides, which inhibit the enzyme glutamine synthase. Additionally, herbicide-tolerance polynucleotides include those conferred by polynucleotides conferring altered protoporphyrinogen oxidase (protox) activity, as described in U.S. Pat. No. 6,288,306 B1; 6,282,837 B1; and 5,767,373; and International Publication WO2001/12825. Plants containing such polynucleotides can exhibit improved tolerance to any of a variety of herbicides which target the protox enzyme (also referred to as protox inhibitors). Polynucleotides encoding a glyphosate oxidoreductase and a glyphosate-N-acetyl transferase (GOX described in U.S. Pat. No. 5,463,175 and GAT described in U.S. Patent publication 20030083480, dicamba monooxy-genase U.S. Pat. Nos. 7,022,896 and 7,884,262, all of which are incorporated herein by reference); a polynucleotide molecule encoding bromoxynil nitrilase (Bxn described in U.S. Pat. No. 4,810,648 for Bromoxynil tolerance, which is incorporated herein by reference); a polynucleotide molecule encoding phytoene desaturase (crtl) described in Misawa et al, (1993) Plant J. 4:833-840 and Misawa et al, (1994) Plant J. 6:481-489 for norflurazon tolerance; a polynucleotide molecule encoding acetohydroxyacid synthase (AHAS, aka ALS) described in Sathasiivan et al. (1990) Nucl. Acids Res. 18:2188-2193 for tolerance to sulfonylurea herbicides; and the bar gene described in DeBlock, et al. (1987) EMBO J. 6:2513-2519 for glufosinate and bialaphos tolerance. The transgenic coding regions and regulatory elements of the herbicide tolerance genes are targets in which bioactive polynucleotide triggers and herbicides can be included in the composition and combinations thereof to provide for enhanced methods of weed control.

Transgenic crops with one or more herbicide tolerances may need specialized methods of management to control weeds. Several embodiments enable the targeting of a transgene for herbicide tolerance to permit the treated plants to become sensitive to the herbicide. For example, an EPSPS DNA contained in a transgenic crop event can be a target for bioactive trigger polynucleotides in order to render the transgenic crop sensitive to application of the corresponding glyphosate containing herbicide. Such transgenic events are known in the art and include but are not limited to DAS-44406-6, MON883302, MON87427, FG72, HCEM485, H7-1, ASR368, J101, J163, DP-098140, GHB614, 356043, MON89788, MON88913, RT200, NK603, GTSB77, GA21, MON1445, and 40-3-2 and US patent publications: 20110126310, 20090137395, herein incorporated in their entirety by reference hereto.

Several embodiments relate to the use of a bioactive EPSPS trigger polynucleotide in conjunction with one or more transfer agents. As used herein, a "transfer agent" is an agent that, when combined with a polynucleotide in a composition that is topically applied to a target plant surface, enables the polynucleotide to enter a plant cell. In some embodiments, a transfer agent is an agent that conditions the surface of plant tissue, e.g., leaves, stems, roots, flowers, or fruits, to permeation by bioactive trigger polynucleotides into plant cells. In certain aspects, methods include one or more applications of a bioactive trigger polynucleotide composition and one or more applications of a transfer agent for conditioning of a plant to permeation by bioactive trigger polynucleotides. The transfer of bioactive trigger polynucleotides into plant cells can be facilitated by the prior or contemporaneous application of a polynucleotide-transferring agent to the plant tissue. In some embodiments the transferring agent is applied subsequent to the application of the polynucleotide composition. Not wishing to be bound by a particular theory, the transfer agent enables bioactive trigger polynucleotides to pass through cuticle wax barriers, stomata and/or cell wall or membrane barriers into plant cells. Suitable transfer agents to facilitate transfer of the bioactive trigger polynucleotide into a plant cell include agents that increase permeability of the exterior of the plant or that increase permeability of plant cells to oligonucleotides or polynucleotides. Such agents to facilitate transfer of the bioactive trigger polynucleotide into a plant cell include a chemical agent, or a physical agent, or combinations thereof. Chemical agents for conditioning or transfer include (a) surfactants, (b) organic solvents or an aqueous solution or aqueous mixtures of organic solvents, (c) oxidizing agents, (d) acids, (e) bases, (f) oils, (g) enzymes, or combinations thereof. Embodiments of a method of providing a bioactive polynucleotide trigger to plant cells can optionally include an incubation step, a neutralization step (e.g., to neutralize an acid, base, or oxidizing agent, or to inactivate an enzyme), a rinsing step, or combinations thereof. Embodiments of agents or treatments for conditioning of a plant to permeation by bioactive trigger polynucleotides include emulsions, reverse emulsions, liposomes, and other micellar-like compositions. Embodiments of agents or treatments for conditioning of a plant to permeation by bioactive trigger polynucleotides include counter-ions or other molecules that are known to associate with nucleic acid molecules, e.g., inorganic ammonium ions, alkyl ammonium ions, lithium ions, polyamines such as spermine, spermidine, or putrescine, and other cations. Organic solvents useful in conditioning a plant to permeation by bioactive trigger polynucleotides include DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions). Naturally derived or synthetic oils with or without surfactants or emulsifiers can be used, e.g., plant-sourced oils, crop oils (such as those listed in the 9$^{th}$ Compendium of Herbicide Adjuvants, publicly available on the worldwide web (internet) at herbicide.adjuvants.com) can be used, e.g., paraffinic oils, polyol fatty acid esters, or oils with short-chain molecules modified with amides or polyamines such as polyethyleneimine or N-pyrrolidine.

In several embodiments, the transfer agent is an organosilicone preparation. In certain embodiments, an organosilicone preparation that is commercially available as SIL-WET® L-77 surfactant having CAS Number 27306-78-1 and EPA Number: CAL.REG.NO. 5905-50073-AA, and currently available from Momentive Performance Materials, Albany, N.Y. can be used to prepare a bioactive trigger polynucleotide composition. In certain embodiments where a SILWET® L-77 organosilicone preparation is used as a pre-spray treatment of plant leaves or other plant surfaces, freshly made concentrations in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of bioactive trigger polynucleotide molecules into plant cells from a topical application on the surface. In certain embodiments of the methods and compositions provided herein, a composition that comprises a bioactive trigger polynucleotide molecule and an organosilicone preparation comprising SILWET® L-77 in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

In certain embodiments, any commercially available organosilicone preparation is used or provided. For example, one or more of the following commercially available organosilicone preparations can be used as transfer agents in a bioactive trigger polynucleotide composition or applied as a pre-spray treatment to prepare a leaf or other plant surface for transfer of bioactive trigger polynucleotide molecules into plant cells: BREAK-THRU® S 321, BREAK-THRU® S 200 Cat#67674-67-3, BREAK-THRU® OE 441 Cat#68937-55-3, BREAK-THRU® S 278 Cat #27306-78-1, BREAK-THRU® S 243, BREAK-THRU® S 233 Cat#134180-76-0, available from manufacturer Evonik Goldschmidt (Germany), SILWET® HS 429, SILWET® HS 312, SILWET® HS 508, SILWET® HS 604 (Momentive Performance Materials, Albany, N.Y.). In certain embodiments where an organosilicone preparation is used as a pre-spray treatment of plant leaves or other surfaces, freshly made concentrations in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of bioactive trigger polynucleotide molecules into plant cells from a topical application on the surface. In certain embodiments of the methods and compositions provided herein, a composition that comprises a bioactive trigger polynucleotide molecule and an organosilicone preparation in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

Organosilicone preparations used in the methods and compositions provided herein can comprise one or more effective organosilicone compounds. As used herein, the phrase "effective organosilicone compound" is used to describe any organosilicone compound that is found in an organosilicone preparation that promotes internalization of a bioactive trigger polynucleotide into a plant cell. In certain embodiments, an effective organosilicone compound can enable a bioactive trigger polynucleotide to enter a plant cell in a manner permitting bioactive trigger polynucleotide mediated suppression of target gene expression in the plant cell. In general, effective organosilicone compounds include, but are not limited to, compounds that can comprise: i) a trisiloxane head group that is covalently linked to, ii) an alkyl linker including, but not limited to, an n-propyl linker, that is covalently linked to, iii) a poly glycol chain, that is covalently linked to, iv) a terminal group. Trisiloxane head groups of such effective organosilicone compounds include, but are not limited to, heptamethyltrisiloxane. Alkyl linkers can include, but are not limited to, an n-propyl linker. Poly glycol chains include, but are not limited to, polyethylene glycol or polypropylene glycol. Poly glycol chains can comprise a mixture that provides an average chain length "n" of about "7.5". In certain embodiments, the average chain length "n" can vary from about 5 to about 14. Terminal groups can include, but are not limited to, alkyl groups such as a methyl group. Effective organosilicone compounds are believed to include, but are not limited to, trisiloxane ethoxylate surfactants or polyalkylene oxide modified heptamethyl trisiloxane.

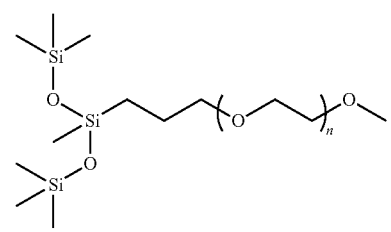

(Compound I: polyalkyleneoxide heptamethyltrisiloxane, average n = 7.5).

In certain embodiments, an organosilicone preparation that comprises an organosilicone compound comprising a trisiloxane head group is used in the methods and compositions provided herein. In certain embodiments, an organosilicone preparation that comprises an organosilicone compound comprising a heptamethyltrisiloxane head group is used in the methods and compositions provided herein. In certain embodiments, an organosilicone composition that comprises Compound I is used in the methods and compositions provided herein. In certain embodiments, an organosilicone composition that comprises Compound I is used in the methods and compositions provided herein. In certain embodiments of the methods and compositions provided herein, a composition that comprises a bioactive trigger polynucleotide molecule and one or more effective organosilicone compound in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

In several embodiments, the transfer agent is a plant hormone. Examples of plant hormones include abscisic acid, auxin, cytokinin, gibberellin, jasmonate, ethylene, salicyclic acid, nitric oxide, a strigolactone. In some embodiments, the transfer agent is the plant hormone, Brassinosteroid.

In several embodiments, the transfer agent is a cationic lipid. As used herein, "cationic lipid" refers to a compound that includes at least one lipid moiety and a positively charged quaternary nitrogen associated with a counterion. "Lipids" are understood to be comprised of a hydrophobic alkyl or alkenyl moiety and a carboxylic acid or ester moiety. In some embodiments one ore more bioactive trigger molecules interact with cationic lipids to form nucleic acid lipid particles. In some embodiments, the bioactive trigger molecules are encapsulated in a liposome so that the bioactive trigger molecules is inaccessible to an aqueous medium. In some embodiments, the liposome will have a solid core comprised of bioactive trigger molecules; such liposomes encapsulating bioactive trigger molecules and having a solid core are termed "lipid nanoparticles" herein. In some embodiments, the bioactive trigger molecules are not encapsulated by a liposome. In such embodiments, the bioactive trigger molecules can be complexed on the outer surface of the. In these embodiments, the bioactive trigger molecules is accessible to the aqueous medium. In some embodiments, the cationic lipids can be used in combination with other lipid components such as cholesterol and PEG-lipids to form lipid nanoparticles with bioactive trigger molecules.

In several embodiments, expression of an EPSPS gene in a plant is modulated by (a) conditioning of a plant to permeation by bioactive trigger polynucleotides and (b) treatment of the plant with the bioactive trigger polynucleotides, wherein the bioactive trigger polynucleotides include at least one segment of 18 or more contiguous nucleotides cloned from or otherwise identified from the target EPSPS gene in either anti-sense or sense orientation, whereby the bioactive trigger polynucleotide molecules permeate the interior of the plant and induce modulation of the target gene. The conditioning and polynucleotide application can be performed separately or in a single step. When the conditioning and bioactive trigger polynucleotide application are performed in separate steps, the conditioning can precede or can follow the bioactive trigger polynucleotide application within minutes, hours, or days. In some embodiments more than one conditioning step or more than one application of bioactive trigger polynucleotide molecules can be performed on the same plant.

In some embodiments, ligands can be tethered to a bioactive trigger polynucleotide, for example a dsRNA, ssRNA, dsDNA or ssDNA trigger polynucleotide. Ligands in general can include modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids (e.g., cholesterol, a bile acid, or a fatty acid (e.g., lithocholic-oleyl, lauroyl, docosnyl, stearoyl, palmitoyl, myristoyl oleoyl, linoleoyl), steroids (e.g., uvaol, hecigenin, diosgenin), terpenes (e.g., triterpenes, e.g., sarsasapogenin, Friedelin, epi-friedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. The ligand may also be a recombinant or synthetic molecule, such as a synthetic polymer, e.g., polyethylene glycol (PEG), PEG-40K, PEG-20K and PEG-5K. Other examples of ligands include lipophilic molecules, e.g., cholesterol, cholic acid, adamantane acetic acid, 1-pyrene butyric acid, dihydrotestosterone, glycerol (e.g., esters and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., lauroyl, docosnyl, stearoyl, oleoyl, linoleoyl 1,3-bis-O(hexadecyl)glycerol, 1,3-bis-O(octaadecyl)glycerol), geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dodecanoyl, lithocholyl, 5β-cholanyl, N,N-distearyl-lithocholamide, 1,2-di-O-stearoylglyceride, dimethoxytrityl, or phenoxazine) and PEG (e.g., PEG-5K, PEG-20K, PEG-40K). In some embodiments, the lipophilic moieties are selected from a group consisting of lipid, cholesterols, oleyl, retinyl, and cholesteryl residues.

In some embodiments, conjugating a ligand to a bioactive trigger polynucleotide, for example dsRNA, enhances its cellular absorption. In some embodiments, a lipophilic moiety is conjugated to a bioactive trigger polynucleotide, for example dsRNA. Lipophilic compounds that may be conjugated to a bioactive trigger polynucleotide include, but are not limited to, 1-pyrene butyric acid, 1,3-bis-O-(hexadecyl) glycerol, and menthol. One example of a ligand for receptor-mediated endocytosis is folic acid. Folic acid enters the cell by folate-receptor-radiated endocytosis. Bioactive trigger polynucleotides bearing folic acid would be efficiently transported into the cell via the folate-receptor-mediated endocytosis. Other ligands that have been conjugated to polynucleotides include polyethylene glycols, carbohydrate clusters, cross-linking agents, porphyrin conjugates, delivery peptides and lipids such as cholesterol. In certain instances, conjugation of a cationic ligand to polynucleotides results in improved resistance to nucleases. Representative examples of cationic ligands are propylammonium and dimethylpropylammonium. Interestingly, antisense polynucleotides were reported to retain their high binding affinity to mRNA when the cationic ligand was dispersed, throughout the oligonucleotide. See M. Manoharan Antisense & Nucleic Acid Drug Development 2002, 12, 103 and references therein.

Delivery of bioactive trigger nucleotides to the interior of a plant cell can be accomplished by a variety of methods including, without limitation, (1) loading liposomes with a trigger polynucleotide provided herein and (2) complexing a trigger polynucleotide with lipids or liposomes to form nucleic acid-lipid or nucleic acid-liposome complexes. The liposome can be composed of cationic and neutral lipids commonly used to transfect cells in vitro. Cationic lipids can complex (e.g., charge-associate) with negatively charged, nucleic acids to form liposomes. Examples of cationic liposomes include, without limitation, LIPOFECTIN® (Invitrogen/Life Technologies, Carlsbad, Calif.; a 1:1 (w/w) liposome formulation of the cationic lipid N-[1-(2,3-dioleyloxy)propyl]-n,n,n-trimethylammonium chloride (DOTMA)), LIPOFECTAMINE® (Invitrogen/Life Technologies, Carlsbad, Calif.; a cationic liposome formulation with a neutral co-lipid), LIPOFECTACE® (Invitrogen/Life Technologies, Carlsbad, Calif.; a 1:2.5 (w/w) formulation of dimethyldioctadecylammonium bromide and dioleoylphosphatidylethanolamine), and DOTAP. Procedures for forming liposomes are well known in the art. Liposome compositions can be formed, for example, from phosphatidylcholine, dimyristoyl phosphatidylcholine, dipalmitoyl phosphatidylcholine, dimyristoyl phosphatidyl glycerol, dioleoyl phosphatidylethanolamine or liposomes comprising dihydrosphingomyelin (DHSM). Numerous lipophilic agents are commercially available, including LIPOFECTIN® (Invitrogen/Life Technologies, Carlsbad, Calif.) and EFFECTENE™ (Qiagen, Valencia, Calif.; a non-liposomal lipid formulation in conjunction with a DNA-condensing enhancer). In addition, systemic delivery methods can be optimized using commercially available cationic lipids such as DDAB or DOTAP, each of which can be mixed with a neutral lipid such as DOPE or cholesterol. In some eases, liposomes such as those described by Templeton et al. (Nature Biotechnology, 15:647-652 (1997)) can be used. In other embodiments, polycations such as polyethyleneimine can be used to achieve delivery in vivo and ex vivo (Boletta et al., J. Am Soc. Nephrol. 7:1728 (1996)). Additional information regarding the use of liposomes to deliver nucleic acids can be found in U.S. Pat. No. 6,271,359, PCT Publication WO 96/40964 and Morrissey, D. et al. 2005. Nat Biotechnol. 23(8):1002-7.

In some embodiments, the bioactive trigger polynucleotide compositions may also be used as mixtures with various agricultural chemicals and/or insecticides, miticides and fungicides, pesticidal and biopesticidal agents. Examples include but are not limited to azinphos-methyl, acephate, isoxathion, isofenphos, ethion, etrimfos, oxydemeton-methyl, oxydeprofos, quinalphos, chlorpyrifos, chlorpyrifos-methyl, chlorfenvinphos, cyanophos, dioxabenzofos, dichlorvos, disulfoton, dimethylvinphos, dimethoate, sulprofos, diazinon, thiometon, tetrachlorvinphos, temephos, tebupirimfos, terbufos, naled, vamidothion, pyraclofos, pyridafenthion, pirimiphos-methyl, fenitrothion, fenthion, phenthoate, flupyrazophos, prothiofos, propaphos, profenofos, phoxime, phosalone, phosmet, formothion, phorate, malathion, mecarbam, mesulfenfos, methamidophos, methidathion, parathion, methyl parathion, monocrotophos, trichlorphon, EPN, isazophos, isamidofos, cadusafos, diamidaphos, dichlofenthion, thionazin, fenamiphos, fosthiazate, fosthietan, phosphocarb, DSP, ethoprophos, alanycarb, aldicarb, isoprocarb, ethiofencarb, carbaryl, carbosulfan, xylylcarb, thiodicarb, pirimicarb, fenobucarb, furathiocarb, propoxur, bendiocarb, benfuracarb, methomyl, metolcarb, XMC, carbofuran, aldoxycarb, oxamyl, acrinathrin, allethrin, esfenvalerate, empenthrin, cycloprothrin, cyhalothrin, gamma-cyhalothrin, lambda-cyhalothrin, cyfluthrin, beta-cyfluthrin, cypermethrin, alpha-cypermethrin, zeta-cypermethrin, silafluofen, tetramethrin, tefluthrin, deltamethrin, tralomethrin, bifenthrin, phenothrin, fenvalerate, fenpropathrin, furamethrin, prallethrin, flucythrinate, fluvalinate, flubrocythrinate, permethrin, resmethrin, ethofenprox, cartap, thiocyclam, bensultap, acetamiprid, imidacloprid, clothianidin, dinotefuran, thiacloprid, thiamethoxam, nitenpyram, chlorfluazuron, diflubenzuron, teflubenzuron, triflumuron, novaluron, noviflumuron, bistrifluoron, fluazuron, flucycloxuron, flufenoxuron, hexaflumuron, lufenuron, chromafenozide, tebufenozide, halofenozide, methoxyfenozide, diofenolan, cyromazine, pyriproxyfen, buprofezin, methoprene, hydroprene, kinoprene, triazamate, endosulfan, chlorfenson, chlorobenzilate, dicofol, bromopropylate, acetoprole, fipronil, ethiprole, pyrethrin, rotenone, nicotine sulphate, BT (*Bacillus Thuringiensis*) agent, spinosad, abamectin, acequinocyl, amidoflumet, amitraz, etoxazole, chinomethionat, clofentezine, fenbutatin oxide, dienochlor, cyhexatin, spirodiclofen, spiromesifen, tetradifon, tebufenpyrad, binapacryl, bifenazate, pyridaben, pyrimidifen, fenazaquin, fenothiocarb, fenpyroximate, fluacrypyrim, fluazinam, flufenzin, hexythiazox, propargite, benzomate, polynactin complex, milbemectin, lufenuron, mecarbam, methiocarb, mevinphos, halfenprox, azadirachtin, diafenthiuron, indoxacarb, emamectin benzoate, potassium oleate, sodium oleate, chlorfenapyr, tolfenpyrad, pymetrozine, fenoxycarb, hydramethylnon, hydroxy propyl starch, pyridalyl, flufenerim, flubendiamide, flonicamid, metaflumizole, lepimectin, TPIC, albendazole, oxibendazole, oxfendazole, trichlamide, fensulfothion, fenbendazole, levamisole hydrochloride, morantel tartrate, dazomet, metam-sodium, triadimefon, hexaconazole, propiconazole, ipconazole, prochloraz, triflumizole, tebuconazole, epoxiconazole, difenoconazole, flusilazole, triadimenol, cyproconazole, metconazole, fluquinconazole, bitertanol, tetraconazole, triticonazole, flutriafol, penconazole, diniconazole, fenbuconazole, bromuconazole, imibenconazole, simeconazole, myclobutanil, hymexazole, imazalil, furametpyr, thifluzamide, etridiazole, oxpoconazole, oxpoconazole fumarate, pefurazoate, prothioconazole, pyrifenox, fenarimol, nuarimol, bupirimate, mepanipyrim, cyprodinil, pyrimethanil, metalaxyl, mefenoxam, oxadixyl, benalaxyl, thiophanate, thiophanate-methyl, benomyl, carbendazim, fuberidazole, thiabendazole, manzeb, propineb, zineb, metiram, maneb, ziram, thiuram, chlorothalonil, ethaboxam, oxycarboxin, carboxin, flutolanil, silthiofam, mepronil, dimethomorph, fenpropidin, fenpropimorph, spiroxamine, tridemorph, dodemorph, flumorph, azoxystrobin, kresoxim-methyl, metominostrobin, orysastrobin, fluoxastrobin, trifloxystrobin, dimoxystrobin, pyraclostrobin, picoxystrobin, iprodione, procymidone, vinclozolin, chlozolinate, flusulfamide, dazomet, methyl isothiocyanate, chloropicrin, methasulfocarb, hydroxyisoxazole, potassium hydroxyisoxazole, echlomezol, D-D, carbam, basic copper chloride, basic copper sulfate, copper nonylphenolsulfonate, oxine copper, DBEDC, anhydrous copper sulfate, copper sulfate pentahydrate, cupric hydroxide, inorganic sulfur, wettable sulfur, lime sulfur, zinc sulfate, fentin, sodium hydrogen carbonate, potassium hydrogen carbonate, sodium hypochlorite, silver, edifenphos, tolclofos-methyl, fosetyl, iprobenfos, dinocap, pyrazophos, carpropamid, fthalide, tricyclazole, pyroquilon, diclocymet, fenoxanil, kasugamycin, validamycin, polyoxins, blasticiden S, oxytetracycline, mildiomycin, streptomycin, rape seed oil, machine oil, benthiavalicarbisopropyl, iprovalicarb, propamocarb, diethofencarb, fluoroimide, fludioxanil, fenpiclonil, quinoxyfen, oxolinic acid, chlorothalonil, captan, folpet, probenazole, acibenzolar-S-methyl, tiadinil, cyflufenamid, fenhexamid, diflumetorim, metrafenone, picobenzamide, proquinazid, famoxadone, cyazofamid, fenamidone, zoxamide, boscalid, cymoxanil, dithianon, fluazinam, dichlofluanide, triforine, isoprothiolane, ferimzone, diclomezine, tecloftalam, pencycuron, chinomethionat, iminoctadine acetate, iminoctadine albesilate, ambam, polycarbamate, thiadiazine, chloroneb, nickel dimethyldithiocarbamate, guazatine, dodecylguanidine-acetate, quintozene, tolylfluanid, anilazine, nitrothalisopropyl, fenitropan, dimethirimol, benthiazole, harpin protein, flumetover, mandipropamide and penthiopyrad.

In some embodiments, an agronomic field in need of weed control is treated by application of an agricultural chemical composition directly to the surface of the growing plants, such as by a spray. For example, a composition comprising a bioactive trigger polynucleotide and one or more of a transfer agent and a non-polynucleotide herbicide is applied to control weeds in a field of crop plants by spraying the field with the composition. The composition can be provided as a tank mix with one or more herbicidal chemicals and additional pesticidal chemicals to control pests and diseases of the crop plants in need of pest and disease control. In some embodiments, a sequential treatment of components (for example, the bioactive trigger polynucleotide-containing composition followed by the herbicide), or a simultaneous treatment or mixing of one or more of the components of the composition from separate containers is contemplated. Treatment of the field can occur as often as needed to provide weed control and the components of the composition can be adjusted to target specific weed species or weed families through utilization of specific bioactive trigger polynucleotides or bioactive trigger polynucleotide-containing compositions capable of selectively targeting the specific species or plant family to be controlled. The composition can be applied at effective use rates according to the time of application to the field, for example, preplant, at planting, post planting, and post harvest. Glyphosate can be applied to a field at rates of 11-44 ounces/acre up to 7.2875 pounds/acre. The bioactive trigger polynucleotides of the composition can be applied at rates of 1 to 30 grams per acre depending on the number of bioactive trigger polynucleotide molecules needed for the scope of weeds in the field.

Crop plants in which weed control may be needed include but are not limited to corn, soybean, cotton, canola, sugar beet, alfalfa, sugarcane, rice, and wheat; vegetable plants including, but not limited to, tomato, sweet pepper, hot pepper, melon, watermelon, cucumber, eggplant, cauliflower, broccoli, lettuce, spinach, onion, peas, carrots, sweet corn, Chinese cabbage, leek, fennel, pumpkin, squash or gourd, radish, Brussels sprouts, tomatillo, garden beans, dry beans, or okra; culinary plants including, but not limited to, basil, parsley, coffee, or tea; or fruit plants including but not limited to apple, pear, cherry, peach, plum, apricot, banana, plantain, table grape, wine grape, citrus, avocado, mango, or berry; a tree grown for ornamental or commercial use, including, but not limited to, a fruit or nut tree; ornamental plant (e.g., an ornamental flowering plant or shrub or turf grass). The methods and compositions provided herein can also be applied to plants that are not grown from seed, including fruit trees and plants that include, but are not limited to, avocados, tomatoes, eggplant, cucumber, melons, watermelons, and grapes as well as various ornamental plants. For example, methods and compositions provided herein can also be applied to plants produced by a cutting, cloning, or grafting process.

All publications, patents and patent applications are herein incorporated by reference to the same extent as if each individual publication or patent application was specifically and individually indicated to be incorporated by reference.

The following Examples are presented for the purposes of illustration and should not be construed as limitations.

EXAMPLES

Example 1. EPSPS Target and Trigger Sequences

A major mechanism of glyphosate resistance in weeds is through amplification of the gene encoding 5-enolpyruvylshikimate-3-phosphate synthase (EPSPS). For example, genotyping of glyphosate-resistant *Palmer amaranth* has revealed glyphosate-resistant plants with 4 to more than 100 copies of the EPSPS gene. Bioactive trigger polynucleotide molecules targeting the EPSPS gene for down regulation are useful in controlling herbicide resistant weeds.

As shown in Table 1, two dsRNA molecules were designed using *Palmer amaranth* EPSPS cDNA sequence (SEQ ID NO: 1) to comprise an anti-sense strand that is complementary to positions 398-447 (SEQ ID NO: 4) or positions 1189-1241 (SEQ ID NO: 6) of *Amaranthus palmeri* EPSPS cDNA. The *Palmer amaranth* EPSPS sequences targeted by the bioactive dsRNA triggers are indicated by the lowercase nucleotides. The two bioactive dsRNA trigger molecules are further capable of hybridizing with mRNA transcribed from the *Amaranthus rudis* (waterhemp) EPSPS gene (SEQ ID NO: 2). As shown in Table 1, SEQ ID NO: 4 complements *Amaranthus rudis* EPSPS at positions 398-427, 429-433, and 435-447 as indicated by the lowercase nucleotides, with two mismatches at positions 428 and 434 (underlined). SEQ ID NO: 6 complements *Amaranthus rudis* EPSPS at positions 1189-1202, and 1204-1241 as indicated by the lowercase nucleotides, with one mismatch at position 1203 (underlined).

TABLE 1

EPSPS target and trigger sequences SEQ ID NOs: 1-8

| SEQ ID NO: | Description | Sequence |
|---|---|---|
| 1 | EPSPS cDNA *Amaranthus palmeri* | ATGGCTCAAGCTACTACCATCAACAATGGTGTCCATACTGGTCAAT<br>TGCACCATACTTTACCCAAAACCCAGTTACCCAAATCTTCAAAAAC<br>TCTTAATTTTGGATCAAACTTGAGAATTTCTCCAAAGTTCATGTCTT<br>TAACCAATAAAAGAGTTGGTGGGCAATCATCAATTGTTCCCAAGA<br>TTCAAGCTTCTGTTGCTGCTGCAGCTGAGAAACCTTCATCTGTCCC<br>AGAAATTGTGTTACAACCCATCAAAGAGATCTCTGGTACTGTTCAA<br>TTGCCTGGGTCAAAGTCTTTATCCAATCGAATCCTTCTTTTAGCTGC<br>TTTGTCTGAGGGCACAACAGTGGTCGACAACTTGCTGTATAGTGAT<br>GATATTCTTTATATGTTGGACGCTCTCAgaactcttggtttaaaagtggaggatgata<br>gtacagccaaaagggcagtcGTAGAGGGTTGTGGTGGTCTGTTTCCTGTTGGT<br>AAAGATGGAAAGGAAGAGATTCAACTTTTCCTTGGTAATGCAGGA<br>ACAGCGATGCGCCCATTGACAGCTGCGGTTGCCGTTGCTGGAGGA |

TABLE 1-continued EPSPS target and trigger sequences SEQ ID NOs: 1-8

| SEQ ID NO: | Description | Sequence |
|---|---|---|
| | | AATTCAAGTTATGTGCTTGATGGAGTACCAAGAATGAGGGAGCGC<br>CCCATTGGGGATCTGGTAGCAGGTCTAAAGCAACTTGGTTCAGATG<br>TAGATTGTTTTCTTGGCACAAATTGCCCTCCTGTTCGGGTCAATGCT<br>AAAGGAGGCCTTCCAGGGGGCAAGGTCAAGCTCTCTGGATCGGTT<br>AGTAGCCAATATTTAACTGCACTTCTCATGGCTACTCCTTTGGGTCT<br>TGGAGACGTGGAGATTGAGATAGTTGATAAATTGATTTCTGTACCG<br>TATGTTGAAATGACAATAAAGTTGATGGAACGCTTTGGAGTATCCG<br>TAGAACATAGTGATAGTTGGGACAGGTTCTACATTCGAGGTGGTC<br>AGAAATACAAATCTCCTGGAAAGGCATATGTTGAGGGTGATGCTT<br>CAAGTGCTAGCTACTTCCTAGCCGGAGCCGCCGTCACTGGTGGGAC<br>TGTCACTGTCAAGGGTTGTGGAACAAGCAGTTTACAGGGTGATGT<br>AAAATTTGCCGAAGTTCTTGAGAAGATGGGTTGCAAGGTCACCTG<br>GACAGAGAATAGTGTAACTGTTACTGGACCACCCAGGGATTCATC<br>TGGAAAGAAACATCTGCGTGCTATCgacgtcaacatgaacaaaatgccagatgttgct<br>atgactcttgcagttgttgcCTTGTATGCAGATGGGCCCACCGCCATCAGAGAT<br>GTGGCTAGCTGGAGAGTGAAGGAAACCGAACGGATGATTGCCATT<br>TGCACAGAACTGAGAAAGCTTGGGGCAACAGTTGAGGAAGGATCT<br>GATTACTGTGTGATCACTCCGCCTGAAAAGCTAAACCCCACCGCCA<br>TTGAAACTTATGACGATCACCGAATGGCCATGGCATTCTCTCTTGC<br>TGCCTGTGCAGATGTTCCCGTCACTATCCTTGATCCGGGATGCACC<br>CGTAAAACCTTCCCGGACTACTTTGATGTTTTAGAAAAGTTCGCCA<br>AGCATTGA |
| 2 | EPSPS<br>Amaranthus<br>rudis | ATGGCTCAAGCTACTACCATCAACAATGGTGTCCAAACTGGTCAAT<br>TGCACCATACTTTACCCAAAACCCACTTACCCAAATCTTCAAAAAC<br>TGTTAATTTTGGATCAAACTTTAGAATTTCTCCAAAGTTCATGTCTT<br>TAACCAATAAAAGAGTTGGTGGGCAATCATCAATTATTCCCAAGA<br>TTCAAGCTTCAGTTGCTGCTGCAGCTGAGAAACCTTCATCTGTCCC<br>AGAAATTGTGTTACAACCCATCAAAGAGATCTCTGGTACCATTCAA<br>TTGCCTGGGTCAAAGTCTCTATCTAATCGAATCCTTCTTTTAGCTGC<br>TTTGTCTCAGGGCACAACTGTGGTCGACAACTTGCTGTATAGTGAT<br>GATATTCTTTATATGTTGGACGCTCTCAgaactcttggtttaaaagtggaggatgata<br>AtacagAcaaaagggcagtcGTGGAGGGTTGTGGTGGTCTGTTTCCTGTTGG<br>TAAAGATGGAAAGGAAGAGATTCAACTTTTCCTTGGAAATGCAGG<br>AACAGCGATGCGCCCATTGACAGCTGCGGTTGCCGTTGCTGGAGG<br>AAATTCAAGCTATGTTCTTGACGGAGTACCAAGAATGAGGGAGCG<br>CCCCATTGGGGATCTGGTAGCAGGTCTAAAGCAACTTGGTTCAGAT<br>GTTGACTGTTTTCTTGGCACAAATTGCCCTCCTGTTCGGGTCAATGC<br>TAAAGGAGGCCTTCCAGGGGGCAAGGTCAAGCTCTCTGGATCGGT<br>TAGTAGCCAATATTTAACTGCACTTCTGATGGCTACTCCTTTGGGT<br>CTTGGAGATGTGGAGATTGAGATAGTTGATAAATTGATTTCCGTAC<br>CGTATGTTGAAATGACAATAAGGTTGATGGAACGCTTTGGAGTATC<br>TGTTGAACATAGTGATAGTTGGGACAGGTTCTTCATCCGAGGTGGT<br>CAGAAATACAAATCTCCTGGAAAGGCATATGTTGAGGGTGACGCT<br>TCAAGTGCTAGCTACTTCCTAGCTGGAGCCGCCGTCACTGGGGGA<br>CTGTGACTGTCAAGGGTTGTGGAACAAGCAGTTTACAGGGTGATG<br>TAAAATTTGCCGAAGTTCTTGAGAAGATGGGTTGCAAGGTCACCTG<br>GACAGACAATAGCGTAACTGTTACTGGACCACCCAGGGAATCATC<br>TGGAAGGAAACATTTGCGCGCTATCgacgtcaacatgaaTaaaatgccagatgttgct<br>atgactcttgcagttgttgcCTTGTATGCAGATGGGCCCACCGCCATTAGAGAT<br>GTGGCTAGCTGGAGAGTGAAGGAAACCGAACGGATGATTGCCATT<br>TGCACAGAACTGAGAAAGCTTGGGGCAACAGTTGAGGAAGGATCT<br>GATTACTGTGTGATCACTCCGCCTGAAAAGCTGATACCCACCGCCA<br>TCGAAACTTATGACGATCACCGAATGGCCATGGCATTCTCTCTTGC<br>TGCCTGTGCTGATGTTCCCGTCACTATCCTTGATCCGGGATGTACA<br>CGTAAAACCTTCCCGGACTACTTTGATGTCTTAGAAAAGTTCGCCA<br>AGCATTGA |
| 3 | 50mer EPSPS<br>Trigger | GAACUCUUGGUUUAAAAGUGGAGGAUGAUAGUACAGCCAAAAG<br>GGCAGUC |
| 4 | Reverse<br>Complement | GACUGCCCUUUUGGCUGUACUAUCAUCCUCCACUUUUAAACCAA<br>GAGUUC |
| 5 | 53mer EPSPS<br>Trigger | GACGUCAACAUGAACAAAAUGCCAGAUGUUGCUAUGACUCUUGC<br>AGUUGUUGC |
| 6 | Reverse<br>Complement | GCAACAACUGCAAGAGUCAUAGCAACAUCUGGCAUUUUGUUCAU<br>GUUGACGUC |
| 7 | 24mer EPSPS<br>Trigger | AUGCCAGAUGUUGCUAUGACUCUU |

TABLE 1-continued

EPSPS target and trigger sequences SEQ ID NOs: 1-8

| SEQ ID NO: | Description | Sequence |
|---|---|---|
| 8 | Reverse Complement | AAGAGUCAUAGCAACAUCUGGCAU |

A number of plant species contain an EPSPS gene. For example, a gene encoding an EPSPS polynucleotide molecule occurs naturally in the genome of *Amaranthus palmeri, Amaranthus rudis, Amaranthus albus, Amaranthus chlorostachys, Amaranthus graecizans, Amaranthus hybridus, Amaranthus lividus, Amaranthus spinosus, Amaranthus thunbergii, Amaranthus viridis, Lolium multiflorum, Lolium rigidium, Ambrosia artemisiifolia, Ambrosia trifida, Euphorbia heterophylla, Kochia scoparia, Abutilon theophrasti, Sorghum halepense, Chenopodium album, Commelina diffusa, Convulvulus arvensis, Conyza candensis, Digitaria sanguinalis,* and *Xanthium strumarium*. The nucleotide sequences of SEQ ID NO 3 and SEQ ID NO 5 were compared to the EPSPS gene sequences of various plant species and target sequences having at least 85% identity or complementarity to SEQ ID NOs 3-6 were identified. EPSPS target sequences identified as having at least 85% identity or complementarity to SEQ ID NOs 3-6 are shown in Table 2 (mismatches are underlined). Bioactive trigger polynucleotides comprising a nucleotide sequence having at least 85% identity or complementarity to SEQ ID NOs: 9-35 are contemplated for down regulating EPSPS expression and controlling herbicide resistant weeds.

TABLE 2

EPSPS target nucleotide sequences SEQ ID NOs: 9-35

| SEQ ID NO: | Species | Corresponding to: | Sequence | Length |
|---|---|---|---|---|
| 9 | *Amaranthus graecizans* | SEQ ID NO: 3 | GAGCTCTTGGTTTAAAAGTGGAGGATGAT A<u>A</u>TACAGCCAAAAGGGCAGT | 49 |
| 10 | *Amaranthus hybridus* | SEQ ID NO: 3 | GAACTCTTGGTTTAAAAGTGGAGGATGAT A<u>A</u>TACAGCCAAAAGGGCAGTC | 50 |
| 11 | *Amaranthus palmeri* | SEQ ID NO: 3 | GAACTCTTGGTTTAAAAGTGGAGGATGAT AGTACAGCCAAAAGGGCAGTC | 50 |
| 12 | *Amaranthus rudis* | SEQ ID NO: 3 | GAACTCTTGGTTTAAAAGTGGAGGATGAT A<u>A</u>TACAG<u>A</u>CAAAAGGGCAGTC | 50 |
| 13 | *Amaranthus viridis* | SEQ ID NO: 3 | GAACTCTTGGTTTAAAAGTGGAGGATGAT A<u>A</u>TACAGCCAAAAGGGCAGTC | 50 |
| 14 | *Abutilon theophrasti* | SEQ ID NO: 5 | GATGTCAACATGAACAAAATGCCAGATGT TGC<u>C</u>ATGACTCT<u>C</u>GC<u>T</u>GTTGTTGC | 53 |
| 15 | *Amaranthus graecizans* | SEQ ID NO: 5 | GACGTCAACATGAACAAAATGCCAGATGT TGCTATGACTCTTGCAGTTGTTGC | 53 |
| 16 | *Amaranthus hybridus* | SEQ ID NO: 5 | GACGTCAACATGAACAAAATGCCAGATGT TGCTATGACTCTTGCAGT<u>A</u>GTTGC | 53 |
| 17 | *Amaranthus lividus* | SEQ ID NO: 5 | GACGTCAACATGAACAAAATGCCAGATGT TGCTATGACTCTTGCAGT<u>A</u>GTTGC | 53 |
| 18 | *Amaranthus palmeri* | SEQ ID NO: 5 | GACGTCAACATGAACAAAATGCCAGATGT TGCTATGACTCTTGCAGTTGTTGC | 53 |
| 19 | *Amaranthus rudis* | SEQ ID NO: 5 | GACGTCAACATGAA<u>T</u>AAAATGCCAGATGT TGCTATGACTCTTGCAGTTGTTGC | 53 |
| 20 | *Amaranthus thunbergii* | SEQ ID NO: 5 | GACGTCAACATGAACAAAATGCCAGATGT TGCTATGACTCTTGCAGT<u>A</u>GTTGC | 53 |
| 21 | *Amaranthus viridis* | SEQ ID NO: 5 | GACGTCAACATGAACAAAATGCCAGATGT TGCTATGACTCTTGCAGT<u>A</u>GTTGC | 53 |
| 22 | *Ambrosia trifida* | SEQ ID NO: 5 | GA<u>T</u>GT<u>T</u>AACATGAACAAAATGCCAGATGT TGC<u>C</u>ATGAC<u>G</u>CTTGCAGT<u>C</u>GTTGC | 53 |
| 23 | *Chenopodium album* | SEQ ID NO: 5 | GA<u>T</u>GTCAACATGAACAAAATGCCAGATGT <u>C</u>GCTATGACTCTTGC<u>T</u>GTTGTTGC | 53 |

TABLE 2-continued

EPSPS target nucleotide sequences SEQ ID NOs: 9-35

| SEQ ID NO: Species | Corresponding to: | Sequence | Length |
|---|---|---|---|
| 24 *Convolvulus arvensis* | SEQ ID NO: 5 | GATGTCAACATGAATAAAATGCCAGATGT CGCCATGACTCTTGCTGTAGTTGC | 53 |
| 25 *Conyza canadensis* | SEQ ID NO: 5 | GATGTGAACATGAACAAGATGCCTGATGT TGCCATGACTCTTGCTGTGGTCGC | 53 |
| 26 *Digitaria sanguinalis* | SEQ ID NO: 5 | GATGTTAACATGAACAAAATGCCCGATGT TGCCATGACTCTTGCCGTGGTTGC | 53 |
| 27 *Digitaria sanguinalis* | SEQ ID NO: 5 | GACGTCAACATGAACAAAATGCCTGATGT CGCAATGACTCTTGCTGTGGTTGC | 53 |
| 28 *Echinochloa colona* | SEQ ID NO: 5 | GATGTCAACATGAACAAAATGCCTGATGT TGCCATGACTCTTGCTGTGGTCGC | 53 |
| 29 *Echinochloa crus-galli* | SEQ ID NO: 5 | GATGTCAACATGAACAAAATGCCTGATGT TGCCATGACTCTTGCTGTGGTCGC | 53 |
| 30 *Euphorbia heterophylla* | SEQ ID NO: 5 | GATGTGAACATGAACAAAATGCCAGATGT CGCTATGACATTGGCTGTGGTTGC | 53 |
| 31 *Ipomoea hederacea* | SEQ ID NO: 5 | GATGTCAACATGAACAAAATGCCAGATGT TGCCATGACTCTTGCTGTAGTTGC | 53 |
| 32 *Lolium multiflorum* | SEQ ID NO: 5 | GATGTCAACATGAACAAAATGCCTGATGT TGCCATGACTCTTGCCGTTGTTGC | 53 |
| 33 *Senna obtusifolia* | SEQ ID NO: 5 | GATGTCAACATGAACAAGATGCCAGATGT TGCCATGACTCTTGCTGTAGTTGC | 53 |
| 34 *Sorghum halepense* | SEQ ID NO: 5 | GATGTTAACATGAACAAAATGCCTGATGT TGCCATGACTCTTGCTGTGGTTGC | 53 |
| 35 *Xanthium strumarium* | SEQ ID NO: 5 | GATGTTAACATGAACAAAATGCCAGATGT TGCCATGACGCTTGCAGTCGTTGC | 53 |

Example 2. Bioactive EPSPS Trigger Molecules Increase Susceptibility of Glyphosate-Resistant Palmer amaranth to Glyphosate The efficacies of mid-sized bioactive polynucleotide trigger molecules comprising SEQ ID NOs: 3 and 4 or SEQ ID NOs: 5 and 6 were assessed in glyphosate-resistant *Palmer amaranth* in relation to a 24-mer trigger comprising SEQ ID NOs: 7 and 8, which was known to sensitize glyphosate-resistant *Palmer amaranth* to glyphosate. Double stranded RNA (dsRNA) triggers comprising polynucleotide sequences of SEQ ID NOs: 3 and 4, SEQ ID NOs: 5 and 6, and SEQ ID NOs: 7 and 8 were produced and the triggers were formulated with 0.5% SILWET® L-77, 2% AMS, and 20 mM phosphate buffer to the desired concentration. The trigger formulations were then topically applied to the leaves of glyphosate-resistant *Amaranthus palmeri* plants ("R-22"). Control plants were either untreated or treated with the 0.5% SILWET® L-77, 2% AMS, and 20 mM phosphate buffer solution. One day after treatment, WEATHERMAX® brand glyphosate herbicide (RU Wmax, Monsanto, St Louis, Mo.) was applied to the plants at 1.5 lb/ac. 11 days after treatment (DAT) with EPSPS trigger polynucleotides the percent growth reduction of the dsRNA treated plants was assessed relative to untreated control plants by visual score. At 14 DAT the fresh weight of the dsRNA treated and control plants were determined. Four replications were performed per treatment. As shown in Table 3, the mid-sized polynucleotide trigger molecules corresponding to SEQ ID NOs: 3 and 4 or SEQ ID NOs: 5 and 6, showed similar activity to the trigger sequence corresponding to SEQ ID NOs: 7 and 8 in sensitizing glyphosate-resistant *Amaranthus palmeri* plants to glyphosate. See also FIG. 1.

TABLE 3

Activity of EPSPS trigger polynucleotides in glyphosate-resistant *Amaranthus palmeri*

| Treatment | Concentration | visual 11-DAT | | Fresh weight 14-DAT | |
|---|---|---|---|---|---|
| SEQ ID NO | (nmole) | Average | Stdev | Average | Stdev |
| formulation control | — | 30.0 | 11.5 | 27.7 | 13.1 |
| SEQ ID NO 7/8 | 2 nmole | 47.5 | 5.0 | 19.0 | 7.7 |
| SEQ ID NO 7/8 | 4 nmole | 88.8 | 12.5 | 95.3 | 8.6 |
| SEQ ID NO 7/8 | 8 nmole | 90.0 | 7.1 | 91.8 | 5.4 |
| SEQ ID NO 7/8 | 16 nmole | 85.8 | 11.8 | 93.7 | 6.6 |
| SEQ ID NO 5/6 | 2 nmole | 48.8 | 17.5 | 18.2 | 10.9 |
| SEQ ID NO 5/6 | 4 nmole | 41.3 | 4.8 | 94.0 | 5.6 |
| SEQ ID NO 5/6 | 8 nmole | 93.8 | 2.5 | 96.2 | 2.8 |
| SEQ ID NO 5/6 | 16 nmole | 81.3 | 13.1 | 90.7 | 9.5 |
| SEQ ID NO 3/4 | 2 nmole | 46.3 | 18.0 | 24.0 | 3.7 |
| SEQ ID NO 3/4 | 4 nmole | 28.8 | 10.3 | 94.7 | 5.4 |

TABLE 3-continued

Activity of EPSPS trigger polynucleotides in
glyphosate-resistant *Amaranthus palmeri*

| Treatment | Concentration | visual 11-DAT | | Fresh weight 14-DAT | |
|---|---|---|---|---|---|
| SEQ ID NO | (nmole) | Average | Stdev | Average | Stdev |
| SEQ ID NO 3/4 | 8 nmole | 88.3 | 10.4 | 88.4 | 9.5 |
| SEQ ID NO 3/4 | 16 nmole | 90.0 | 13.5 | 97.0 | 2.7 |

Example 3. Bioactive EPSPS Trigger Molecules Increase Susceptibility of Glyphosate-Resistant Waterhemp to Glyphosate The efficacies of mid-sized polynucleotide trigger molecules comprising SEQ ID NOs: 3 and 4 or SEQ ID NOs: 5 and 6, were assessed in glyphosate-resistant Waterhemp (*Amaranthus rudis*) in relation to a 24-mer trigger comprising SEQ ID NOs: 7 and 8. dsRNA triggers comprising polynucleotide sequences of SEQ ID NOs: 3 and 4, SEQ ID NOs: 5 and 6, and SEQ ID NOs: 7 and 8 were produced and the triggers were each formulated with 0.5% SILWET® L-77, 2% AMS, and 20 mM phosphate buffer to a concentration of 8 nmol. The trigger formulations were then topically applied to the leaves of glyphosate-resistant Waterhemp. Control plants were either untreated or treated with a solution of 0.5% SILWET® L-77, 2% AMS, and 20 mM phosphate buffer. One day after treatment with the trigger formulation, WEATHERMAX® brand glyphosate herbicide was applied to the plants at 1.5 lb/ac. Four replications were performed per treatment. The fresh weight of the plants was determined 14 DAT with EPSPS trigger polynucleotides and the fresh weight % compared to control plants (treated with WEATHERMAX® brand glyphosate herbicide alone) was calculated. See Table 4. As shown in Table 4, the trigger polynucleotides comprising SEQ ID NO 3/4 or SEQ ID NO 5/6 showed similar activity to trigger polynucleotides comprising SEQ ID NO 7/8 in sensitizing glyphosate-resistant Waterhemp plants to glyphosate.

TABLE 4

Activity of EPSPS trigger polynucleotides
in glyphosate-resistant waterhemp

| Treatment and SEQ ID NO | Concentration | % Control Fresh wt. average |
|---|---|---|
| Buffer | — | 35 |
| SEQ ID NO 7/8 | 8 nmol | 85 |
| SEQ ID NO 3/4 | 8 nmol | 78 |
| SEQ ID NO 5/6 | 8 nmol | 83 |

Figure 2:
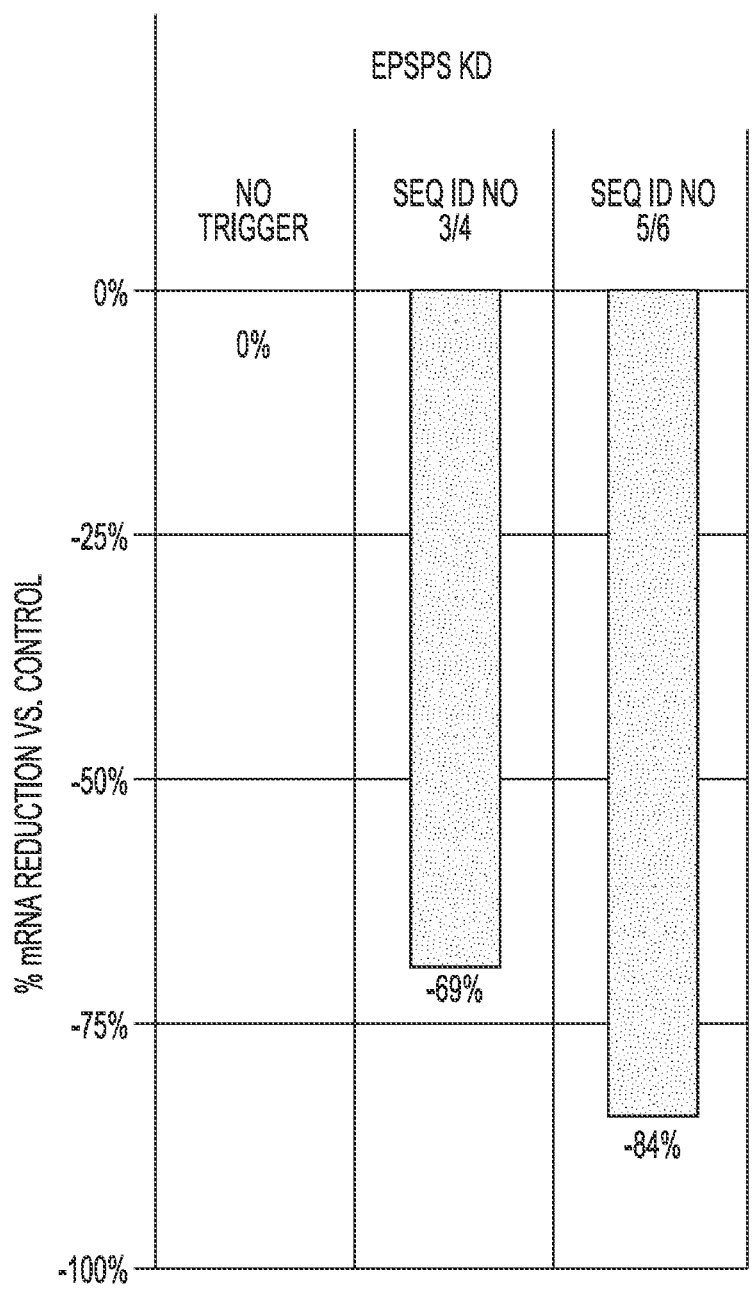

Example 4. dsRNA Trigger Molecules Comprising SEQ ID NO 3/4 and SEQ ID NO 5/6 Reduce EPSPS mRNA in Palmer Protoplasts The activities of mid-sized bioactive polynucleotide trigger molecules corresponding to SEQ ID NOs: 3 and 4 or SEQ ID NOs: 5 and 6 were assessed in *Amaranthus palmeri* protoplasts. A 6 ug dose of each dsRNA trigger (SEQ ID NO 3/4 or SEQ ID NO 5/6) was added to *Amaranthus palmeri* protoplasts. As shown in FIG. 2, the dsRNA triggers comprising SEQ ID NOs: 3 and 4 or SEQ ID NOs: 5 and 6 reduced EPSPS mRNA levels by 69% and 84%, respectively.

Figure 3:
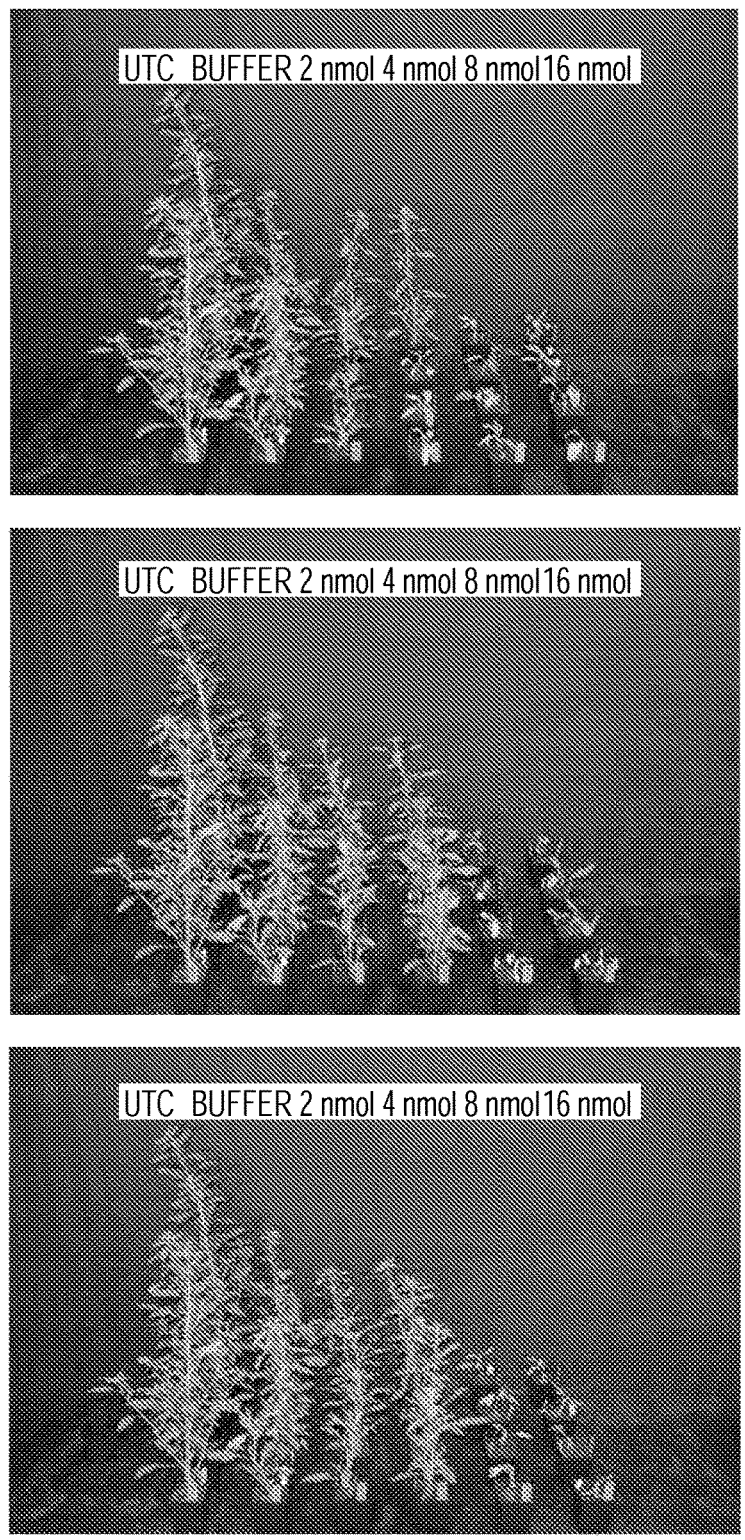

Example 5. Bioactive EPSPS Trigger Molecules Increase Susceptibility of Glyphosate-Resistant Waterhemp to Glyphosate The efficacies of mid-sized bioactive polynucleotide trigger molecules comprising SEQ ID NOs 3 and 4 or SEQ ID NOs 5 and 6 were assessed in glyphosate-resistant Waterhemp (WH13) in relation to a 24-mer trigger comprising SEQ ID NOs 7 and 8, which was known to sensitize glyphosate-resistant Waterhemp to glyphosate. Double stranded RNA (dsRNA) triggers comprising polynucleotide sequences of SEQ ID NOs: 3 and 4, SEQ ID NOs: 5 and 6, and SEQ ID NOs: 7 and 8 were produced and the bioactive trigger polynucleotides were formulated with 0.5% SILWET® L-77, 2% AMS, and 20 mM phosphate buffer to a concentration of 2 nmol, 4 nmol, 8 nmol or 16 nmol. The trigger formulations were then topically applied to the leaves of glyphosate-resistant Waterhemp plants ("WH13"). Control plants were either untreated or treated with the 0.5% SILWET® L-77, 2% AMS, and 20 mM phosphate buffer solution. One day after treatment, WEATHERMAX® brand glyphosate herbicide (RU Wmax, Monsanto, St Louis, Mo.) was applied to the plants at 1.5 lb/ac. Four replications were performed per treatment. FIG. 3 shows the plants at 14 days after treatment. As shown in FIG. 3, the mid-sized bioactive trigger polynucleotide molecules comprising SEQ ID NOs: 5 and 6 or SEQ ID NOs: 3 and 4, sensitize glyphosate-resistant Waterhemp plants to glyphosate.

Example 6. A Method to Control Weeds in a Field

A composition comprising at least one bioactive trigger polynucleotide comprising a nucleotide sequence that is essentially identical and/or essentially complementary to SEQ ID NOs: 3-35 or a fragment thereof and a transfer agent that mobilizes the bioactive trigger polynucleotide into a plant cell is applied to a field of growing plants at an effective concentration. For example, an effective concentration of a bioactive trigger polynucleotide can have a use rate of about 1 to 30 grams or more per acre depending on the size of the bioactive trigger polynucleotide and the number of bioactive trigger polynucleotides in the composition. The bioactive trigger polynucleotide of the composition may be a dsRNA, ssDNA or dsDNA or a combination thereof. An effective concentration of bioactive trigger polynucleotides modulate the expression of an EPSPS gene in one or more target weed plant species to promote sensitivity of the target weed plant species to glyphosate. A glyphosate-containing herbicide is applied to control weeds in the field.

The composition optionally comprises a bioactive trigger polynucleotide that modulates the expression of an essential gene and optionally a herbicide that has a different mode of action relative to glyphosate. The composition may include one or more additional herbicides as needed to provide effective multi-species weed control. A composition comprising 1 or 2 or 3 or 4 or more of bioactive trigger polynucleotide that are essentially identical or essentially complementary to SEQ ID NOs: 3-35 or a fragment thereof would enable broad activity of the composition against the multiple weed species that occur in a field environment.

Example 7. Tiling of the EPSPS cDNA for dsRNA Trigger Testing in GR Palmer

The EPSPS cDNA of SEQ ID NO: 1 was tiled across the entire length of the cDNA to identify target sequences for bioactive trigger polynucleotides covering as shown in Table 5. The target nucleotide sequence were chosen to be approximately 47-62 bp in length. Bioactive trigger polynucleotides comprising a nucleotide sequence having at least 85% identity or complementarity to SEQ ID NOs: 36-66 were tested for the ability to sensitize glyphosate-resistant Waterhemp to glyphosate.

TABLE 5

EPSPS target nucleotide sequences SEQ ID NO 36-66

| SEQ ID NO | Size | Sense |
|---|---|---|
| 36 | 49 | GCTCAAGCTACTACCATCAACAATGGTGTCCATACTGGTCAATTGCACC |
| 37 | 60 | GCACCATACTTTACCCAAAACCCAGTTACCCAAATCTTCAAAAACTCTTAATTTTGGATC |
| 38 | 60 | GATCAAACTTGAGAATTTCTCCAAAGTTCATGTCTTTAACCAATAAAAGAGTTGGTGGGC |
| 39 | 48 | GCAATCATCAATTGTTCCCAAGATTCAAGCTTCTGTTGCTGCTGCAGC |
| 40 | 54 | GCTGAGAAACCTTCATCTGTCCCAGAAATTGTGTTACAACCCATCAAAGAGATC |
| 41 | 52 | GATCTCTGGTACTGTTCAATTGCCTGGGTCAAAGTCTTTATCCAATCGAATC |
| 42 | 54 | GAATCCTTCTTTTAGCTGCTTTGTCTGAGGGCACAACAGTGGTCGACAACTTGC |
| 43 | 47 | GCTGTATAGTGATGATATTCTTTATATGTTGGACGCTCTCAGAACTC |
| 44 | 61 | GCAGTCGTAGAGGGTTGTGGTGGTCTGTTTCCTGTTGGTAAAGATGGAAAGGAAGAGATTC |
| 45 | 48 | GATTCAACTTTTCCTTGGTAATGCAGGAACAGCGATGCGCCCATTGAC |
| 46 | 56 | GACAGCTGCGGTTGCCGTTGCTGGAGGAAATTCAAGTTATGTGCTTGATGGAGTAC |
| 47 | 52 | GTACCAAGAATGAGGGAGCGCCCCATTGGGGATCTGGTAGCAGGTCTAAAGC |
| 48 | 53 | GCAACTTGGTTCAGATGTAGATTGTTTTCTTGGCACAAATTGCCCTCCTGTTC |
| 49 | 56 | GTTCGGGTCAATGCTAAAGGAGGCCTTCCAGGGGGCAAGGTCAAGCTCTCTGGATC |
| 50 | 54 | GATCGGTTAGTAGCCAATATTTAACTGCACTTCTCATGGCTACTCCTTTGGGTC |
| 51 | 48 | GTCTTGGAGACGTGGAGATTGAGATAGTTGATAAATTGATTTCTGTAC |
| 52 | 58 | GTACCGTATGTTGAAATGACAATAAAGTTGATGGAACGCTTTGGAGTATCCGTAGAAC |
| 53 | 51 | GAACATAGTGATAGTTGGGACAGGTTCTACATTCGAGGTGGTCAGAAATAC |
| 54 | 55 | GTCAGAAATACAAATCTCCTGGAAAGGCATATGTTGAGGGTGATGCTTCAAGTGC |
| 55 | 51 | GCTAGCTACTTCCTAGCCGGAGCCGCCGTCACTGGTGGGACTGTCACTGTC |
| 56 | 55 | GTCAAGGGTTGTGGAACAAGCAGTTTACAGGGTGATGTAAAATTTGCCGAAGTTC |
| 57 | 56 | GTTCTTGAGAAGATGGGTTGCAAGGTCACCTGGACAGAGAATAGTGTAACTGTTAC |
| 58 | 54 | GTTACTGGACCACCCAGGGATTCATCTGGAAAGAAACATCTGCGTGCTATCGAC |
| 59 | 62 | GCCTTGTATGCAGATGGGCCCACCGCCATCAGAGATGTGGCTAGCTGGAGAGTGAAGGAAAC |
| 60 | 50 | GAAACCGAACGGATGATTGCCATTTGCACAGAACTGAGAAAGCTTGGGGC |
| 61 | 52 | GCAACAGTTGAGGAAGGATCTGATTACTGTGTGATCACTCCGCCTGAAAAGC |
| 62 | 51 | GCTAAACCCCACCGCCATTGAAACTTATGACGATCACCGAATGGCCATGGC |
| 63 | 57 | GCATTCTCTCTTGCTGCCTGTGCAGATGTTCCCGTCACTATCCTTGATCCGGGATGC |
| 64 | 54 | GCACCCGTAAAACCTTCCCGGACTACTTTGATGTTTTAGAAAAGTTCGCCAAGC |
| 65 | 50 | GAACTCTTGGTTTAAAAGTGGAGGATGATAGTACAGCCAAAAGGGCAGTC |
| 66 | 53 | GACGTCAACATGAACAAAATGCCAGATGTTGCTATGACTCTTGCAGTTGTTGC |

Double stranded RNA (dsRNA) triggers comprising polynucleotide sequences corresponding to SEQ ID NOs: 36-62 were produced and the bioactive trigger polynucleotides were formulated with 0.5% SILWET® L-77, 2% AMS, and 20 mM phosphate buffer to a final concentration of 8 nmol. The trigger formulations were then topically applied to the leaves of glyphosate-resistant Waterhemp plants ("WH13"). Control plants were either untreated or treated with the formulation 0.5% SILWET® L-77, 2% AMS, and 20 mM phosphate "buffer" solution. Additionally dsRNA comprising SEQ ID NOs: 7 and 8 (24-mer EPSPS trigger) was applied as a control. One day after treatment, WEATHERMAX® brand glyphosate herbicide (RU Wmax, Monsanto, St Louis, Mo.) was applied to the plants at 1.5 lb/ac.

Figure 4:
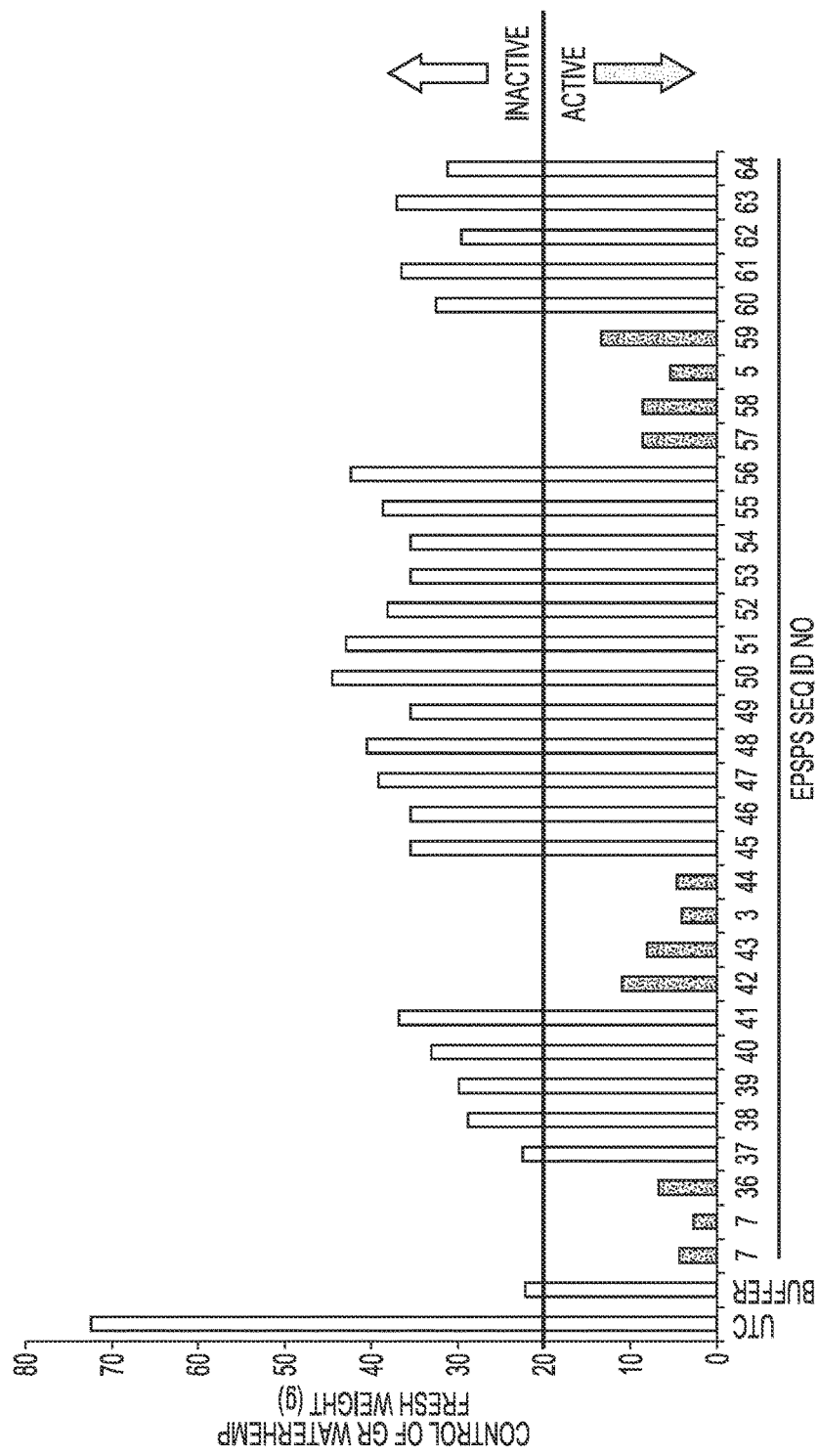

Three replications were performed per treatment. FIG. 4 shows the fresh weight (g) of the plants at 14 days after treatment. As shown in FIG. 4, several mid-sized bioactive trigger polynucleotide molecules sensitize glyphosate-resistant Waterhemp plants to glyphosate, in particular, in addition to bioactive trigger polynucleotides comprising SEQ ID NOs: 3 and 4 or SEQ ID NOs: 5 and 6, it was observed that bioactive trigger polynucleotides corresponding to SEQ ID NOs: 36, 42, 43, 44, 57, 58 and 59 had good efficacy.

I claim:

1. A method of controlling growth, development or reproductive ability of a plant, comprising: topically treating the plant with a composition comprising a double-stranded RNA (dsRNA) polynucleotide and a transfer agent, wherein the dsRNA polynucleotide comprises (a) a strand consisting of SEQ ID NO: 3 or 5; and (b) a strand comprising the reverse complement of (a), whereby the growth, development or reproductive ability of the plant is reduced, relative to a plant not treated with the composition.

2. The method of claim 1, wherein the transfer agent is selected from the group consisting of an organosilicone surfactant, a cationic lipid reagent, and a plant hormone.

3. The method of claim 2, wherein the cationic lipid reagent is N41-(2,3-Dioleoyloxy)propyll-N,N,N-trimethyl-ammonium methyl-sulfate (DOTAP), or wherein the plant hormone is brassinosteroid.

4. The method of claim 1, wherein the plant is selected from the group consisting of Amaranthus palmeri, Amaranthus rudis, Amaranthus albus, Amaranthus chlorostachys, Amaranthus graecizans, Amaranthus hybridus, Amaranthus lividus, Amaranthus spinosus, Amaranthus thunbergii, Amaranthus viridis, Lolium multiflorum, Lolium rigidum, Ambrosia artemisiifolia, Ambrosia trifida, Euphorbia heterophylla, Kochia scoparia, Abutilon theophrasti, Sorghum halepense, Chenopodium album, Commelina diffusa, Convolvulus arvensis, Conyza canadensis, Digitaria sanguinalis, and Xanthium strumarium.

5. The method of claim 1, wherein the composition further comprises one or more of an EPSPS-inhibitor herbicide and two different dsRNA polynucleotides, one consisting of a strand of SEQ ID NO: 3 and its reverse complement, and the other consisting of a strand of SEQ ID NO: 5 and its reverse complement.

6. The method of claim 5, wherein the composition further comprises a component selected from the group consisting of an auxin-like herbicide, 3,6-dichloro-o-anisic acid, 2,4-dichlorophenoxyacetic acid, and one or more herbicides different from the one or more of the EPSPS-inhibitor herbicide.

7. A composition comprising: a dsRNA polynucleotide and a transfer agent, wherein the dsRNA polynucleotide comprises (a) a strand consisting of SEQ ID NO: 3 or 5; and (b) a strand comprising the reverse complement of (a).

8. The composition of claim 7, wherein the transfer agent is selected from the group consisting of an organosilicone surfactant, a cationic lipid reagent, and brassinosteroid.

9. The composition of claim 8, wherein the composition further comprises ammonium sulfate.

10. The composition of claim 8, wherein the cationic lipid reagent is N41-(2,3-Dioleoyloxy)propyll-N,N,N-trimethyl-ammonium methyl-sulfate (DOTAP).

11. The composition of claim 7, further comprising an EPSPS-inhibitor herbicide.

12. The composition of claim 11, wherein the EPSPS-inhibitor herbicide is glyphosate.

13. The composition of claim 11, further comprising a non-EPSPS-inhibitor herbicide.

14. The composition of claim 13, wherein the non-EPSPS-inhibitor herbicide is 3,6-dichloro-o-anisic acid or 2,4-dichlorophenoxyacetic acid.

15. A method of sensitizing a weedy plant to an EPSPS-inhibitor herbicide comprising: treating the weedy plant with a dsRNA polynucleotide, wherein the dsRNA polynucleotide comprises (a) a strand consisting of SEQ ID NO: 3 or 5; and (b) a strand comprising the reverse complement of (a), whereby the weedy plant is more sensitive to the EPSPS-inhibitor herbicide relative to a weedy plant not treated with the dsRNA polynucleotide.

16. The method of claim 15, wherein the EPSPS-inhibitor herbicide is glyphosate.

17. The method of claim 15, wherein the weedy plant is resistant to glyphosate, 3,6-dichloro-o-anisic acid, sulfonylurea, or a combination thereof.

18. The method of claim 15, wherein the weedy plant is selected from the group consisting of *Amaranthus palmeri, Amaranthus rudis, Amaranthus albus, Amaranthus chlorostachys, Amaranthus graecizans, Amaranthus hybridus, Amaranthus lividus, Amaranthus spinosus, Amaranthus thunbergii, Amaranthus viridis, Lolium multiflorum, Lolium rigidum, Ambrosia artemisiifolia, Ambrosia trifida, Euphorbia heterophylla, Kochia scoparia, Abutilon theophrasti, Sorghum halepense, Chenopodium album, Commelina diffusa, Convolvulus arvensis, Conyza canadensis, Digitaria sanguinalis*, and *Xanthium strumarium*.

* * * * *